(12) United States Patent
Shacham-Diamand et al.

(10) Patent No.: US 8,702,959 B2
(45) Date of Patent: Apr. 22, 2014

(54) SYSTEM AND METHOD FOR DETECTING A SUBSTANCE IN LIQUID

(75) Inventors: Yosi Shacham-Diamand, Zikhron-Yaakov (IL); Hadar Ben-Yoav, Ramat-Gan (IL); Shimshon Belkin, Kiryat Ono (IL); Rami Pedahzur, Jerusalem (IL); Alva Biran, Mizpe Hila (IL); Georg Reifferscheid, Neuwied (DE); Sebastian Buchinger, Bonn (DE)

(73) Assignees: Ramot at Tel-Aviv University Ltd., Tel-Aviv (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 248 days.

(21) Appl. No.: 12/981,592

(22) Filed: Dec. 30, 2010

(65) Prior Publication Data
US 2011/0155587 A1 Jun. 30, 2011

Related U.S. Application Data

(60) Provisional application No. 61/282,215, filed on Dec. 31, 2009.

(51) Int. Cl.
*G01N 27/27* (2006.01)
*C12N 1/21* (2006.01)

(52) U.S. Cl.
USPC ............ 205/777.5; 422/68.1; 422/82.01; 435/287.1; 435/6.1; 435/287.2; 435/243; 204/403.01

(58) Field of Classification Search
USPC ............ 204/400, 403.01, 412; 435/320.1, 435/252.3, 287.1, 287.2, 6.1, 243; 422/68.1, 82.01; 205/775, 777.5
See application file for complete search history.

(56) References Cited

U.S. PATENT DOCUMENTS

| | | | |
|---|---|---|---|
| 2005/0252777 A1* | 11/2005 | Li | 204/600 |
| 2007/0281288 A1* | 12/2007 | Belkin et al. | 435/4 |
| 2008/0044844 A1* | 2/2008 | Belkin et al. | 435/29 |
| 2008/0262321 A1* | 10/2008 | Erad et al. | 600/301 |
| 2009/0297913 A1* | 12/2009 | Zhang et al. | 429/33 |
| 2010/0072396 A1* | 3/2010 | Agranat et al. | 250/459.1 |

OTHER PUBLICATIONS

Bauer et al. "Zeptomole-Detection Biosensor for Alkaline Phosphatase in an Electrochemical Immunoassay for 2,4-Dichlorophenoxyacetic Acid", Analytical Chemistry, 68(15): 2453-2458, Aug. 1, 1996.

Ben-Yoav et al. "A Novel Microfluidic Whole Cell Biosensor Based on Electrochemical Detection for Water Toxicity Analysis", ECS Transactions, 214th ECS Meeting, Honolulu, HI, USA, Oct. 12-17, 2008, 16(11): 187-197, Oct. 2008.

Oda et al. "Evaluation of the New System (Umu-Test) for the Detection of Environmental Mutagens and Carcinogens", Mutation Research, 147: 219-229, 1985.

(Continued)

*Primary Examiner* — Jennifer Dieterle

(57) ABSTRACT

A system for analyzing a liquid is provided. The system comprises:
an electrochemical unit having an electrochemical microchamber for receiving a sample of the liquid and electrochemically analyzing the sample; and
a microfluidic unit being attached to the electrochemical unit and having microchannels constituted for sampling the sample in situ and feeding the sample to the electrochemical microchamber. Also provided are nucleic acid constructs and cells comprising same for analyte detection.

16 Claims, 26 Drawing Sheets
(23 of 26 Drawing Sheet(s) Filed in Color)

(56) References Cited

OTHER PUBLICATIONS

Popovtzer et al. "Mathematical Model of Whole Cell Based Bio-Chip: An Electrochemical Biosensor for Water Toxicity Detection", Journal of Electroanalytical Chemistry, 602: 17-23, 2007.

Popovtzer et al. "Novel Integrated Electrochemical Nano-Biochip for Toxicity Detection in Water", Nano Letters, 5(6): 1023-1027, 2005.

Regenfelder et al. "G Proteins in Ustilago Maydis: Transmission of Multiple Signals?", The EMBO Journal, 16(8): 1934-1942, 1997.

Reifferscheid et al. "A Microplate Version of the SOS / Umu-Test for Rapid Detection of Genotoxins and Genotoxic Potentials of Environmental Samples", Mutation Research: 253: 215-222, 1991.

Vollmer "Detection of DNA Damage by Use of *Escherichia coli* Carrying RecA'::Lux, UvrA'::Lux, or AlkA'::Lux Reporter Plasmids", Applied and Environmental Microbiology, 63(7): 2566-2571, Jul. 1997.

Xiong et al. "Microorganisms for MEMS", Journal of Microelectromechanical Systems, 16(2): 429-444, Apr. 2007.

* cited by examiner

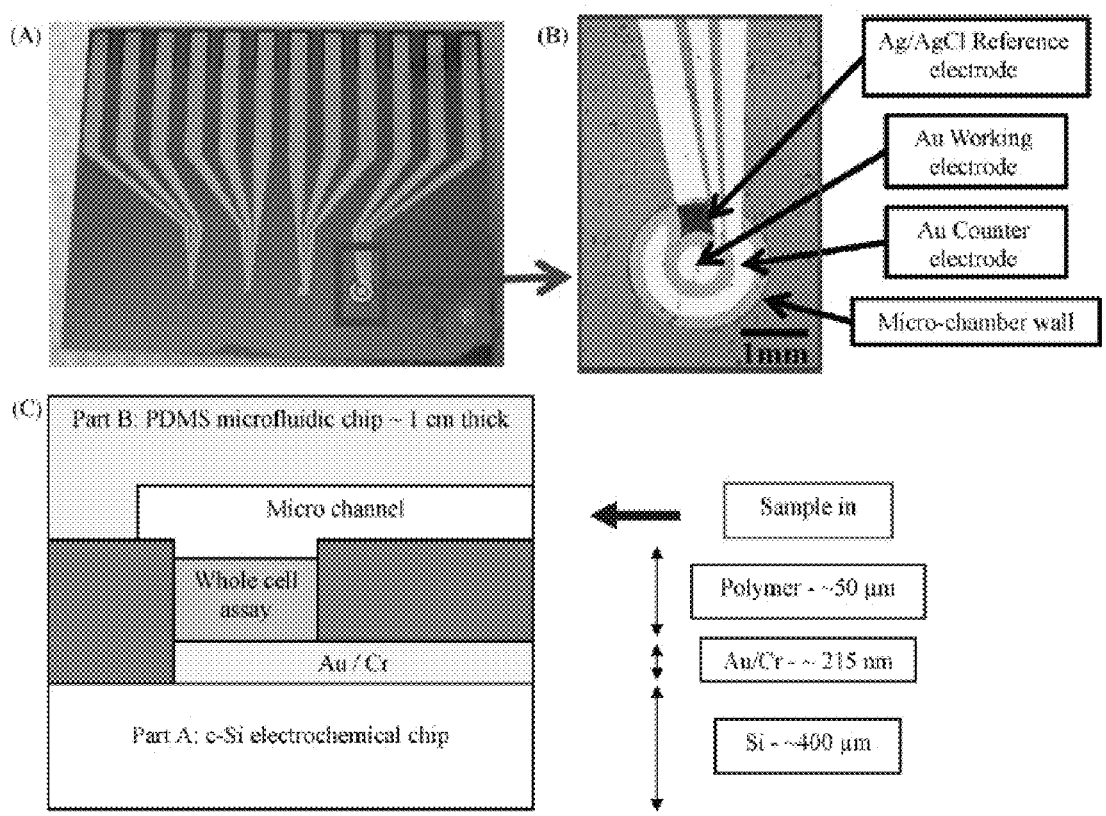
FIGs. 5A-C

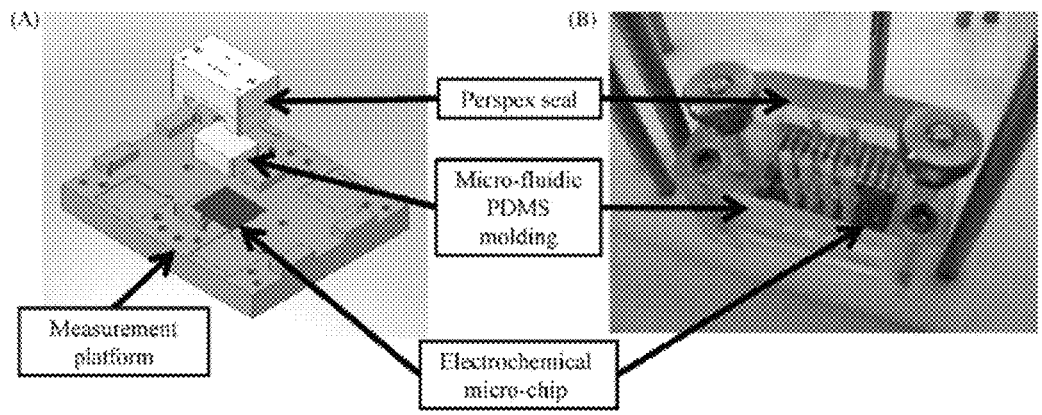
FIGs. 6A-B
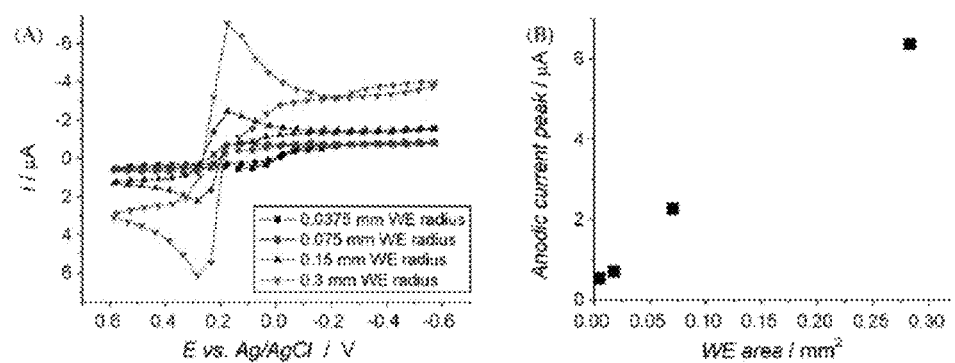
FIGs. 7A-B

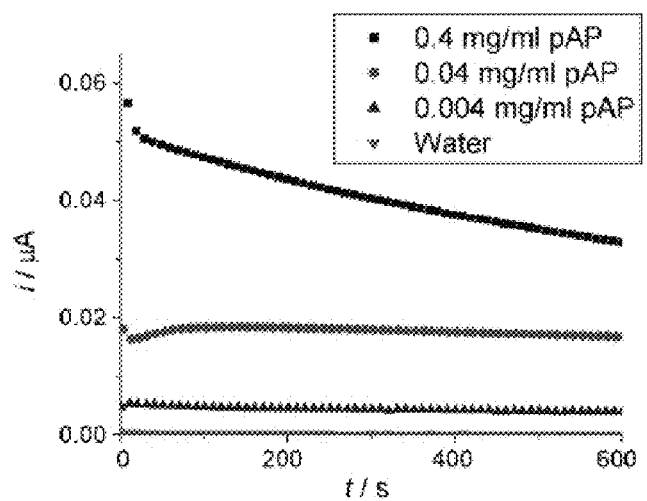
FIG. 9
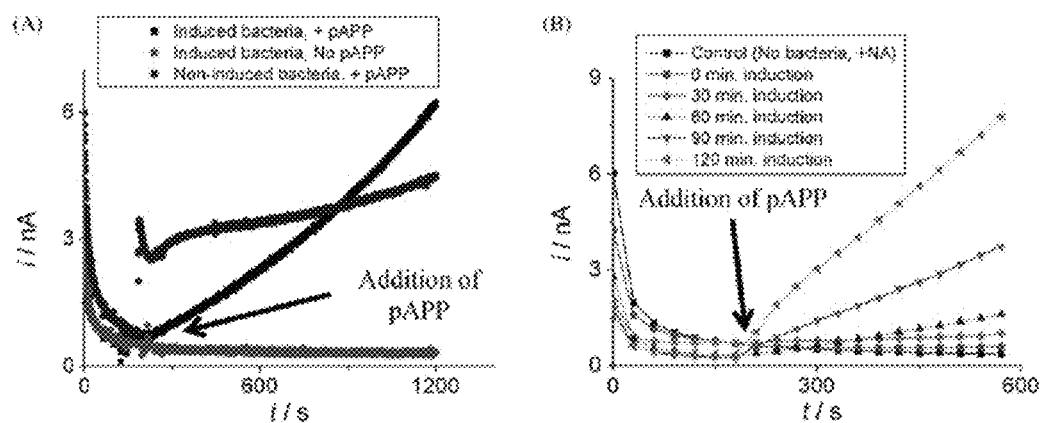
FIGs. 10A-B

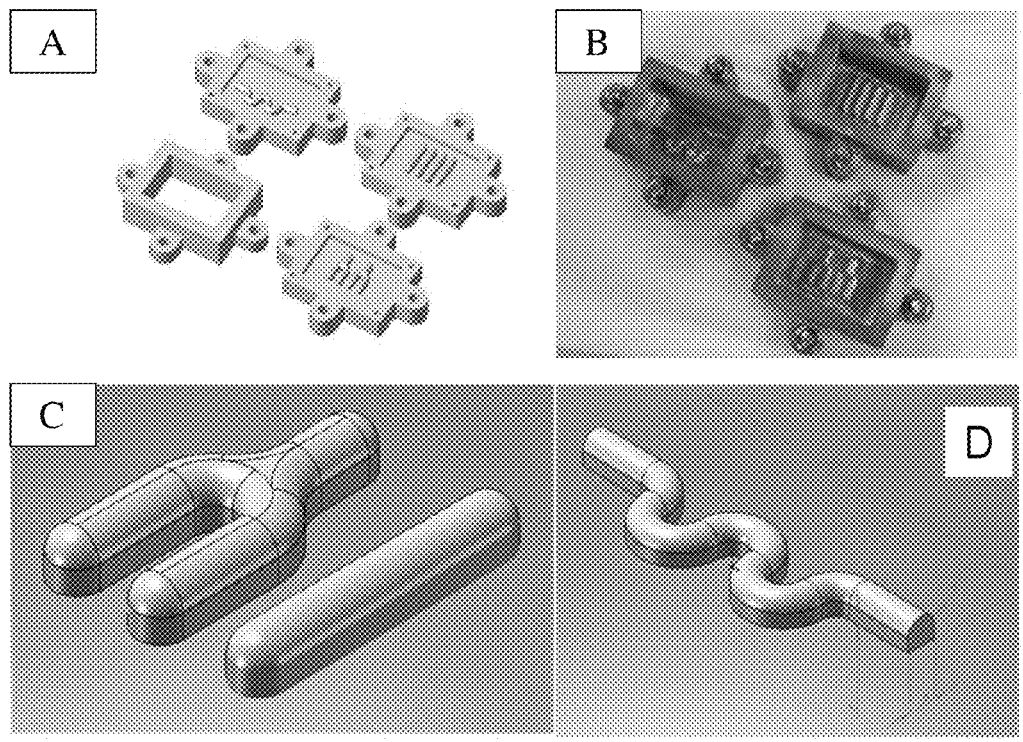
FIGs. 16A-D
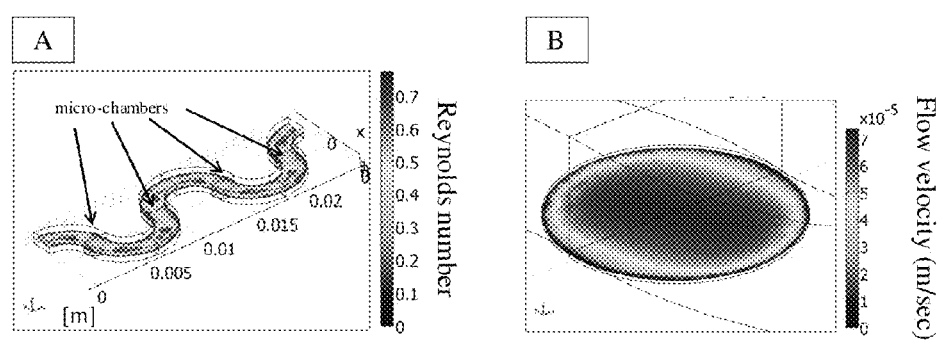
FIGs. 17A-B

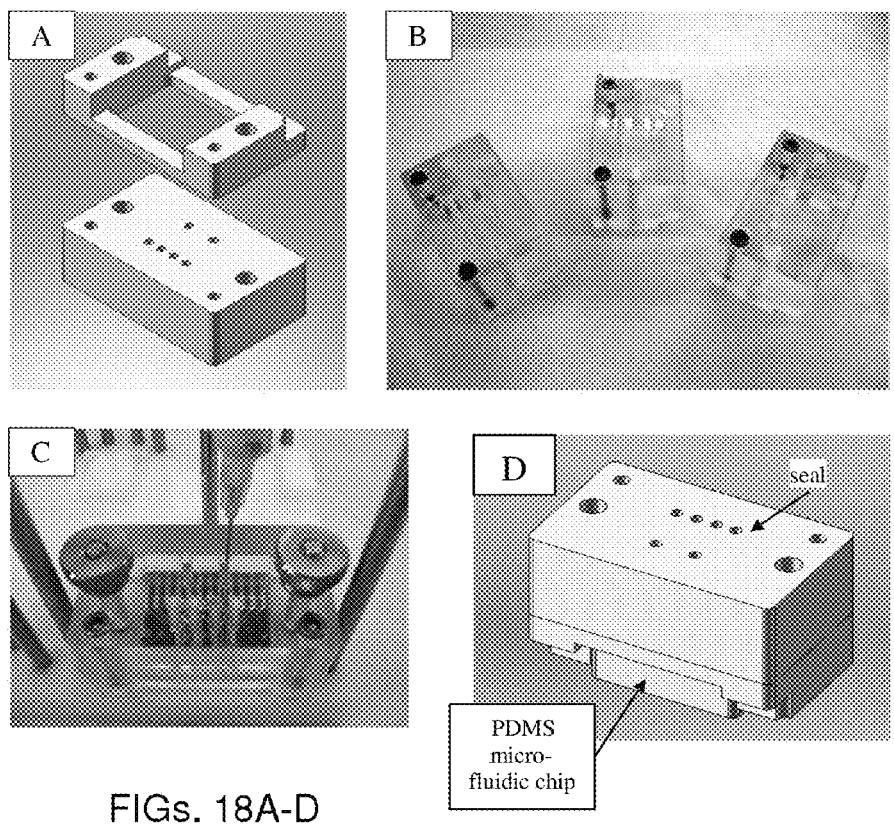
FIGs. 18A-D
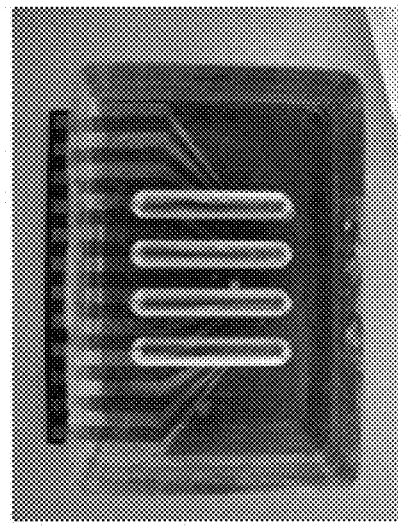
FIG. 19

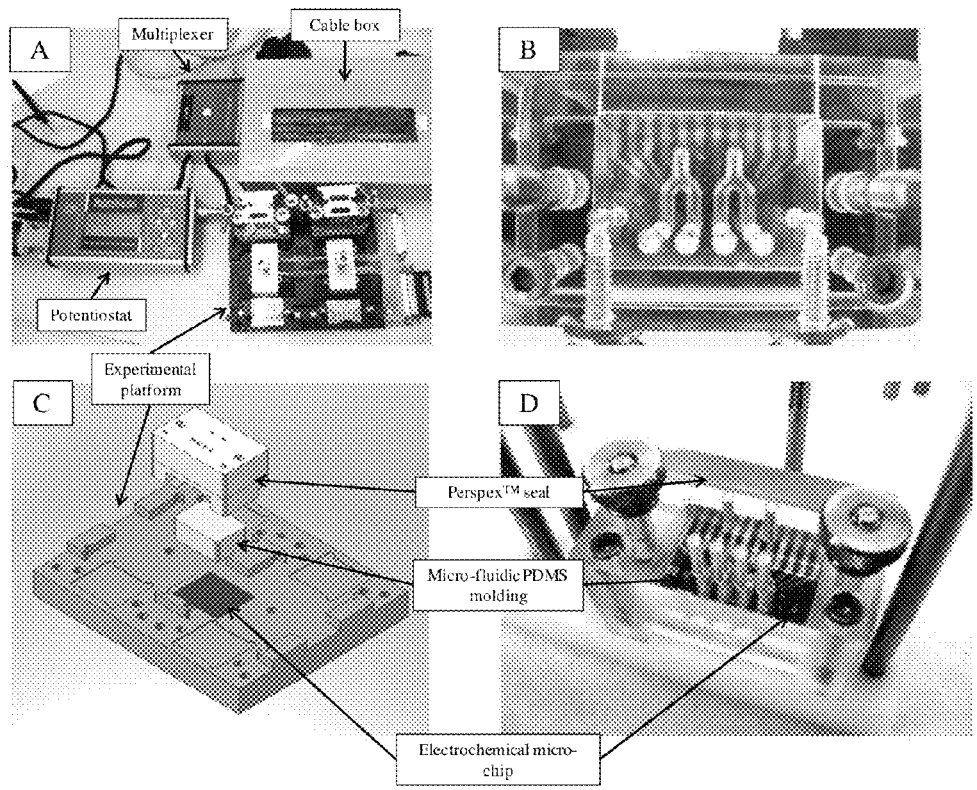
FIG. 20A-D
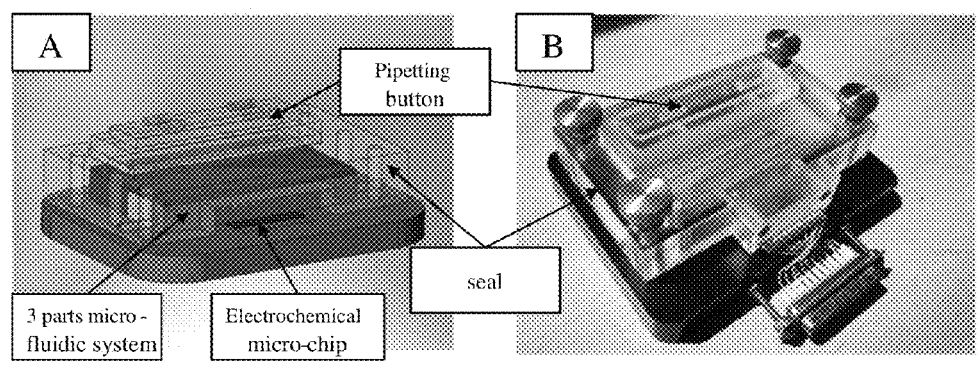
FIG. 21A-B

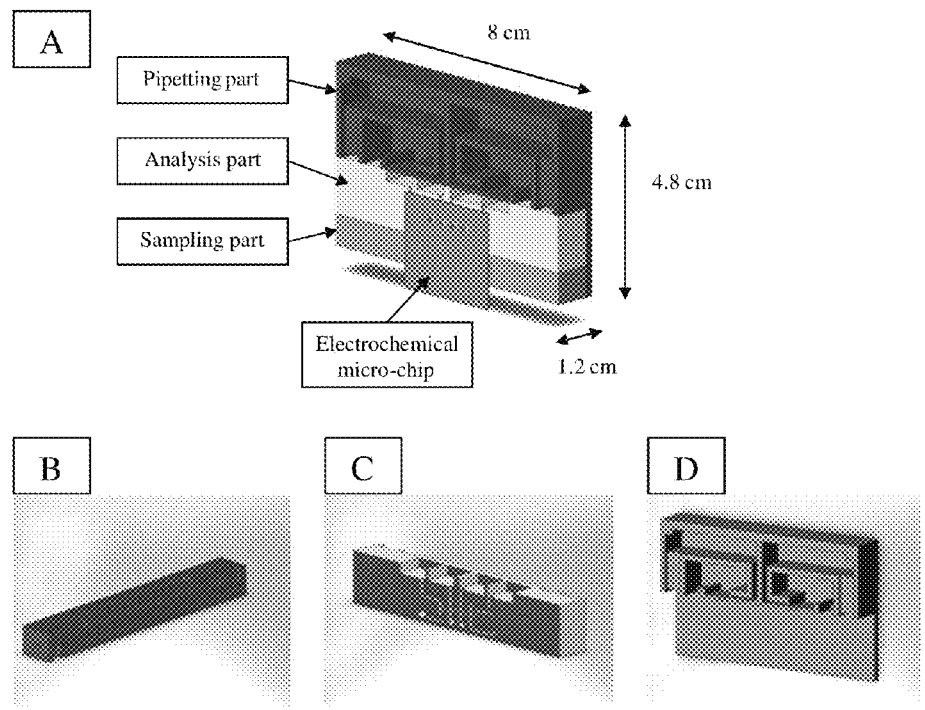
FIGs. 22A-D
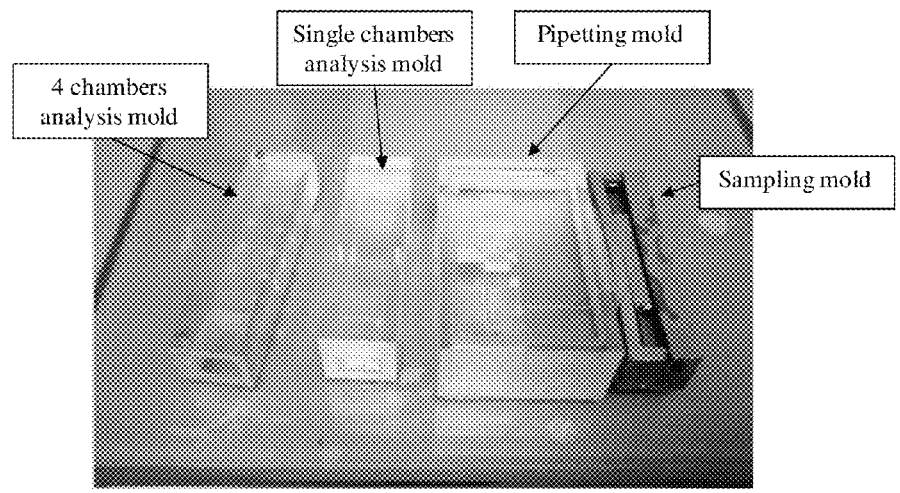
FIG. 23

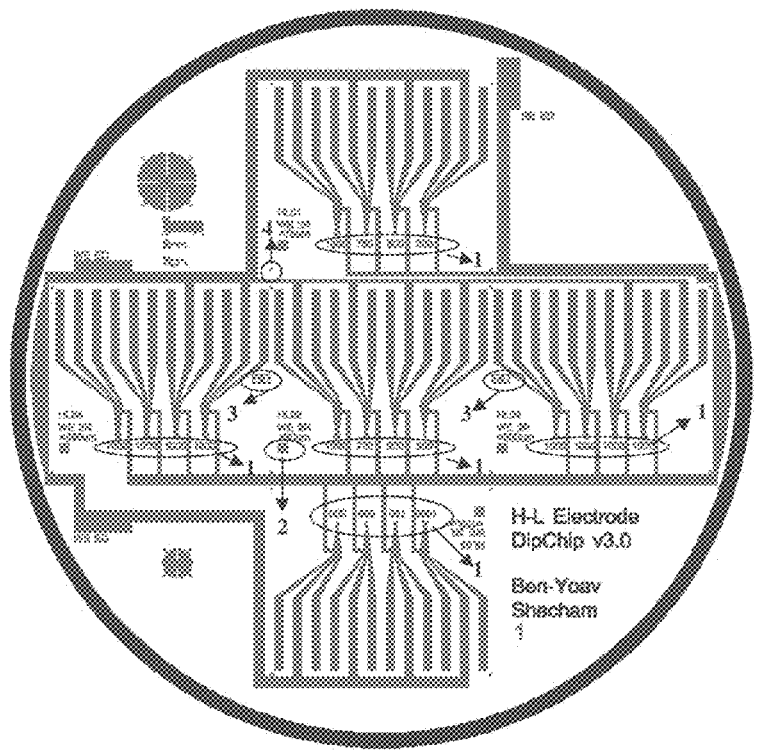
FIG. 28
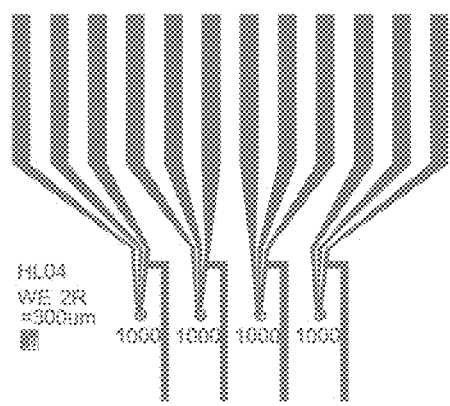 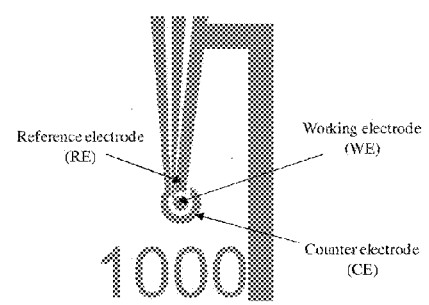
FIG. 29A  FIG. 29B

```
                        SEQUENCE LISTING

<160> NUMBER OF SEQ ID NOS: 20

<210> SEQ ID NO 1
<211> LENGTH: 5856
<212> TYPE: DNA
<213> ORGANISM: Artificial sequence
<220> FEATURE:
<223> OTHER INFORMATION: pBR2TTSsulA  phoA fusion expression construct

<400> SEQUENCE: 1
tcgcgcgttt  cggtgatgac  ggtgaaaacc  tctgacacat  gcagctcccg  gagacggtca       60
cagcttgtct  gtaagcggat  gccgggagca  gacaagcccg  tcagggcgcg  tcagcgggtg      120
ttggcgggtg  tcgggctgg   cttaactatg  cggcatcaga  gcagattgta  ctgagagtgc      180
accatatgcg  gtgtgaaata  ccgcacagat  gcgtaaggag  aaaataccgc  atcaggcgcc      240
attcgccatt  caggctgcgc  aactgttggg  aagggcgatc  ggtgcgggcc  tcttcgctat      300
tacgccagct  ggcgaaaggg  ggatgtgctg  caaggcgatt  aagttgggta  acgccagggt      360
tttcccagtc  acgacgttgt  aaaacgacgg  ccagtgaatt  gtaatacgac  tcactatagg      420
gcgaattcct  ttaatccctt  taattcctgg  attttttctc  cgaaatctgg  gagcgtataa      480
acatctggac  tcgtataaat  cagttgactg  gtttctatgc  cttctttgcc  acatattata      540
tgtatatcaa  ctaataccgt  attattatca  taacctatag  acatagttcc  attgtatttt      600
agcgcgttct  caaattcttc  ttttgatgga  tacgatgatc  catctccgta  cttttcgtt       660 aacgatttgc  ttactggctt  cacaagtctg  ccaatattaa  tctctaatct  tttaaattc       720 ccatttaaaa  aaaatgccat  tgcttcacgc  ttttttgttag  caaacgaaaa  gtcagaacat      780
gaataaagtg  atacttcttc  tattcgagaa  tctccctcaa  attttcaaa   atcacataac      840
```

```
ctcttcgaat tattatttca gccccagagc ggctttcatg gtgtagaaga gatcggtctg    900
gtcggtcagt ccaacaacat tggcggcatg cgggccatac gccgcaatac gcaactgact    960
gccggtatgt tcttgtgaat cctcttcgga gttcccgtaa ctcatcacca tcactgcgcc   1020
atctttggta tttagcgcct gggtgaggcc cggagctttg gtatccggcg caacaatctg   1080
gctggcgtgg gcgtgatcag cggtgactat gaccagcgtg ttaccctcct ttttagcgaa   1140
ttccagcgcc cgttgtacgg cttcatcgag atcgaccgtc tcgccaattt gcccacaagg   1200
attcgcagca tgatcctgtt tatcgattga cgcaccttca acttgcagga aaaagccttt   1260
ctcattttta ctcaacaatt caatggcttt gtcggtcatc tgcgccaggg ttggtacact   1320
gtcattacgt tgcggatttg gcgtacaggt gactgcgggc ttatcgatat tgccatggta   1380
cgttgctttc ggtcctagcc agcgcactgg catattgccg tcagcaaaca ggccaagcag   1440
gggttttttgc tgattcgctt ccgtcaccga attcagtgag gcagcatcgc tcaccaactg   1500
ataaccacgc gcctgtgcct gttcacgcag cgttttttccc tgccattcac cagcggttgc   1560
cgtttcagca aggttttttg cgccgccgcc aagcgtaacg tcggcacgag cgttaagcag   1620
ctgttcggta atcgatcctt ttccgccttt ttccagagcg ttacccggac attttttcact   1680
ggtcgcgctc ggaccgtagc atttgcgcga ggtcacatgt gccaccagcg cagcgggcgt   1740
ggcatcctgc aactctgcgg tagaaacgtt accggtcgcc agacctgcgg cttttgccat   1800
ttccagaatc gttgggtgat ctttttttcgtg aatatcgacg cccagcgcgc cgttataggt   1860
tttgacaccg gttgaccagg cggttgctga tgcagccgag tcggtgacgt agtccggttt   1920
gccggttttt ttattcagcg catagtgagt gtattgcccg gtaagcggta aggcatctat   1980
acctttaaaa aagccgcccg caccttcggc ataattacgt gcggcagtaa tttccgagtc   2040
ccccatccca tcgccaatca gcaaaataat atttttttgca ggtttatcgc taagagaatc   2100
acgcagagcg gcagtctgat cacccgttaa acggcgagca ccgccgggtg cagtaatatc   2160
gccctgagca gcccggtttt ccagaacagg catttctggt gtccgggctt ttgtcacagg   2220
ggtaaacagt aacggtaaga gtgccagtgc aatagtgctt tgtttcactt tattttctcc   2280
atgagctcaa tcaatccagc ccctgtgagt tactgtatgg atgtacagta catccagtga   2340
caacaaagat caaccctatt tcggaaagaa gcctcgcaaa ttttgtcgtt ggtgacggga   2400
aaacataaat taatcttgcc ccttaagaat aagttgccta ttttcgtagt taacggatcc   2460
gttaatgtga atcattcttt tatgttatga ttttaaaagg aattttatga aaagcctctc   2520
ctataagcgg atctataaat cacaagaata cctggcaacg ttgggcacaa ttgaataccg   2580
atcattgttt ggcagttaca gcggtacccg gggatcccga tccccaattc ctggcagttt   2640
atggcgggcg tcctgcccgc caccctccgg gccgttgctt cgcaacgttc aaatccgctc   2700
ccggcggatt tgtcctactc aggagagcgt tcaccgacaa acaacagata aaacgaaagg   2760
cccagtcttt cgactgagcc tttcgtttta tttgatgcct gtcggatccc gatccccaat   2820
tcctggcagt ttatggcggg cgtcctgccc gccaccctcc gggccgttgc ttcgcaacgt   2880
tcaaatccgc tcccggcgga tttgtcctac tcaggagagc gttcaccgac aaacaacaga   2940
taaaacgaaa ggcccagtct ttcgactgag cctttcgttt tatttgatgc ctgtcgactc   3000
aagtaattac ttactggtta gcagaatgaa tcaccgatac gcgagcgaac gtgaagcgac   3060
tgctgctgca aaacgtctgc gacctgagca acaacatgaa tggtcttcgg tttccgtgtt   3120
tcgtaaagtc tggaaacgcg gaagtcagcg ccctgcacca ttatgttccg gatctgcatc   3180
gcaggatgct gctggctacc ctgtggaaca cctacatctg tattaacgaa gcgctggcat   3240
```

```
tgaccctgag tgattttct  ctggtcccgc cgcatccata ccgccagttg tttaccctca   3300
caacgttcca gtaaccgggc atgttcatca tcagtaaccc gtatcgtgag catcctctct   3360
cgtttcatcg gtatcattac ccccatgaac agaaatcccc cttacacgga ggcatcagtg   3420
accaaacagg aaaaaaccgc ccttaacatg cccgcttta  tcagaagcca gacattaacg   3480
cttctggaga aactcaacga gctggacgcg gatgaacagg cagacatctg tgaatcgctt   3540
cacgaccacc tgatgagct  ttaccgcagc tgcctcgcgc gtttcggtga tgacggtgaa   3600
aacctctgac acatgcagct cccggagacg gtcacagctt gtctgtaagc ggatgccggg   3660
agcagacaag cccgtcaggg cgcgtcagcg ggtgttggcg ggtgtcgggg cgcagccatg   3720
acccagtcac gtagcgatag cggagtgtat actggcttaa ctatgcggca tcagagcaga   3780
ttgtactgag agtgcaccat atgcggtgtg aaataccgca cagatgcgta aggagaaaat   3840
accgcatcag gcgctcttcc gcttcctcgc tcactgactc gctgcgctcg gtcgttcggc   3900
tgcggcgagc ggtatcagct cactcaaagg cggtaatacg gttatccaca gaatcagggg   3960
ataacgcagg aaagaacatg tgagcaaaag gccagcaaaa ggccaggaac cgtaaaaagg   4020
ccgcgttgct ggcgtttttc cataggctcc gcccccctga cgagcatcac aaaaatcgac   4080
gctcaagtca gaggtggcga aacccgacag gactataaag ataccaggcg tttccccctg   4140
gaagctccct cgtgcgctct cctgttccga ccctgccgct taccggatac ctgtccgcct   4200
ttctcccttc gggaagcgtg gcgctttctc atagctcacg ctgtaggtat ctcagttcgg   4260
tgtaggtcgt tcgctccaag ctgggctgtg tgcacgaacc ccccgttcag cccgaccgct   4320
gcgccttatc cggtaactat cgtcttgagt ccaacccggt aagacacgac ttatcgccac   4380
tggcagcagc cactggtaac aggattagca gagcgaggta tgtaggcggt gctacagagt   4440
tcttgaagtg gtggcctaac tacggctaca ctagaaggac agtatttggt atctgcgctc   4500
tgctgaagcc agttaccttc ggaaaaagag ttggtagctc ttgatccggc aaacaaacca   4560
ccgctggtag cggtggtttt tttgtttgca agcagcagat tacgcgcaga aaaaaaggat   4620
ctcaagaaga tcctttgatc ttttctacgg ggtctgacgc tcagtggaac gaaaactcac   4680
gttaagggat tttggtcatg agattatcaa aaaggatctt cacctagatc cttttaaatt   4740
aaaaatgaag ttttaaatca atctaaagta tatatgagta aacttggtct gacagttacc   4800
aatgcttaat cagtgaggca cctatctcag cgatctgtct atttcgttca tccatagttg   4860
cctgactccc cgtcgtgtag ataactacga tacgggaggg cttaccatct ggccccagtg   4920
ctgcaatgat accgcgagac ccacgctcac cggctccaga tttatcagca ataaaccagc   4980
cagccggaag ggccgagcgc agaagtggtc ctgcaacttt atccgcctcc atccagtcta   5040
ttaattgttg ccgggaagct agagtaagta gttcgccagt taatagtttg cgcaacgttg   5100
ttgccattgc tgcaggcatc gtggtgtcac gctcgtcgtt tggtatggct tcattcagct   5160
ccggttccca acgatcaagg cgagttacat gatccccat  gttgtgcaaa aaagcggtta   5220
gctccttcgg tcctccgatc gttgtcagaa gtaagttggc cgcagtgtta tcactcatgg   5280
ttatggcagc actgcataat tctcttactg tcatgccatc cgtaagatgc ttttctgtga   5340
ctggtgagta ctcaaccaag tcattctgag aatagtgtat gcggcgaccg agttgctctt   5400
gcccggcgtc aacacgggat aataccgcgc cacatagcag aactttaaaa gtgctcatca   5460
ttggaaaacg ttcttcgggg cgaaaactct caaggatctt accgctgttg agatccagtt   5520
cgatgtaacc cactcgtgca cccaactgat cttcagcatc ttttactttc accagcgttt   5580
ctgggtgagc aaaaacagga aggcaaaatg ccgcaaaaaa gggaataagg gcgacacgga   5640
```

```
aatgttgaat actcatactc ttccttttc aatattattg aagcatttat cagggttatt    5700
gtctcatgag cggatacata tttgaatgta tttagaaaaa taaacaaata ggggttccgc    5760
gcacatttcc ccgaaaagtg ccacctgacg tctaagaaac cattattatc atgacattaa    5820
cctataaaaa taggcgtatc acgaggccct ttcgtc                              5856

<210> SEQ ID NO 2
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 2
gtatgagctc atggagaaaa taaagtgaac                                     30

<210> SEQ ID NO 3
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 3
gtatgagctc atggagaaaa taaaatgaac                                     30

<210> SEQ ID NO 4
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 4
gtatgagctc aaggagaaaa taaaatgaac                                     30

<210> SEQ ID NO 5
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 5
ccgttcgaat tattatttca gccccag                                        27

<210> SEQ ID NO 6
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 6
ccataaactg ccaggaattg g                                              21

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
gcttaccggg caatacactc                                                20
```

```
<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 8
ggtgaatggc agggaaaaac                                                   20

<210> SEQ ID NO 9
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 9
cgtcaacggt accgctgtaa ctg                                               23

<210> SEQ ID NO 10
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 10
gcctgaagtg agctcaatca atcc                                              24

<210> SEQ ID NO 11
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 11
gcaaaattgc ctctgggaaa gc                                                22

<210> SEQ ID NO 12
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 12
ccatgtgtcg gaggattgc                                                    19

<210> SEQ ID NO 13
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 13
cagtcatagc cgaatagcct                                                   20

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide
```

```
<400> SEQUENCE: 14
cggtgccctg aatgaactgc                                              20

<210> SEQ ID NO 15
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 15
gattatcgtc actgcaatgc ttcgc                                        25

<210> SEQ ID NO 16
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 16
gctgattaca ggaggtcata cg                                           22

<210> SEQ ID NO 17
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 17
gcctgaatca gtattgatct gc                                           22

<210> SEQ ID NO 18
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 18
cgcgtttaca tcacagagg                                               19

<210> SEQ ID NO 19
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 19
gctggtgcaa ctctgaaag                                               19

<210> SEQ ID NO 20
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 20
ccttgtttac gcctctgctg g                                            21
```

SYSTEM AND METHOD FOR DETECTING A SUBSTANCE IN LIQUID

RELATED APPLICATION

This application claims the benefit of priority from U.S. Provisional Patent Application No. 61/282,215 filed on Dec. 31, 2009, the contents of which are hereby incorporated by reference as if fully set forth herein.

FIELD AND BACKGROUND OF THE INVENTION

The present invention, in some embodiments thereof, relates to detection of a substance and, more particularly, but not exclusively, to a system and method for detecting a substance in liquid.

The development of miniaturized devices for chemical analysis and for synthesis and fluid manipulation is motivated by the prospects of improved efficiency, reduced cost and enhanced accuracy. Efficient, reliable manufacturing processes are a critical requirement for the cost-effective, high-volume production of devices that are targeted at high-volume, high-throughput test markets.

Microfluidic devices include components such as channels, reservoirs, mixers, pumps, valves, chambers, cavities, reaction chambers, heaters, fluidic interconnects, diffusers, nozzles, and other microfluidic components. These microfluidic components typically have dimensions which range between several micrometers to several millimeters. The small dimensions of such components minimize the physical size, the power consumption, the response time and the waste of a microfluidic device as compared to other technologies.

Several attempts have been made to incorporate biological materials as biosensors capable of sensing physical or chemical environmental conditions in microfluidic devices.

Generally, a biosensor is a device that qualifies and/or quantifies a physiological or biochemical signal. Biosensors have been developed to overcome some of the shortcomings of the classical agent detection techniques. Good biosensing systems are characterized by specificity, sensitivity, reliability, portability, ability to function even in optically opaque solutions, real-time analysis and simplicity of operation. Biosensors couple a biological component with an electronic transducer and thus enable conversion of a biochemical signal into a quantifiable electrical response.

The function of the biosensor depends on the biochemical specificity of the biologically active material. Enzymes, antibodies, aptamers, DNA, receptors, organelles and microorganisms as well as plant cells or tissues have been used as biological sensing elements. The most commonly used biological element in the construction of biosensors are enzymes, due to their high specific activities as well as high analytical specificity. Purified enzymes are, however, expensive and unstable, thus limiting their applications in the field of biosensors.

Following are technologies incorporating biosensors in microfluidic devices.

U.S. Pat. No. 6,436,698 is directed at automatic measurement of water toxicity, using luminescent microorganisms living in freshwater. Test samples are injected using a needle into multi-well plate containing the luminescent microorganisms and, after a lapse of certain times from the injection, luminosity is detected by a sensor.

U.S. Pat. No. 6,117,643 is directed at detection of pollutants, explosives and heavy-metals. A bioreporter, capable of metabolizing a particular substance to emit light, is placed in a selectively permeable container. When the light is emitted, an optical application specific integrated circuit generates an electrical signal which indicates the concentration of the substance.

U.S. Pat. No. 6,133,046 teaches the use of a fixed electrode and a moving electrode, whereby the surfaces of the electrodes bound a ligand of the agent to be detected (e.g., an antibody, whereby the agent is an antigen or a hapten, a receptor whereby the agent is a receptor, etc.). When a sample is placed between the electrodes, an electric signal is generated, depending on whether or not the agent is present.

U.S. Published Application No. 20080044844 discloses a device for detecting presence, absence or level of an analyte in a sample. The device includes a substrate configured for supporting a population of cells in an addressable manner so as to allow identification of each discrete subpopulation of cells. The surface of the substrate is fabricated with discrete microwells configured to enable holding the subpopulations of the cells. Microchannels provide fluid communication between the microwells and sample ports.

U.S. Published Application No. 200800448 discloses a population of cells comprising at least two subpopulations of cells, wherein a first subpopulation of the at least two subpopulation of cells includes a first reporter expression construct being expressible in a cell of the first subpopulation when exposed to a first analyte and whereas a second subpopulation of the at least two subpopulation of cells includes a second reporter expression construct being expressible in a cell of the second subpopulation when exposed to a second analyte.

Additional background art includes: U.S. Pat. Nos. 6,638,752, 6,638,483, 6,636,752, 6,632,619, 6,627,433, 6,630,353, 6,620,625, 6,544,729, 6,537,498, 6,521,188, 6,453,928, 6,448,064, 6,340,572, 6,377,721 and 5,922,537, Ben-Yoav et al., 2008, ECS Trans., Volume 16, Issue 11, Microfabrication and Microfluidics, pages 187-197, Vollmer et al. Applied and Environmental Microbiology 63(7) (1997) 2566-2571 and X. Xiaorong, M. E. Lidstrom, B. A. Parviz, J. Microelectromech. Syst. 16(2) (2007) 429-444.

SUMMARY OF THE INVENTION

According to an aspect of some embodiments of the present invention there is provided a system for analyzing a liquid. The system comprises an electrochemical unit having an electrochemical microchamber for receiving a sample of the liquid and electrochemically analyzing the sample. The system further comprises a microfluidic unit being attached to the electrochemical unit and having microchannels constituted for sampling the sample in situ and feeding the sample to the electrochemical microchamber.

According to some embodiments of the invention the microfluidic unit is configured for the sampling while the electrochemical unit and the microfluidic unit are both submerged in the liquid.

According to some embodiments of the invention the system further comprises a sealed encapsulation for sealing the electrochemical unit and the microfluidic unit except for an inlet port of the microfluidic unit.

According to some embodiments of the invention the microfluidic unit comprises an integrated pump for pumping the sample from the environment to the microchannels.

According to some embodiments of the invention the electrochemical unit comprises a plurality of microchambers.

According to some embodiments of the invention the microchamber comprises a planar working electrode on a base thereof.

According to some embodiments of the invention the microchamber comprises a working electrode on a base thereof, the working electrode being coated by a conductive polymer.

According to some embodiments of the invention the microchamber comprises a working electrode, generally shaped as a pillar projecting upwardly from a base of the microchamber.

According to some embodiments of the invention the microchamber comprises a working electrode, a reference electrode and a counter electrode on a base of the microchamber, and wherein a height of the working electrode above the base is at least 10 times or at least 20 times or at least 30 times higher than a height of any of the reference and the counter electrodes.

According to some embodiments of the invention the electrochemical unit comprises a biological sensor capable of producing electrochemical signal in the microchamber.

According to some embodiments of the invention the biological sensor comprises a cell having a nucleic acid expression construct which comprises a promoter sequence operatively linked to a reporter gene, wherein an activity/expression of the reporter gene is responsive to genotoxicants which induce DNA synthesis halt, multiple-target attacks on DNA and or DNA cross linking.

According to some embodiments of the invention the liquid is water and the electrochemical unit is configured for detecting water toxicity.

According to some embodiments of the invention the promoter sequence operatively linked to the reporter gene comprises a sulA:phoA fusion as set forth in SEQ ID NO: 1.

According to an aspect of some embodiments of the present invention there is provided a method of analyzing liquid. The method comprises submerging one of the systems described herein in the liquid and analyzing signals produced by the electrochemical unit.

According to an aspect of some embodiments of the present invention there is provided a method of manufacturing a system for analyzing a liquid. The method comprises forming a microchamber in a substrate and depositing electrodes on a base thereof thereby providing an electrochemical unit. The method further comprises forming a microfluidic unit having microchannels, and assembling the microfluidic unit and the electrochemical unit such as to establish fluid communication between the microchannels and the microchamber.

According to some embodiments of the invention the method further comprises encapsulating the system with a sealed encapsulation in a manner such that an inlet port of the microfluidic unit remains exposed to the environment.

According to an aspect of some embodiments of the present invention there is provided a nucleic acid expression construct comprising a sulA:phoA fusion as set forth in SEQ ID NO: 1.

According to an aspect of some embodiments of the present invention there is provided a cell comprising at least one of the nucleic acid constructs described herein. According to some embodiments of the present invention the cell is a prokaryotic cell.

According to an aspect of some embodiments of the present invention there is provided a method of detecting an analyte in a sample. The method comprises: (a) contacting the sample with a population of cells which comprise at least one of the cells described herein (e.g., a cell with a nucleic acid expression construct which comprises a sulA:phoA fusion as set forth in SEQ ID NO: 1), and (b) analyzing expression/activity of the reporter gene in the cells, wherein an upregulation of the activity/expression of the reporter gene upon contact with the sample is indicative of presence of the analyte in the sample.

According to an aspect of some embodiments of the present invention there is provided a system for detecting an analyte in a sample. The system comprises an electrochemical chamber having therein at least some of the cells described herein (e.g., a cell with a nucleic acid expression construct which comprises a sulA:phoA fusion as set forth in SEQ ID NO: 1). The system is configured for receiving the sample and generating an output signal responsively to electrochemical signals produced by the cells when contacted with the sample in the chamber.

According to some embodiments of the invention the output signal comprises an electrical signal, and the electrochemical chamber comprises electrodes for transmitting the electrical signal.

According to some embodiments of the invention the output signal comprises an optical signal, and the electrochemical chamber comprises a mechanism for converting the electrochemical signals to the optical signal.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic illustration of a system for analyzing a liquid, according to various exemplary embodiments of the present invention.

FIG. 2 is a flowchart diagram describing a method suitable for fabricating a system for analyzing a liquid, according to various exemplary embodiments of the present invention.

FIG. 3 is a flowchart diagram describing a process suitable for fabricating an electrochemical unit, according to some embodiments of the present invention.

FIG. 4 is a flowchart diagram describing a process suitable for fabricating a microfluidic unit, according to some embodiments of the present invention.

FIGS. 5A-C are images (FIGS. 5A and 5B) and a schematic illustration (FIG. 5C) of a prototype portable solid-state system fabricated during experiments performed according to some embodiments of the present invention. FIG. 5A shows a silicon based microchip which four differentially sized electrochemical microchambers, FIG. 5B shows an inside view of a single three-electrode electrochemical microchamber, and FIG. 5C illustrates a schematic layout of the system.

FIG. 6A is a schematic illustration of a layout of a measurement platform used in experiments performed according to some embodiments of the present invention. A system which comprises a PMMA seal, a microfluidic PDMS molding and an electrochemical microchip was mounted on the measurement platform.

FIG. 6B is an image of the system mounted on the measurement platform of FIG. 6A.

Figure 7C:
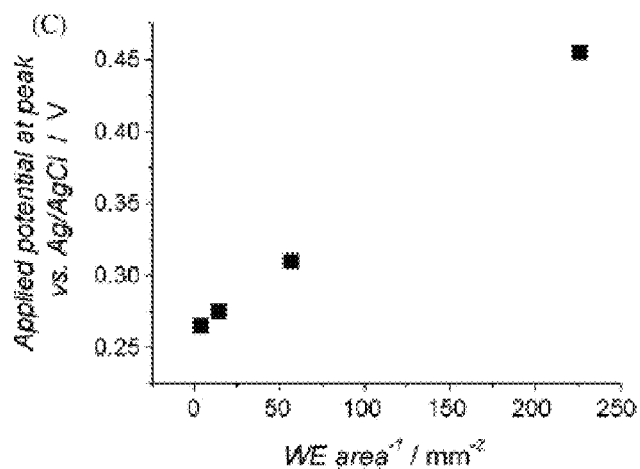

FIGS. 7A-C show results of electrical measurements performed using a system fabricated according to some embodiments of the present invention. FIG. EX36A shows cyclic voltammograms resulted by a $Fe^{2+}/Fe^{3+}$ assay with differently sized electrochemical micro-chambers, v=50 mV/s, FIG. EX36B shows the effect of the area of the working electrode on the anodic current peak, and FIG. EX36C shows the effect of the 1/area of the working electrode on the applied potential at the anodic peak.

Figure 8:
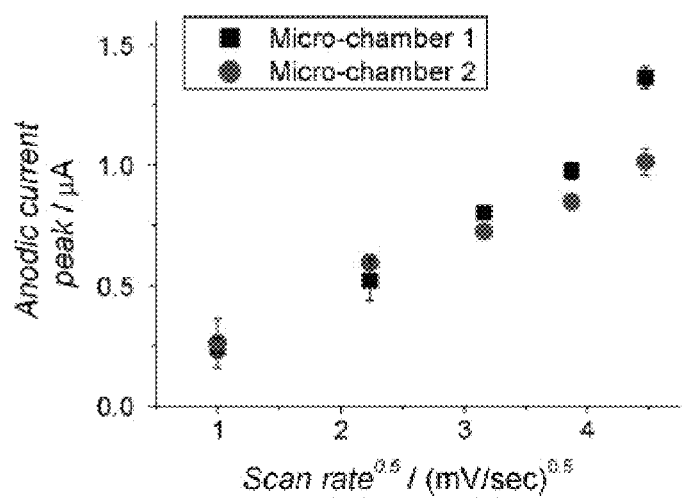

FIG. 8 shows the effect of the square root of the scan rate at a cyclic voltammetry assay on the peak of the anodic current in the presence of 0.4 mg/ml pAP, as measured in experiments performed according to some embodiments of the present invention for in two similar electrochemical microchambers.

FIG. 9 shows chrono-amperometry results for the response to different concentrations of pAP as measured in experiments performed according to some embodiments of the present invention.

FIG. 10A shows chrono-amperometric results of bacterial cells following 1 hr of incubation in the presence and the absence of NA, as measured in experiments performed according to some embodiments of the present invention.

FIG. 10B shows chrono-amperometric results of bacterial cells following increasing periods of induction time with NA, as measured in experiments performed according to some embodiments of the present invention.

Figure 10C:
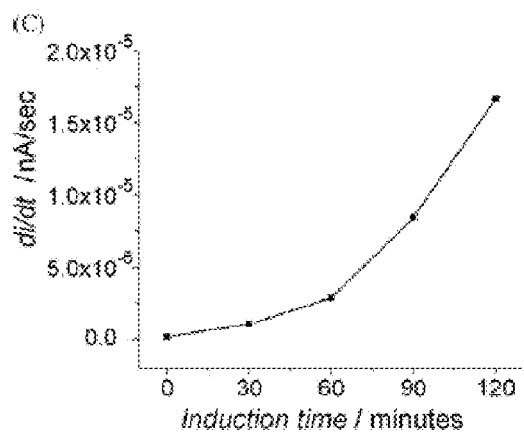

FIG. 10C shows the effect of the induction time with NA on the slope of the detected electrochemical current, as measured in experiments performed according to some embodiments of the present invention.

Figure 11A:
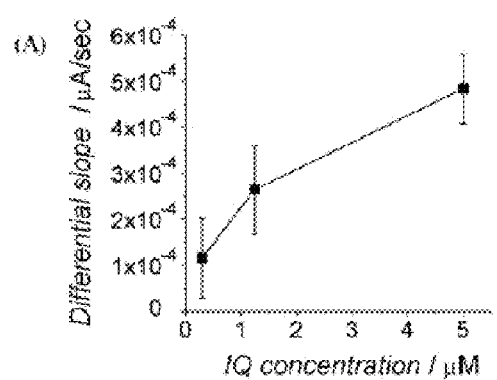
Figure 11B:
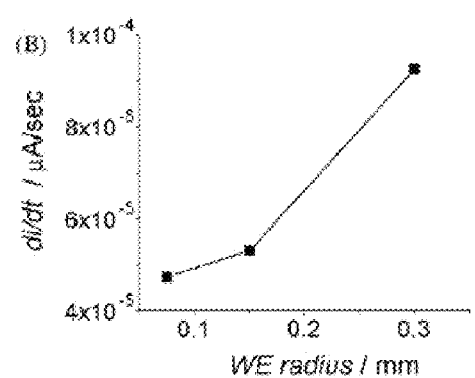

FIGS. 11A-B show the effect of the IQ concentration (FIG. EX36A) and the radius of the working electrode (FIG. EX36B) on the differential slope of the electrochemical current, as measured in experiments performed according to some embodiments of the present invention.

Figure 12:
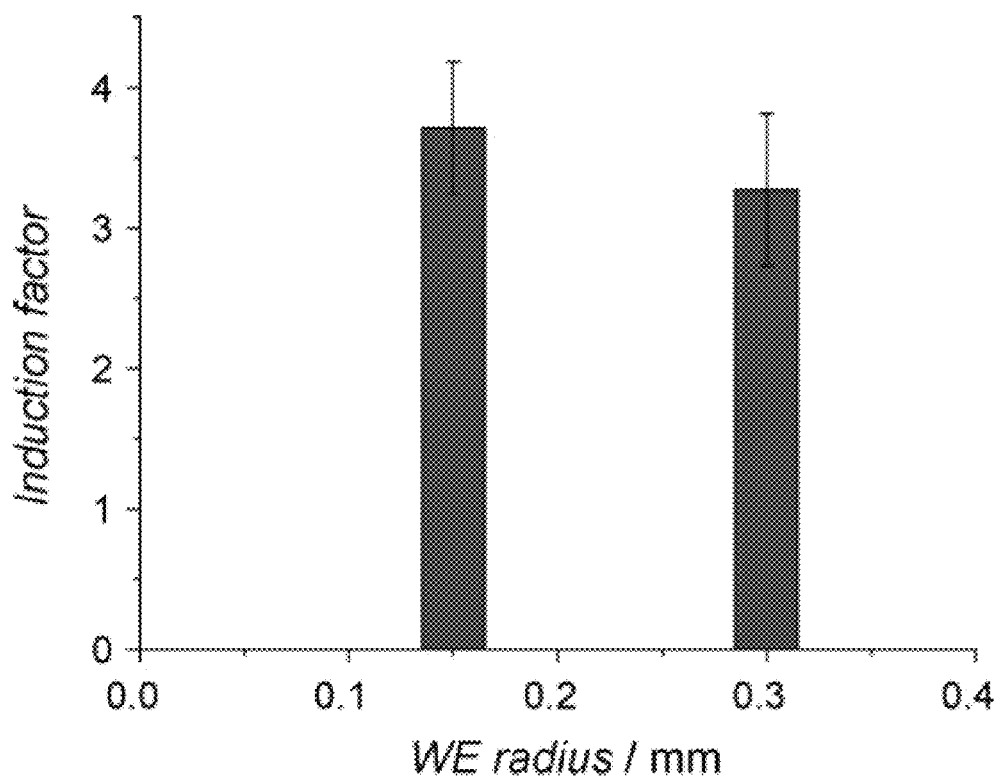

FIG. 12 shows induction factor values for two different size electrochemical microchambers as a function of the working electrode radius, as measured in experiments performed according to some embodiments of the present invention.

Figure 13:
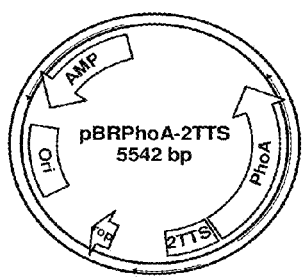

FIG. 13 is a schematic illustration of a pBRphoA structure, according to some embodiments of the present invention.

Figure 14:
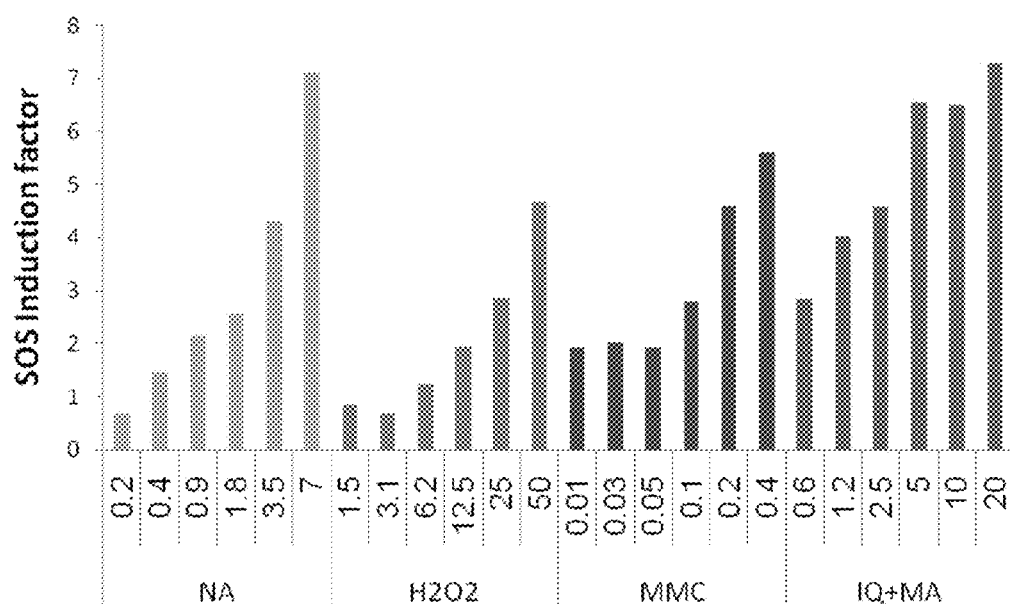

FIG. 14 E. coli reporter strain panel was exposed to several concentrations of NA (7, 3.5, 1.8, 0.9, 0.4, 0.2 mg/L), MMC (400, 200, 100, 50, 25, 12.5 µg/L), $H_2O_2$ (50, 25, 12.5, 6.3, 3.1, 1.6, 0.8 mg/L) and the pre-genotoxicant IQ (20, 10, 5, 2.5, 1.2, 0.6 mg/L) that was metabolicaly activated. The AP activity was measured electrochemically at potential 0.3 mV by making use of pAPP in a point assay after induction period. The determined SOS-induction factors for each concentration level are plotted against each other.

Figure 15:
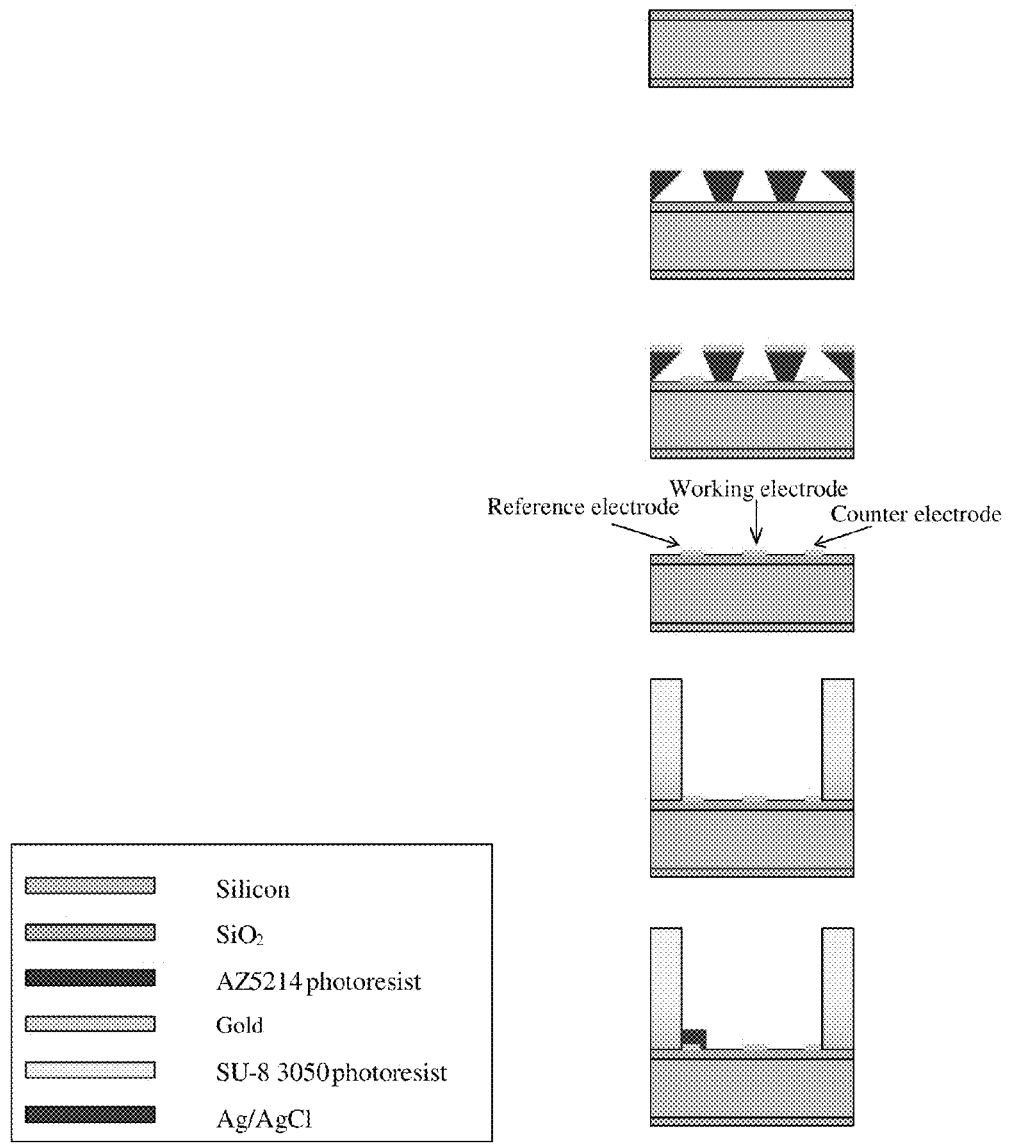

FIG. 15 is a schematic illustration of a process used according to some embodiments of the present invention for fabricating a silicon based electrochemical chip which can be used as an electrochemical unit in a system for analyzing a liquid.

FIGS. 16A-D show different brass molds used in accordance with some embodiments of the present invention for fabricating a PDMS microfluidic chip which can be used as a microfluidic in a system for analyzing a liquid.

FIGS. 17A-B show flow simulation results of Reynolds number in a single micro-fluidic channel (FIG. 17A), and flow velocity in a single micro-chamber (FIG. 17A), as obtained in computer simulations performed according to some embodiments of the present invention.

FIGS. 18A-D are schematic illustrations (FIGS. 18A and 18D) and images (FIGS. 18B and 18C) of a PMMA seal used for sealing a system for analyzing a liquid, according to some embodiments of the present invention. FIG. 18A illustrates a base and a cover of the seal, FIG. 18B shows different configurations of the seal, FIG. 18C shows needle integration with the microfluidic unit, and FIG. 18D illustrates the seal together with a microfluidic chip.

FIG. 19 is an image showing integrated microfluidic chip and electrochemical chip, fabricated according to some embodiments of the present invention.

FIGS. 20A-D are images (FIGS. 20A, 20B and 20D) and an illustration (FIG. 20C) showing experimental system used in experiments performed according to some embodiments of the present invention.

FIGS. 21A-B are a schematic illustration (FIG. 21A) and an image (FIG. 21B) of an experimental system used according to some embodiments of the present invention in experiments which tested the ability of a system for analyzing a liquid to infuse a liquid sample into the electrochemical chip while being submerged in the liquid.

FIGS. 22A-D are schematic illustrations of a three-parts microfluidic PDMS chip which can be used as a microfluidic unit in system for analyzing a liquid, according to some embodiments of the present invention. FIG. 22A illustrates the layout of the microfluidic chip, and FIGS. 22A-D illustrate a sampling member (FIG. 22A), an analysis part (FIG. 22B) and a pipetting part (FIG. 22C) of the microfluidic chip.

FIG. 23 is an image showing several polymeric molds which used in experiments performed according to some embodiments of the present invention for fabricating microfluidic chips.

Figure 24:
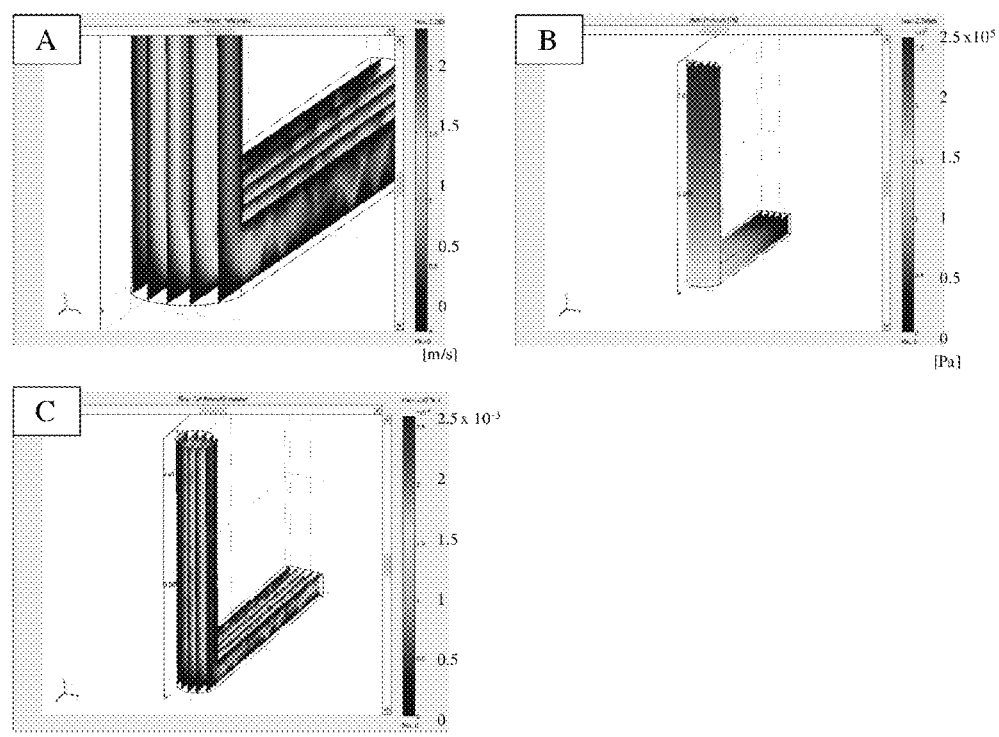

FIGS. 24A-C show flow simulation results as obtained in computer simulations performed according to some embodiments of the present invention for testing flow characteristics of a three-part microfluidic chip. FIG. 24A shows flow velocity, FIG. 24b shows pressure, and FIG. 24C shows calculated Reynolds number.

Figure 25:
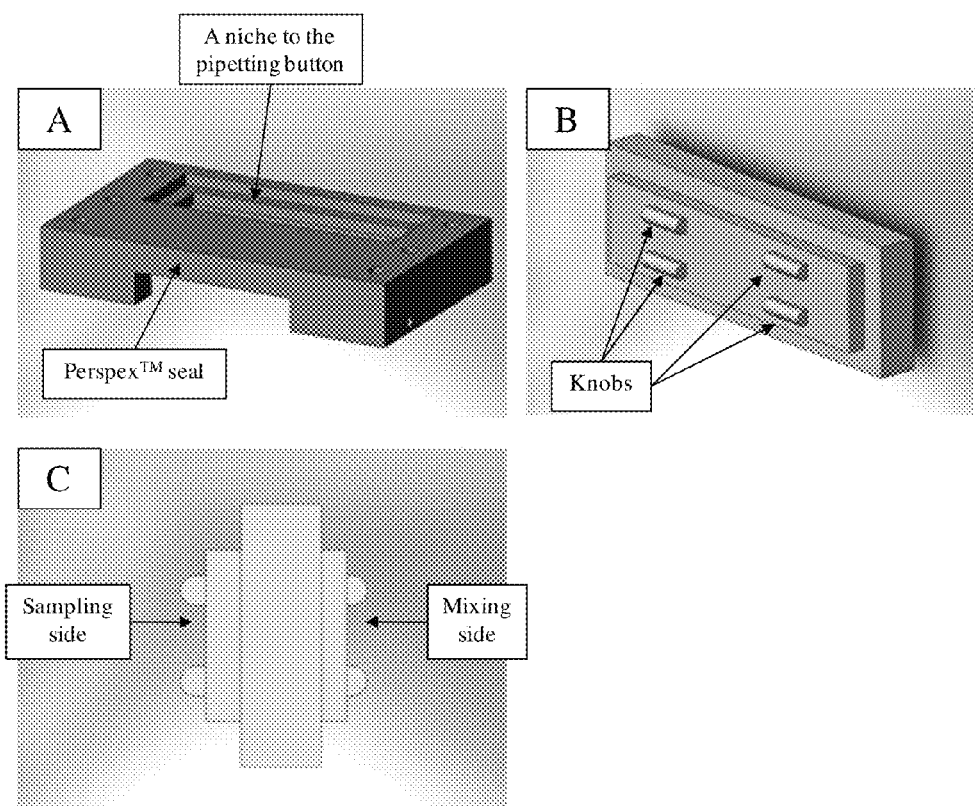

FIGS. 25A-C are schematic illustrations of a PMMA seal used according to some embodiments of the present invention in a system having a a three-part microfluidic chip. FIG. 25A shows the seal, FIG. 25B shows a pipetting button, and FIG. 25C shows a side view of the pipetting button describing the mixing and the sampling sides.

Figure 26:
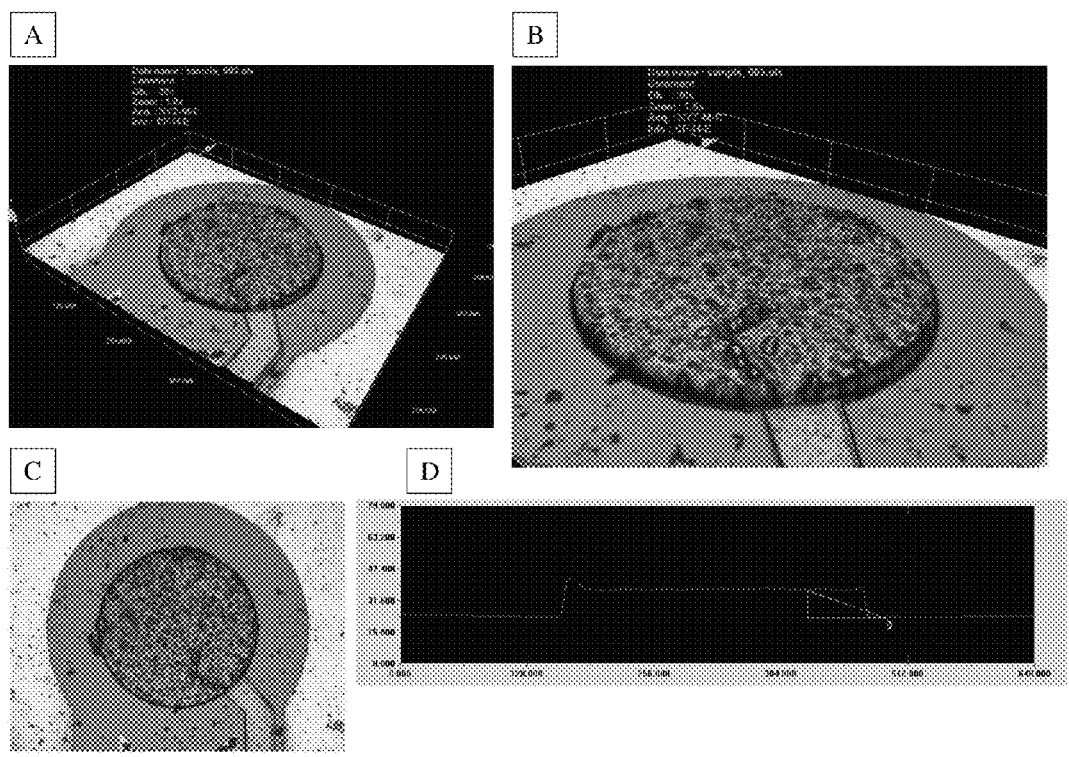

FIGS. 26A-D show confocal scanning laser microscopy (CSLM, X20 objective, LEXT OLS3100, Olympus) analysis of a pillar electrode, fabricated according to some embodiments of the present invention. FIGS. 26A and 26B are 3D reconstruction images, FIG. 26C is a 2D X-Y top image, and FIG. 26D shows an X-Z analysis of the electrode thickness. The electrode dimensions were 150 µm in radius and 13.5 µm in thickness.

Figure 27:
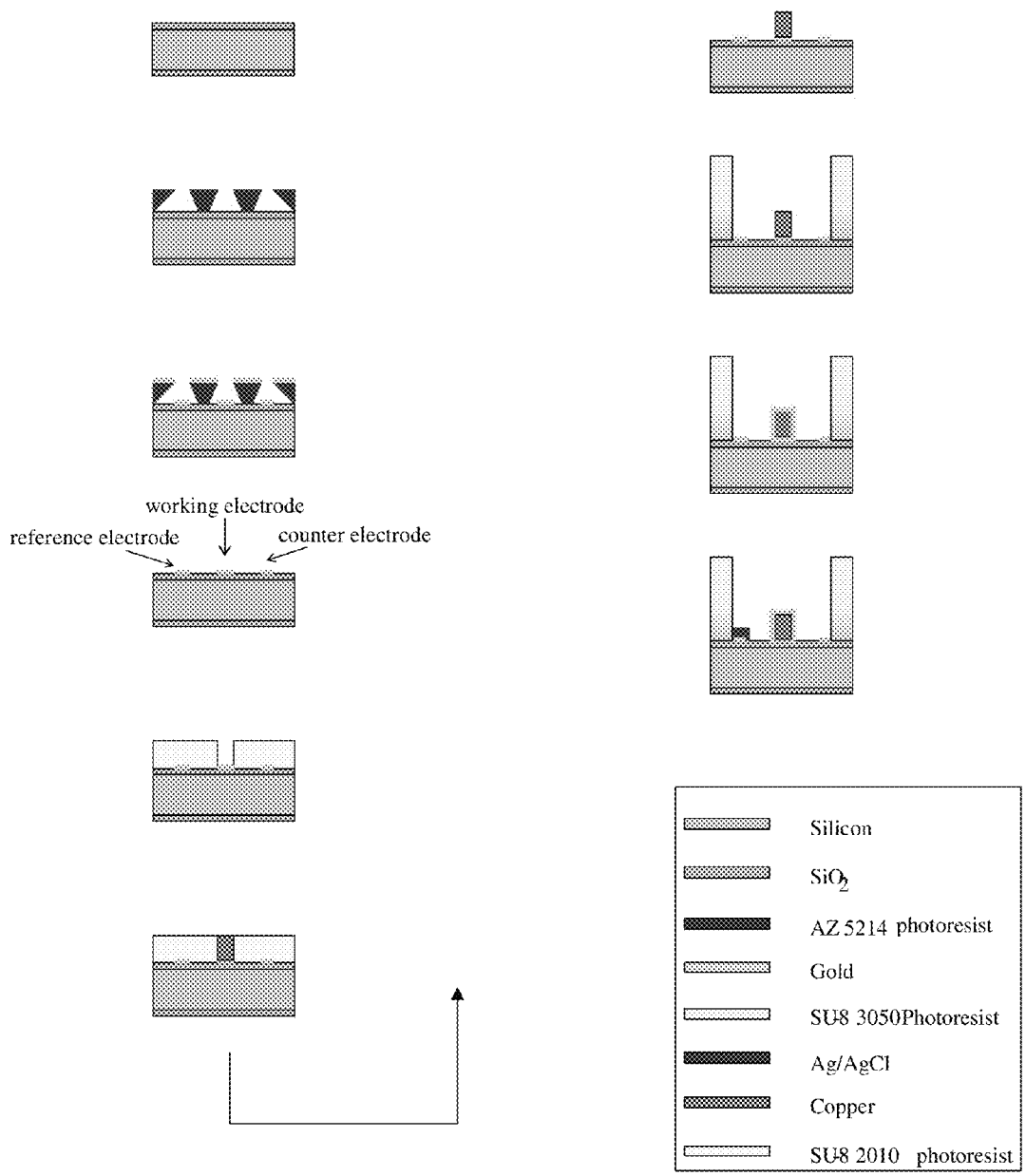

FIG. 27 is a schematic illustration of a process used according to some embodiments of the present invention for fabricating the pillar electrode shown in FIGS. 26A-D.

FIG. 28 shows a metal conductor mask used in a lithography process performed according to some embodiments of the present invention.

FIGS. 29A-B show a layout of a single microchip of the mask of FIG. 28.

Figure 30:
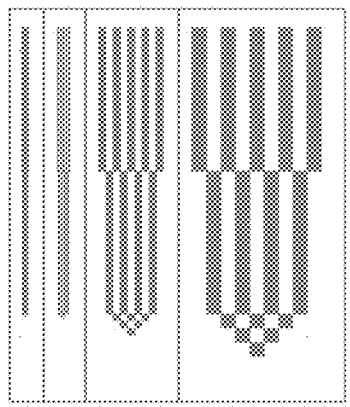

FIG. 30 shows process validation marks of the mask of FIG. 28.

Figure 31:
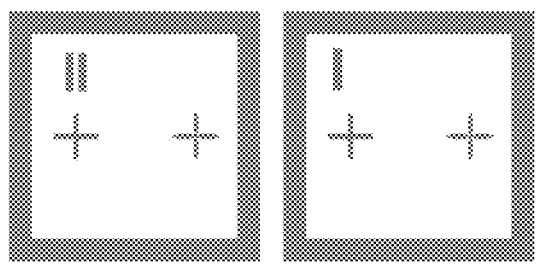

FIG. 31 shows alignment marks of the mask of FIG. 28.

Figure 32:
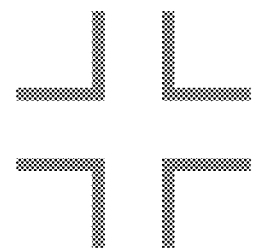

FIG. 32 show dicing marks of the mask of FIG. 28.

Figure 33:
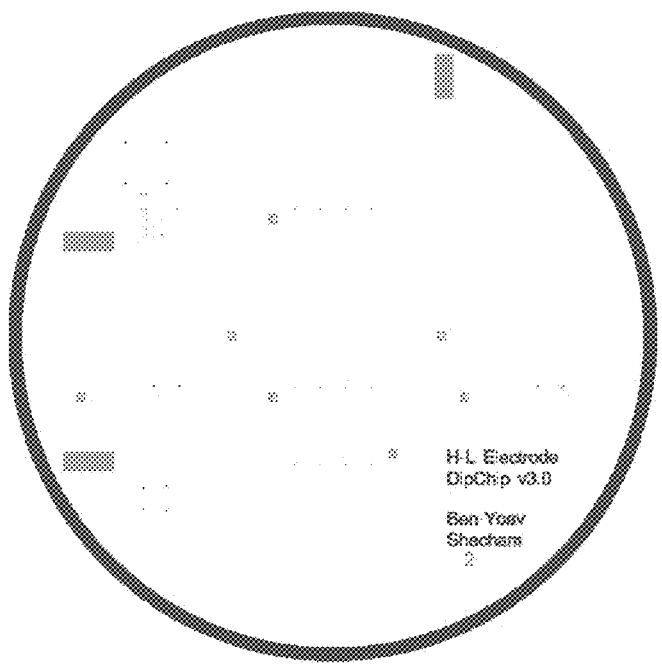

FIG. 33 shows a working electrode electroplating mask used in a lithography process performed according to some embodiments of the present invention.

Figure 34:
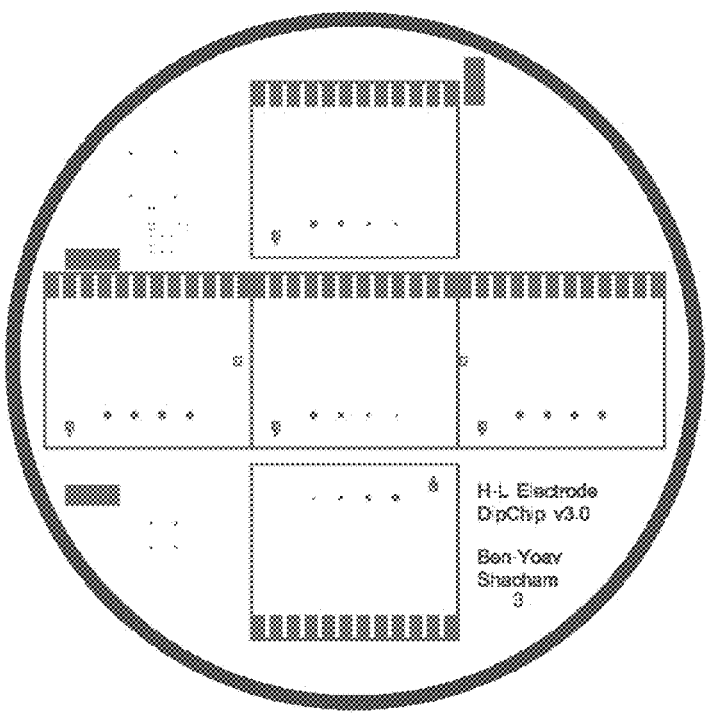

FIG. 34 shows a microchamber mask used in a process performed according to some embodiments of the present invention.

Figure 35:
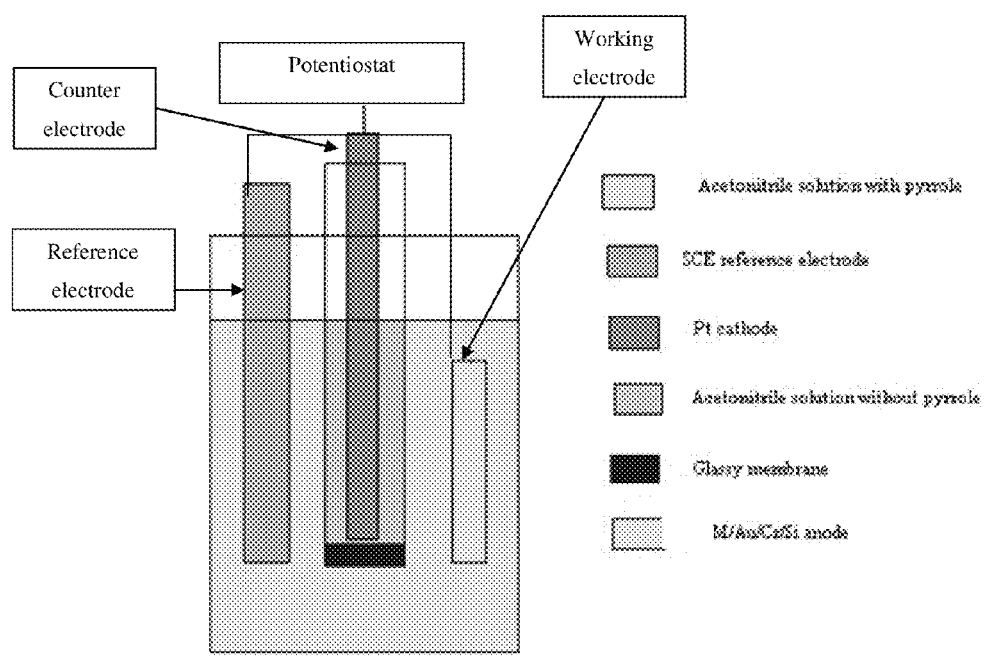

FIG. 35 is a schematic illustration of a Polypyrrole electropolymerization bath used in experiments performed according to some embodiments of the present invention.

Figure 36A:
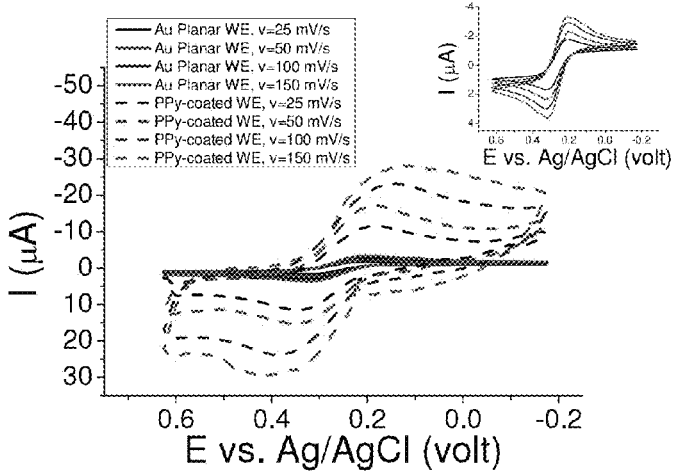
Figure 36B:
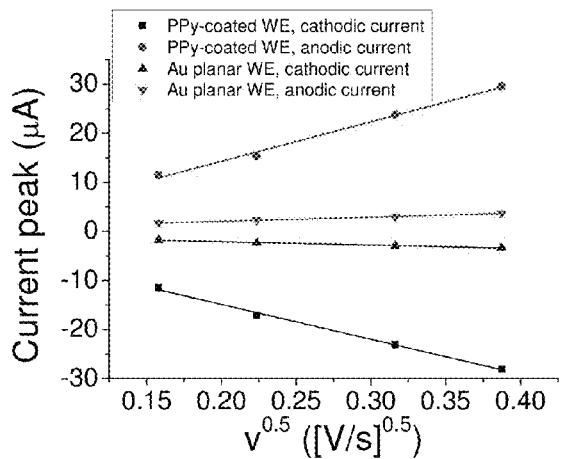
Figure 36C:
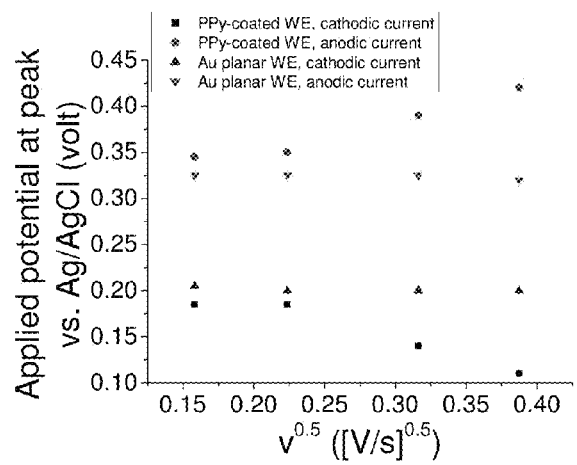

FIGS. 36A-C show results of electrical measurements performed using a system having a PPy-coated (dashed curves) and a gold planar (solid curves) working electrode, as obtained in experiments performed according to some embodiments of the present invention. FIG. 36A shows cyclic voltammograms resulted by a Ferrocyanide/Ferricyanide assay, FIG. 36B shows the effect of the square root of the scan rate at a cyclic voltammetry assay on the resulted peak of the anodic and the cathodic current, and FIG. 36C shows the effect of the square root of the scan rate at a cyclic voltammetry assay on the resulted peak of the anodic and the cathodic potential.

Figure 37A:
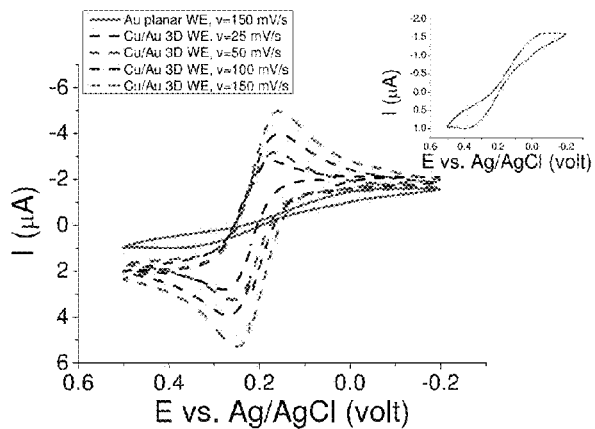
Figure 37B:
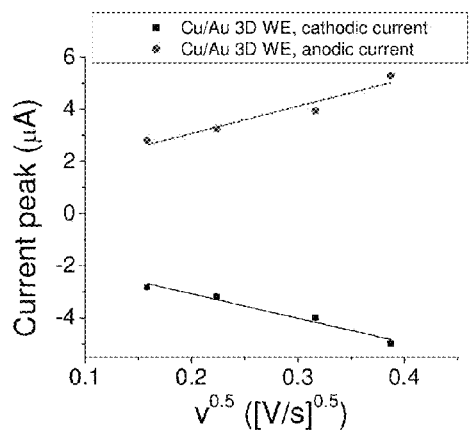
Figure 37C:
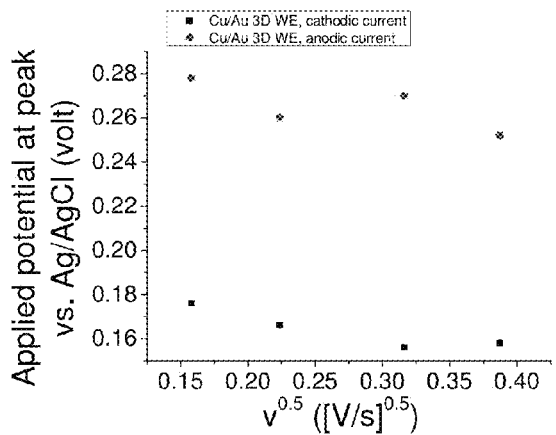

FIGS. 37A-C show results of electrical measurements performed using a system having a pillar electrode fabricated according to some embodiments of the present invention. FIG. 37A shows cyclic voltammograms resulted by a Ferrocyanide/Ferricyanide assay at different scan rates, FIG. 37B shows the effect of the square root of the scan rate at a cyclic voltammetry assay on the resulted peak of the anodic and the cathodic current, and FIG. 37C shows effect of the square root of the scan rate at a cyclic voltammetry assay on the resulted peak of the anodic and the cathodic potential.

Figure 38A:
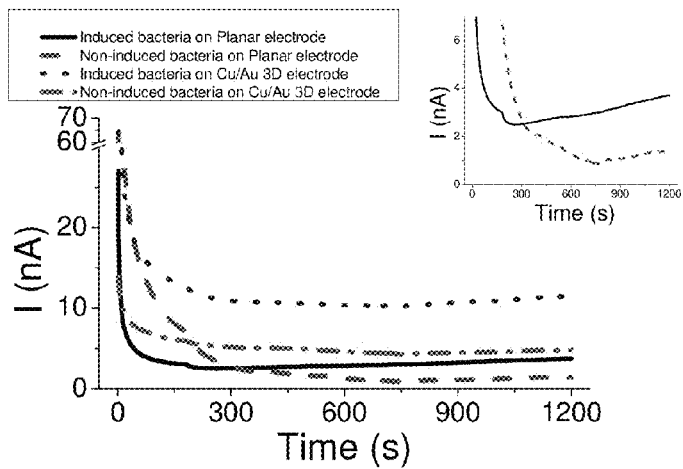
Figure 38B:
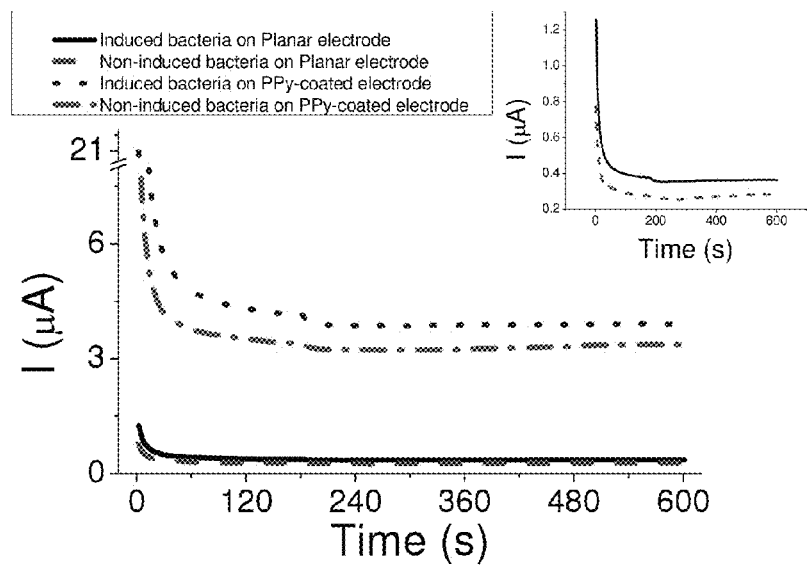

FIGS. 38A-B show chrono-amperometric results of bacterial cells in the presence and the absence of 5 ppm NA on a pillar electrode (FIG. 38A) and a PPy-coated electrode (FIG. 38B) fabricated according to some embodiments of the present invention. The insets show inside views.

Figure 39:
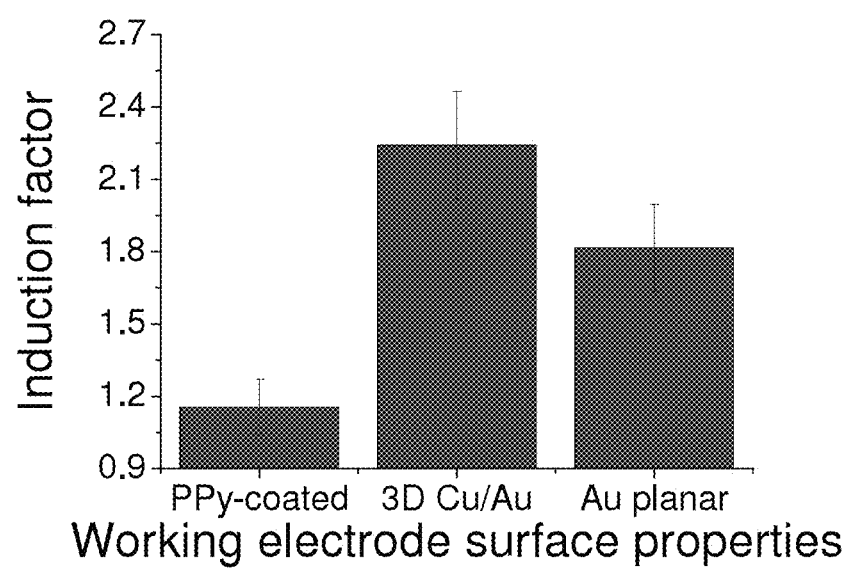

FIG. 39 shows a comparison between induction factor values for different types of working electrodes, fabricated according to some embodiments of the present invention.

DESCRIPTION OF SPECIFIC EMBODIMENTS OF THE INVENTION

The present invention, in some embodiments thereof, relates to detection of a substance and, more particularly, but not exclusively, to a system and method for detecting a substance in liquid.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
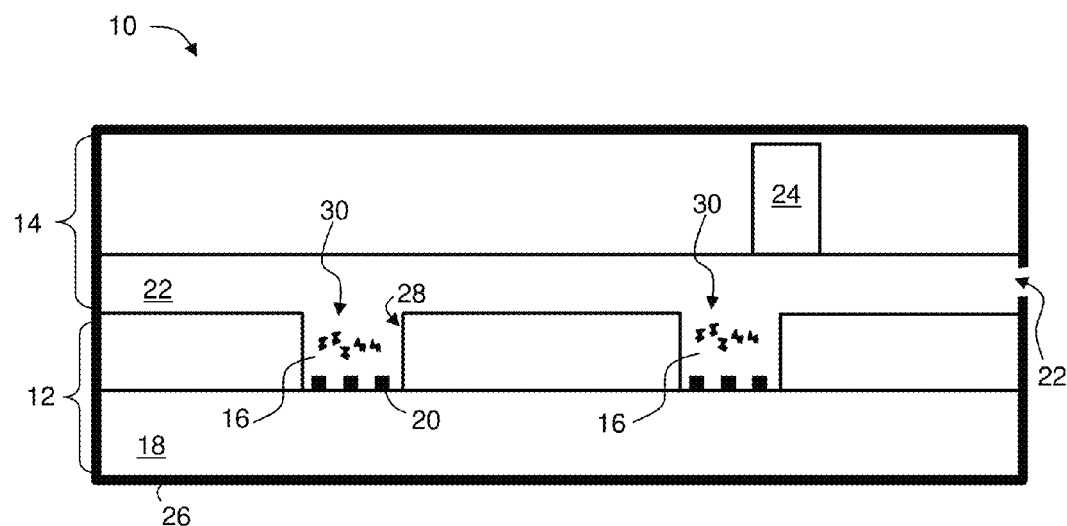

Referring now to the drawings, FIG. 1 illustrates a system 10 for analyzing a liquid, according to various exemplary embodiments of the present invention. The liquid can be of any type. In some embodiments of the present invention the liquid is or comprises water and system 10 analyzes the liquid for determining, for example, water toxicity.

System 10 comprises an electrochemical unit 12 and a microfluidic unit 14. Electrochemical unit 12 has one or more electrochemical microchambers 16 formed on a substrate 18 which is preferably a generally planar substrate, e.g., a silicon wafer or the like. Each of the microchambers 16 comprises a plurality of electrodes 20. For example, a microchamber can comprise a working electrode, a counter electrode and a reference electrode.

Electrochemical unit 12 can be fabricated using any known microelectronic fabrication technique, particularly, but not exclusively, processes suitable for microelectromechanical systems (MEMS). The fabrication process can be a subtractive process, an additive process or a combined process which includes a combination of subtractive steps and additive steps. Thus, the fabrication process includes at least one of: photolithography, evaporation, deposition, etching (using either wet chemical processes or plasma processes), focused ion milling, and lift off. A representative example of process suitable for fabricating unit 12 is provided in the Examples section that follows.

The walls 28 of microchambers 16 can be made of any material suitable for microelectronic applications, such as, but not limited to, a photoresist material or the like, that can be spun onto substrate 18. A representative example of a photoresist material suitable for the present embodiments includes, without limitation, SU-8 (e.g., SU-8 3050) that is currently manufactured and sold by MicroChem Corporation.

Electrodes 20 are preferably made, at least in part from a metal or a metal alloy, such as, but not limited to, gold, silver, copper and any combination thereof. Coated and modified electrodes are also contemplated. The reference electrode is optionally and preferably coated by a combination of materials selected from the group consisting of silver/silver chloride, silver/silver bromide, silver/silver fluoride, and silver/silver iodide, copper/copper halide, copper/copper oxide, copper/copper sulfate and the like, as known in the art. In some embodiments of the present invention, the working electrode is coated by a conductive polymer, such as, but not limited to, polypyrrole, polyaniline, polythiophene and polyacetylene.

The electrodes can be planar or they can have any other geometrical shape.

A "planar electrode," as used herein, refers to an electrode which projects upwardly from a base of the microchamber, by less than one micron or less than 500 nm or less than 400 nm.

In some embodiments, each microchamber comprises at least one or at least two or at least three planar electrodes. A representative example includes a configuration in which the microchamber has a planar working electrode, a planar counter electrode and a planar reference electrode. Typically, but not necessarily, the height of the planar reference electrode is higher by about 500 nm than the heights of the planar working electrode and the planar counter electrode. Thus, for example, the planar reference electrode can has a height of about 800 nm, and each of the planar working electrode and the planar counter electrode can has a height of about 300 nm.

In some embodiments, the working electrode is generally shaped as a pillar projecting upwardly from the base of microchamber. These embodiments are particularly useful when it is desired to increase the sensing area of the working electrode. In some embodiments of the present invention the height of working electrode above the base is at least 10 times higher than the heights of the electrodes.

Microfluidic unit 14 is attached to electrochemical unit 12 and has one or more microchannels 22 constituted for sampling the liquid in situ, for example, via an inlet port 24, and feeding the sampled liquid to the electrochemical microchamber(s) 16. Microchannels 16 can be separated or they can form a network of microchannels wherein there is a fluid communication among two or more of the microchannels. The sampled liquid enters the microchamber(s) 16 and is electrochemically analyzed by receiving electrical signals from the liquid via electrodes 20 and analyzing the signals. The signals can be transmitted through electrical communication lines to an analysis unit (not shown).

A variety of materials and processes, according to certain embodiments of the invention, can be used to form microfluidic unit 14. In some cases, the various materials selected lend themselves to various methods. For example, various components of the invention can be formed from solid materials, in which the microchannels can be formed via molding, micromachining, film deposition processes such as spin coating and chemical vapor deposition, laser fabrication, photolithographic techniques, etching methods including wet chemical or plasma processes, and the like. Also contemplated are three-dimensional freeform fabrication techniques, such as three-dimensional jet printing, wherein patterns of printed material allow directional fluid transport.

At least a portion of microfluidic unit 14 can be formed of a polymer, for example, an elastomeric polymer such as polydimethylsiloxane (PDMS), polytetrafluoroethylene (PTFE) or the like. A portion of microfluidic unit 14 can also be formed of silicone by molding a silicone chip. Technologies for precise and efficient formation of microfluidic systems from such materials are known.

Microfluidic unit 14, or components thereof can be conveniently formed of a hardenable fluid, facilitating formation via molding (e.g., replica molding, injection molding, cast molding, etc.). The hardenable liquid can be essentially any liquid that can be induced to solidify, or that spontaneously solidifies, into a solid capable of containing and/or transporting fluids contemplated for use in and with a microfluidic system. In one embodiment, the hardenable liquid comprises a polymeric liquid or a liquid polymeric precursor. Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

In various exemplary embodiments of the invention silicone polymers are used. A representative example includes the silicone elastomer PDMS, which is commercially available, e.g., from Dow Chemical Co., Midland, Mich. Silicone polymers including PDMS have several beneficial properties simplifying formation of microfluidic unit 14. For instance, such materials are inexpensive, readily available, and can be solidified from a liquid polymeric precursor via curing with heat. PDMSs are typically curable by exposure of the liquid polymeric precursor to temperatures of about 70° C. for exposure times of about an hour. Elastomeric polymer materials are also advantageous for their inertness to critical components of an analysis or synthesis to be carried out. Elastomeric polymer materials can also be coated with suitable materials as known in the art.

Other types of materials for microfluidic unit 14 are not excluded from the scope of the present invention. Suitable materials are generally selected based upon their compatibility with the manufacturing process (injection molding, dry etching, embossing, bonding, soft lithography, stereolithography and three-dimensional jet printing, etc.) and the conditions present in the particular operation to be performed by the microfluidic system. Such conditions can include extremes of pH, pressure within the microchannels, temperature, ionic concentration, and the like.

In various exemplary embodiments of the invention microfluidic unit 14 is configured for sampling the liquid while both electrochemical unit 12 and microfluidic unit 14 are submerged in the liquid. In these embodiments, system 10 optionally and preferably includes a sealed encapsulation 26 which seals electrochemical unit 12 and microfluidic unit 14, except for inlet port. In some embodiments of the invention microfluidic unit 14 comprises an integrated pump 24 for pumping sample from the environment into microchannels 22.

In various exemplary embodiments of the invention electrochemical unit 12 comprises a biological sensor 30 which produces an electrochemical signal in microchamber 16. Biological sensor preferably generates a signal in response to presence of a particular substance or a particular family or group of substances or some particular substances or families or groups of substances in the liquid.

According to an embodiment of the present invention, the biological sensor comprises a cell capable of reporter expression when the cell is exposed to an analyte of interest.

The regulation of expression can be at the polypeptide level. That is the analyte upregulates or downregulates the inherent activity of the reporter polypeptide. According to a specific embodiment, the analyte up-regulates the activity of the reporter polypeptide. Alternatively, the analyte can regulate the activity of a cis-acting transcriptional control element which regulates the expression of the reporter polypeptide. According to a specific embodiment, the analyte upregulates the expression of the reporter polypeptide.

As used herein the term "cell" (or cells), refers to prokaryotic or eukaryotic cell which can be genetically modified (in a transient or stable manner) to express exogenous polynucleotides such as a reporter polypeptide.

Examples of prokaryotic cells which can be used in accordance with the invention include but are not limited to bacterial cells, such as *Pseudomonas, Bacillus, Bacteriodes, Vibrio, Yersinia, Clostridium, Mycobacterium, Mycoplasma, Coryynebacterium, Escherichia, Salmonella, Shigella, Rhodococcus, Methanococcus, Micrococcus, Arthrobacter, Listeria, Klebsiella, Aeromonas, Streptomyces* and *Xanthomonas*.

Examples of eukaryotic cells which can be used in accordance with the invention include but are not limited to cell-lines, primary cultures or permanent cell cultures of fungal cells such as Aspergillus niger and Ustilago maydis [Regenfelder, E. et al. (1997) EMBO J. 16:1934-1942], yeast cells (see U.S. Pat. Nos. 5,691,188, 5,482,835 and Example 5 of the Examples section which follows), such as *Saccharomyces, Pichia, Zygosaccharomyces, Trichoderma, Candida*, and *Hansenula*, plant cells, insect cells, nematoda cells such as c. elegans, invertebrate cells, vetebrate cells and mammalian cells such as fibroblasts, epithelial cells, endothelial cells, lymphoid cells, neuronal cells and the like. Cells are commercially available from the American Type Culture Co. (Rockville, Md.).

According to a specific embodiment the cells comprise an exogenous reporter polynucleotide, which expresses a detectable reporter molecule when the cell is exposed to a fluid comprising the analyte.

According to a specific embodiment, reporter expression is detected electrochemically.

According to a specific embodiment, the reporter polynucleotide is comprised in a reporter expression construct. The construct may be episomal or alternatively integrated into the genome of the cell, as further described hereinbelow.

As used herein "reporter expression construct" refers to a vector which includes the polynucleotide sequence encoding the reporter. The reporter expression construct of the invention can be designed to randomly integrate into the genome of the cell, such that expression of the reporter polypeptide is governed by an endogenous regulatory element which is inducible by an analyte.

According to an embodiment of the invention, the polynucleotide sequence is positioned in the construct under the transcriptional control of at least one cis-regulatory element suitable for directing transcription in the cell upon exposure to an analyte.

As used herein a "cis acting regulatory element" refers to a naturally occurring or artificial polynucleotide sequence, which binds a trans acting regulator and regulates the transcription of a coding sequence located down-stream thereto. For example, a transcriptional regulatory element can be at least a part of a promoter sequence which is activated and/or repressed by a specific transcriptional regulator or it can be an enhancer which can be adjacent or distant to a promoter sequence and which functions in up regulating the transcription therefrom.

It will be appreciated that the cis-acting regulatory element of this aspect of the present invention may be stress regulated (e.g., stress-regulated promoter), which is essentially activated in response to cellular stress produced by exposure of the cell to, for example, chemicals, environmental pollutants, heavy metals, changes in temperature, changes in pH, as well as agents producing oxidative damage, DNA damage, anaerobiosis, and changes in nitrate availability or pathogenesis.

Examples of promoters which are preferably used in accordance with this aspect of the present invention include, but are not limited to, MipA, LacZ, GrpE, Fiu, MalPQ, oraA, nhoA, otsAB and yciD, KatG, nblA, glnA, phoA, micF, fabA, ars, cupl, cad, pbr, mer, umuDC, polB, sulA (sfiA), recN, recA, Cda, alkA, alkB, nrdA, and uvrA. Detailed description of such promoters is provided in WO2005/069738, which is hereby incorporated by reference in its entirety.

A cis acting regulatory element can also be a translational regulatory sequence element in which case such a sequence can bind a translational regulator, which up regulates translation.

The term "expression" refers to the biosynthesis of a gene product (i.e., RNA or polypeptide product). For example, in the case of the reporter polypeptide, expression involves the transcription of the reporter gene into messenger RNA (mRNA) and the translation of the mRNA into one or more polypeptides.

As used herein "reporter polypeptide" refers to a polypeptide gene product, which can be quantitated either directly or indirectly. As mentioned, the activity of the reporter polypeptide can be regulated by the analyte. The reporter polypeptide can be a wild type polypeptide or can be (genetically) modified to acquire a regulatable phenotype. For example, a reporter polypeptide can be an enzyme which when in the presence of a suitable substrate generates chromogenic products. Such enzymes include but are not limited to alkaline phosphatase, β-galactosidase, β-D-glucoronidase (GUS), luciferase and the like. U.S. Pat. No. 6,329,160 teaches specific fragments of luciferase useful as reporter polypeptides.

As used herein the term "analyte" refers to a molecule or a mixture of molecules in a liquid. It will be appreciated that molecules can be completely soluble in a liquid medium, alternatively they may be in a colloidal state. Thus analytes in liquid medium may be in solution or carried by the liquid medium.

Examples of analytes include, but are not limited to, small molecules such as naturally occurring compounds (e.g., compounds derived from plant extracts, microbial broths, and the like) or synthetic compounds having molecular weights of less than about 10,000 daltons, preferably less than about 5,000 daltons, and most preferably less than about 1,500 daltons, electrolytes, metals, peptides, nucleotides, saccharides, fatty acids, steroids and the like. Analytes typically include at least one functional group necessary for biological interactions (e.g., amine group, carbonyl group, hydroxyl group, carboxyl group).

According to a specific embodiment, the analyte is a genotoxic agents i.e., a genotoxicant.

As used herein, the term "genotoxicant" refers to a chemical, physical or biological agent that damages the DNA of a cell.

The genotoxicant may cause damage which is manifested by halting of DNA synthesis (e.g., antibiotic e.g., nalidixic acid (NA)), DNA cross-linking, DNA breaks and the like.

A non-limiting list of genotoxicants is provided infra.

According to a specific embodiment, the genotoxicant is mitomycin C.

According to a specific embodiment, the genotoxicant is $H_2O_2$.

According to a specific embodiment, the genotoxicant is nalidixic acid.

According to a specific embodiment, the genotoxic agent is a chemotherapy.

Genotoxic chemotherapy may be divided into alkylating agents (i.e., drugs that modify the bases of DNA, interfering with DNA replication and transcription and leading to mutations); intercalating agents (i.e., drugs that wedge themselves into the spaces between the nucleotides in the DNA double helix. They interfere with transcription, replication and induce mutations); and enzyme inhibitors (i.e., drugs that inhibit key enzymes, such as topoisomerases, involved in DNA replication inducing DNA damage).

The goal of treatment with any of these agents is the induction of DNA damage in the cancer cells. DNA damage, if severe enough, will induce cells to undergo apoptosis, the equivalent of cellular suicide. The genotoxic chemotherapy drugs affect both normal and cancerous cells. The selectivity of the drug action is based on the sensitivity of rapidly dividing cells, such as cancer cells, to treatments that damage DNA. The mode of action also explains many of the side effects of treatment with these drugs. Rapidly dividing cells, such as those that line the intestine or the stem cells in bone marrow, are often killed along with the cancer cells. In addition to being cytotoxic (cell poisons), these drugs are also mutagenic (cause mutations) and carcinogenic (cause cancer). Treatment with these drugs carries with it the risk of secondary cancers, such as leukemia. These drugs are used to treat a variety of solid cancers and cancers of blood cells, often in combination with other drugs. Specific examples of chemotherapeutic genotoxicants include, but are not limited to, Busulfan, Bendamustine, Carboplatin, Carmustine, Error! Hyperlink reference not valid., Cisplatin, Cyclophosphamide, Dacarbazine, Daunorubicin, Decitabine, Doxorubicin, Epirubicin, Etoposide, Idarubicin, Ifosfamide, Irinotecan, Lomustine, Mechlorethamine, Melphalan, Mitomycin C, Mitoxantrone, Oxaliplatin, Temozolomide and Topotecan.

While further reducing the present invention to practice, the present inventors have devised nucleic acid constructs and bacterial strains (further described in the Examples section which follows, and in FIGS. 10-14) which are reporter constructs and strains useful for reporting the presence of genotoxicants.

Thus, the instant specification also relate to a nucleic acid construct which comprises a promoter sequence operatively linked to a reporter gene, wherein an activity/expression of said reporter gene is responsive to genotoxicants which induce DNA synthesis halt, multiple-target attacks on DNA and or DNA cross linking.

The present invention further contemplates a genotoxicant sensing cell comprising a nucleic acid expression construct which comprises a promoter sequence operatively linked to a reporter gene, wherein an activity/expression of said reporter gene is responsive to genotoxicants which induce DNA synthesis halt, multiple-target attacks on DNA and/or DNA cross linking According to a specific embodiment, the cell is a prokaryotic cell.

According to a specific embodiment, the reporter gene is selected from the group consisting of alkaline phosphatase and beta galactosidase.

According to a specific embodiment, the genotoxicant is nalidixic acid, the cell is a bacterial cell (e.g., *E. coli*) and the exogenous polynucleotide comprises sulA:phoA as set forth in SEQ ID NO: 1. According to another specific embodiment, the genotoxicant is 2-Amino-3-methylimidazo[4,5-f]quinoline (IQ), the cell is *salmonella typhimurium* and the exogenous polynucleotide is umuC'-'lacZ Other plasmids suitable for detecting genotoxicants are provided in Vollmer et al. Applied and Environmental Microbiology 63(7) (1997) 2566-2571, describing DNA-damaga-inducible promoters recA, uvrA and alkA from *E. coli* fused to the *Vibrio fisheri* luxCDABE operon and cells comprising same.

Such cells can be effectively used in detecting genotoxicants.

Thus, the present invention further provides for a method of detecting a genotoxicant in a sample, the method comprising:

(a) contacting the sample with a population of cells which comprise the above-described genotoxicant sensing cells, and (b) analyzing expression/activity of said reporter gene in the cells, wherein an upregulation of said activity/expression of the reporter gene upon contact with the sample is indicative of presence of the analyte in the sample.

It will be appreciated, that the analyte may be comprised in any of fluid, powder, gaseous or aerosol sample.

Reporter expression can be qualified and quantified electrochemically, as described herein. However, especially reporters used for genotoxicant detection can also be fluorescers such as the polypeptides belonging to the green fluorescent protein family including the green fluorescent protein, the yellow fluorescent protein, the cyan fluorescent protein and the red fluorescent protein as well as their enhanced derivatives. In such a case, the reporter polypeptide can be quantified via its fluorescence, which is generated upon the application of a suitable excitatory light. Alternatively, a polypeptide label can be an epitope tag, a fairly unique polypeptide sequence to which a specific antibody can bind without substantially cross reacting with other cellular epitopes. Such epitope tags include a Myc tag, a Flag tag, a His tag, a Leucine tag, an IgG tag, a streptavidin tag and the like. Further detail of reporter polypeptides can be found in Misawa et al. (2000) PNAS 97:3062-3066.

Thus, the present invention, further provides for a system for detecting an analyte (i.e., a genotoxicant) in a sample comprising an electrochemical chamber having therein the above-described cells and being configured for receiving the sample and generating an output signal responsively to electrochemical signals produced by said cells when contacted with said sample in said chamber.

Any of the reporter expression constructs of the invention can include additional elements. For example, polyadenylation sequences can also be added to the reporter expression construct in order to increase the translation effeciency of a reporter polypeptide expressed from the expression construct of the present invention. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression construct of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The construct may or may not include a eukaryotic replicon. If a eukaryotic replicon is present, then the vector is amplifiable in eukaryotic cells using the appropriate selectable marker. If the construct does not comprise a eukaryotic replicon, no episomal amplification is possible. Instead, the recombinant DNA integrates into the genome of the engineered cell, where the promoter directs expression of the desired nucleic acid.

The reporter expression construct can be introduced into the cell using a variety of molecular and biochemical methods known in the art. Examples include, but are not limited to, transfection, conjugation, electroporation, calcium phosphate-precipitation, direct microinjection, liposome fusion, viral infection and the like. Selection of a suitable introduction method is dependent upon the host cell and the type of construct used.

Cells and systems of the present embodiments can be employed in a variety of applications. For example, in the environmental field, the cell population of the present embodiments can be employed to detect the presence of pollutants such as halogenated hydrocarbons (used as pesticides), polycyclic aromatic hydrocarbons (carcinogenic compounds), acrylamide, acrylic acid and acrylonitrile, organophosphorous compounds (used as pesticides, insecticides, and chemical warfare agents), nitroaromatic compounds, such as nitrophenols, picric acid, trinitrotoluene (used as xenobiotics present in wastes of chemical armament plants as in civil factories for dye, pesticide, and other chemical manufacturing). Alternatively, the cells and systems of the present embodiments can be employed in the food and fermentation industries, where there is a need for quick and specific analytical tools. Analysis is needed for monitoring nutritional parameters, food additives, food contaminants, microbial counts, shelf life assessment, compliance with specifications or regulations, and other olfactory properties like smell and odor. In pharmaceuticals and medicine, the cells and systems of the present embodiments can be used for drug identification and qualification (e.g., determination of active ingredients in pharmaceutical formulations]. The cell populations of the present embodiments can also be used for detecting narcotics and explosives such as trinitrotoluene (TNT), cyclonite (RDX), pentaerythritol tetranitrate (PETN) C-4 class explosives, and combinations thereof [Yinon, Y. and Zitrin, S. (1993) Modern Methods and Applications in Analysis of Explosives, John Wiley & Sons, Ltd., Sussex, U. K.]. Cells and systems for detection of can be used for detecting water toxicity and drug pharmacokinetcs.

Figure 2:
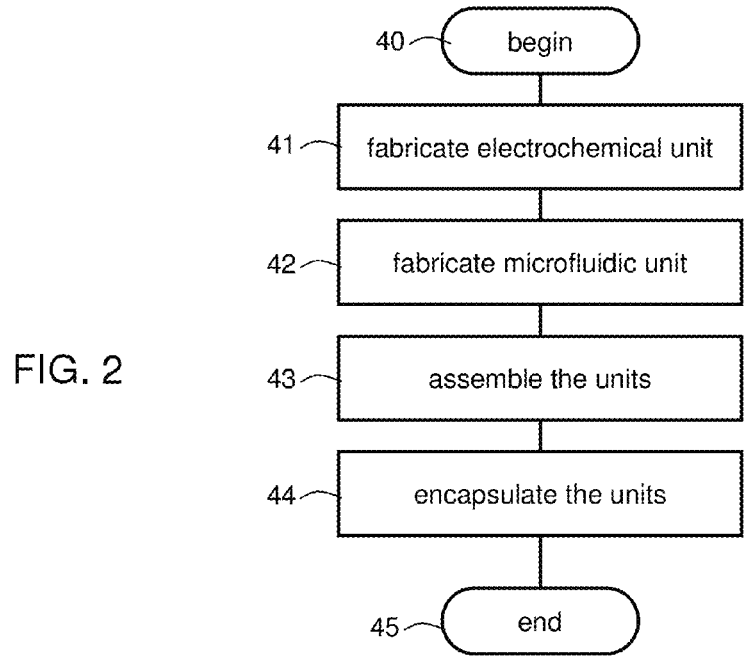

Reference is now made to FIG. 2 which is a flowchart diagram describing a method suitable for fabricating a system for analyzing a liquid, according to various exemplary embodiments of the present invention. The method can be executed for fabricating system 10.

It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The method begins at 40 and continues to 41 at which an electrochemical unit is fabricated. The electrochemical unit can be fabricated using an additive or partially additive process, wherein electrodes are deposited on a substrate and microchamber walls surrounding the electrodes are deposited to form a microchamber having the electrodes on a base thereof. Alternatively, a subtractive or partially subtractive process can be employed, wherein a microchamber is etched in a substrate and the electrodes are deposited on the base thereof. Combination of the above processes is not excluded from the scope of the present invention. A representative example of a process suitable for fabricating an electrochemical unit, according to some embodiments of the present invention is described below.

The method continues to 42 at which a microfluidic unit having microchannels is fabricated. The microfluidic unit can be fabricated by any known technique for the fabrication of microfluidic systems, be including, without limitation, injection molding, soft lithography, hot embossing, stereolithography, three-dimensional jet printing, dry etching and the like. For example, a polymeric material can be injected into a mold shaped complementary to the desired shape of the microfluidic unit. A representative example of process suitable for the present embodiments is provided in the Examples section that follows.

The method continues to 43 at which the microfluidic unit and the electrochemical unit are assembled such as to establish fluid communication between the microchannels and the microchamber. Optionally and preferably the method continues to 44 at which the system, including the microfluidic unit and the electrochemical unit is encapsulated with a sealed encapsulation in a manner such that an inlet port of the microfluidic unit remains exposed to the environment.

The method ends at 45.

Figure 3:
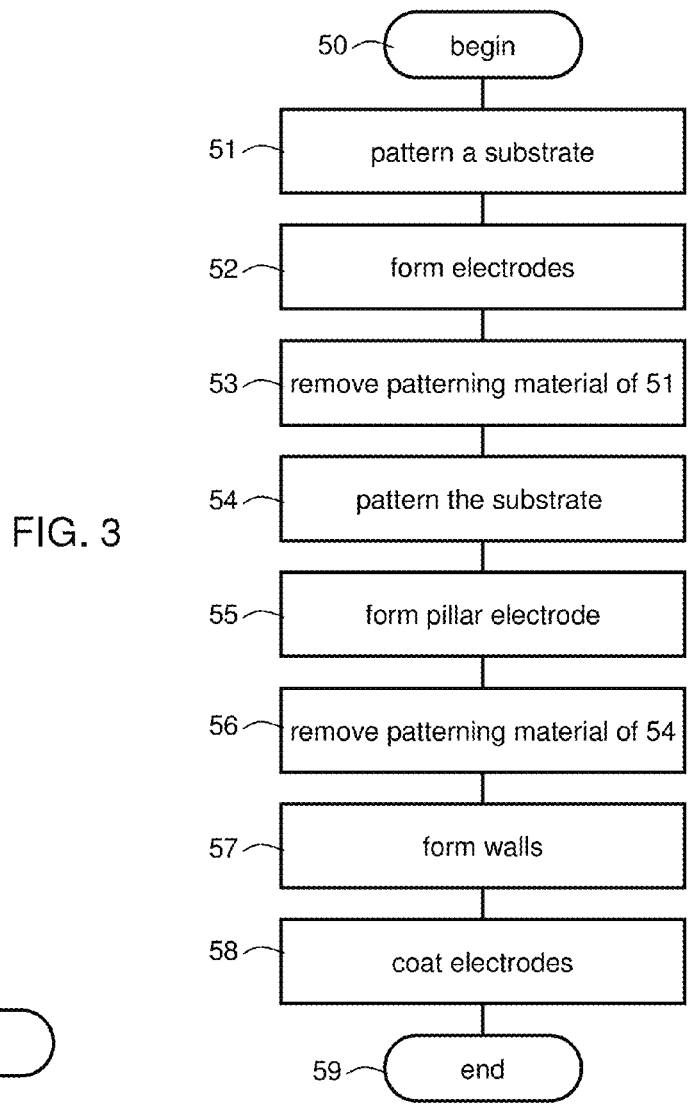

Reference is now made to FIG. 3 which is a flowchart diagram describing a process suitable for fabricating an electrochemical unit, according to some embodiments of the present invention. The process can be executed for fabricating electrochemical unit 12 of system 10.

The process begins at 50 and continues to 51 at which a substrate is patterned, for example, by means of photolithography, to provide a patterned substrate. The substrate can be of any type, such as, but not limited to, a silicon wafer or the like. Optionally and preferably a passive layer of a chemically nonreactive or low reactivity material is formed at one or both of the surfaces of the substrate prior to the patterning, e.g., to protect from degradation by contact with moisture. For example, when the substrate is a silicon wafer, a silicon oxide layer can be formed. Such layer can be formed using any procedure known in the art, for example, dry or wet oxidation at high temperatures, use of a precursor, e.g., silane or tetraethylorthosilicate, vapor deposition an the like.

The patterning 51 can be by any patterning known in the art and using any type of patterning material such as positive or negative photoresist material. For example, the patterning 51 can include vapor deposition of an image reversal photoresist material. In experiments performed by the present inventors the an AZ5214 image reversal photoresist material was used. This material is commercially available from Clariant Corporation of Somerville, N.J.

The process continues to 52 at which electrodes and electrical contacts are formed on the patterned substrate, for example, by means of metal evaporation. The metal can be gold, silver, nickel, palladium, copper, rhodium, iridium and the like. Also contemplated are metal alloys, such as, but not limited to, nickel-palladium, nickel-gold and the like. In various exemplary embodiments of the invention planar electrodes are formed. Following the formation of the electrodes and electrical contacts, the process preferably continues to 53 at which the photoresist used for patterning is removed, for example, by means of a lift off technique or the like.

Optionally and preferably, the process proceeds to 54 at which the substrate including the formed and electrodes and electrical contacts is patterned, such that one electrode is exposed while other electrodes are masked by a photoresist material. This embodiment is particularly useful when it is desired to form a working electrode shaped as a pillar or the like. The patterning 54 can be by any patterning known in the art and using any type of patterning material. For example, the patterning 54 can include spinning a photoresist material. In experiments performed by the present inventors a SU-8 2010 photoresist material was used. This material is commercially available from MicroChem Corporation.

In embodiments in which operation 54 is executed, the process preferably continues to 55 at which a pillar is formed onto the exposed electrode. This is preferably does by electrodeposition, but other techniques, e.g., vapor deposition. A representative example of a material suitable for forming a pillar electrode is copper, but other materials, preferably, but not necessarily, noble metals are not excluded from the scope of the present invention. Once the pillar electrode is formed, the process preferably continues to 56 at which the patterning material applied at 54 is removed, for example, using a photoresist stripper solution, such as, but not limited to, N-methylpyrrolidone (NMP), acetone, gamma-butyrolactone, N-methyl-formamide, N,N-dimethylformamide (DMF) and N,N-dimethylacetamide (DMAc).

In various exemplary embodiments of the invention the process contours to 57 at which walls surrounding the electrodes are deposited onto the substrate to form one or more microchamber thereon. The height of the walls is preferably higher than the height of the electrodes. Typically, the height of the deposited walls is, without limitation, on the order of several tens of microns. The deposition 57 can be by any technique known in the art and using any type of material, preferably, but not necessarily, a non-conductive material. A representative example of a material suitable for forming the walls of the microchamber(s) is a photoresist material. For example, the deposition 57 can include spinning a photoresist material. In experiments performed by the present inventors a SU-8 3050 photoresist material was used. This material is commercially available from Clariant Corporation of Somerville, N.J.

Optionally, the process continues to 58 at which one or more of the electrode is coated. For example, when a pillar electrode is formed (see 55), the pillar electrode is coated by a conductive material, preferably a metal. In some embodiments of the present invention, a copper pillar is coated with gold. The coating 58 can be by any known technique, e.g., via electrodeposition. Additionally or alternatively, 58 can include coating one or more of the electrode by a combination of materials, such as, but not limited to, silver/silver chloride, silver/silver bromide, silver/silver fluoride, and silver/silver iodide, copper/copper halide, copper/copper oxide, copper/copper sulfate etc., so as to form a reference electrode.

The process ends at 59.

Figure 4:
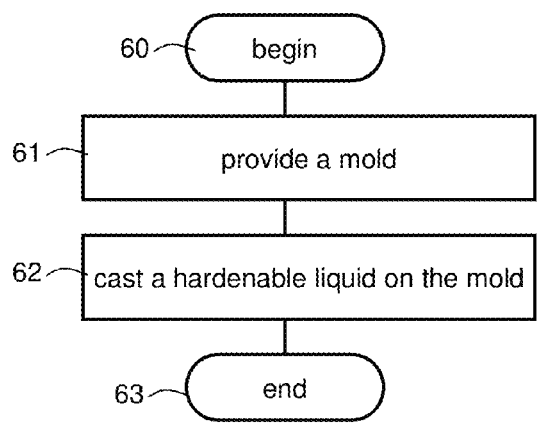

Reference is now made to FIG. 4 which is a flowchart diagram describing a process suitable for fabricating a microfluidic unit, according to some embodiments of the present invention. The process can be executed for fabricating microfluidic unit 14 of system 10.

The process begins at 60 and optionally and preferably continues to 61 at which a mold having raised features for patterning one or more microchannels is provided. The raised features of the mold can be shaped to pattern separated microchannels or a network of microchannels wherein there is a fluid communication among two or more of the microchannels. In any event, the raised features of the mold are shaped to pattern a fluid inlet port which is in fluid communication with at least one of the microchannels. The mold can be fabricated by a micromilling machine or by any other process, such as, but not limited to, a process suitable for MEMS, as further detailed hereinabove. The mold can be made from any material, which typically depends on the processes used for fabricating the mold. For example, when micromilling machine is used, a preferred material is brass, and when MEMS process is employed, a preferred material is hardened (e.g., UV cured) photoresist material. Other materials are not excluded from the scope of the present invention.

The method continues to 62 at which a hardenable liquid or a liquefied material, such as, but not limited to, the materials described above (e.g., PDMS) is cast on the mold to form the microfluidic unit.

The method ends at 63.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

A first prototype portable solid-state system for whole cell electrochemical analysis was fabricated and tested according to some embodiments of the present invention.

Methods

Platform Fabrications

The portable solid-state system was fabricated using conventional micro-fabrication and integration processes. The system was made of two micro-chips (FIG. 5C): an electrochemical chip (Part A), serving as the electrochemical unit and a microfluidic chip (Part B) serving as the microfluidic unit. The electrochemical chip (FIG. 5A and FIG. 5B) included microchambers and channels fabricated on single crystal silicon substrate by a deep-etch MEMS process, according to the teachings of R. Popovtzer, et al., Sens. Actuators B Chem. 119 (2006) 664.

The electrochemical chip comprised four cylindrical electrochemical 50 µm deep microchambers with different radii: 1 mm, 0.5 mm, 0.25 mm, and 0.125 mm. The corresponding volumes were 157 nl, 39 nl, 9.8 nl, and 2.5 nl. Each chamber contains three electrodes: working electrode (WE), counter electrode (CE) and reference electrode (RE). The electrodes were made of thin evaporated gold (200 nm)/Cr(15 nm). The open reference electrode was coated with Ag/AgCl layers (FIG. 5B). The Ag/AgCl open reference electrode was manufactured by a two step electrochemical process: a) Ag electroplating (Standard Ag nitrate bath) at a rate of 0.57 µm/minute. b) Anodization of the Ag in a bath containing chlorine ions. The fabrication process outline is presented in FIG. 15.

The second part of the system, the microfluidic chip, was made from PDMS and included microchannels feeding the water to the electrochemical Si based part. The chip was manufactured using molding of PDMS into a machined Brass matrix. The PDMS microfluidic chip was mounted on the Si based electrochemical chip and both were packaged on a measurement platform made of Delrin and a polymethylmethacrylate PMMA seal. The Brass matrix, the PMMA seal and the Delrin platform were produced by Computer Numerical Control (CNC) machining (FIGS. 6A-B) with a minimum resolution of about 50 microns. The electrochemical microchambers and the chip mounted on the measurement platform were connected to a portable potentiostat (EmStat, made by PalmSens Inc.) using a 16 channel multiplexer allowing a sequential reading and monitoring of 4 electrochemical micro-chips (each with 4 microchambers) at the same experiment.

Electrochemical Characterization Assays

The system was evaluated by testing its electrochemical performance for the analysis of a known chemical reaction. Therefore, Potassium ferrocyanide ($K_4[Fe(CN)_6]$, 0.010 M, Sigma), Potassium ferricyanide ($K_3[Fe(CN)_6]$, 0.010 M, Sigma) and KCl (1 M, Sigma) were mixed yielding a solution with the redox couple $Fe^{2+}/Fe^{3+}$ ions. This assay was evaluated by conventional cyclic voltammetry at varying scan rates.

The second test was for the evaluation of the oxidation of the reaction by products. Para-Aminophenol (pAP, FW 145.6, Sigma) was intentionally introduced into deionized water (DI) and the electrochemical activity of the pAP was measured under conditions similar to that of those on the test chip. The pAP was diluted with DI to final concentrations of 0.4, 0.04 and 0.004 mg/ml. The tested aliquots volume was 2.5 µl that were introduced into the electrochemical microchamber. First, 0.4 mg/ml pAP was evaluated by cyclic voltammetry assay at various scan rates in two similar electrochemical micro-chambers. Then, chrono-amperometry at applied potential of 300 mV vs. open Ag/AgCl reference electrode was measured using the EmStat (made by PalmSens) potentiostat. The data was stored for further processing using a Universal Serial Bus interface (USB) between the EmStat (made by PalmSens) and a conventional PC.

Toxicity Bio-Detection Assays

Toxicity analysis experiments utilized two strains of genetically engineered bacteria; *Escherichia coli* for the Nalidixic acid (NA) detection, and *Salmonella typhimurium* TA1535 for the 2-Amino-3-methylimidazo[4,5-f]quinoline (IQ) detection. *Escherichia coli* RFM443/pBR2TTS cells harboring a sulA::phoA fusion were grown overnight in MOPS growth medium containing 0.1 mg/ml ampicillin with shaking conditions at 37° C. The overnight culture was diluted ×1/100, regrown to an optical density of 0.2 (600 nm). Finally NA (FW 254.22, Sigma) was added to a final concentration of 10 µg/ml. Following further incubation at various times of 0, 60, 90, or 120 minutes under similar conditions, aliquots of 3 µl were introduced into the electrochemical microchambers. Shortly after applying a constant potential of 300 mV vs. Ag/AgCl in the electrochemical chamber, the enzymatic substrate para-Aminophenyl phosphate (pAPP, MW 211.09, diagnoSwiss) was added reaching a concentration of 0.8 mg/ml.

Control samples were prepared with the addition of growth medium instead of NA or pAPP to the incubation stage in order to verify the influence of NA on the induction of the bacteria and pAPP on the generated bio-electrochemical response.

*Salmonella typhimurium* TA1535 pSK1002 [Y. Oda et al., Mutat. Res. 147 (1985) 219] cells were used for the IQ bio-detection. The construction of the pSK1002 plasmid was reported in H. Shinagawa et al. Gene. 23 (1983) 167, which is hereby incorporated by reference in its entirety. The exposition of bacteria was done according to Reifferscheid et al. [Reifferscheid et al., Mutat. Res. 253 (1991) 215]. An over night culture of the bacteria was refreshed in 20 ml TGA-medium (1:10 dilution of bacteria) and grown for further 2 h (37° C., 150 rpm). Prior to exposition the optical density ($\lambda$=595 nm) of the bacterial culture was adjusted to 0.44 by dilution with TGA medium. The pre-genotoxic compound IQ was activated by adding a post-mitochondrial liver homogenate of induced rats (S9-fraction). The S9-fraction was obtained from *RCC Cytotest Cell Research GmbH* (Roβdorf, Germany). It was stored at −80° C. and kept on ice after thawing for immediate usage. Cofactors and salts were added for the activation of S9-enzymes. The final concentrations of the components in the reaction mixture were: S9-fraction 0.8% (v/v), NADP 2.9 mM, glucose-6-phosphate 3.3 mM, KCl 24 mM and $MgCl_2$ 5.9 mM. 70 µl of the bacterial suspension containing the S9-fraction (240 µl S9-fraction in 8 ml bacterial culture $OD_{595}$=0.44) were added to 20 µl of a stock solution (containing the cofactors and salts in 10×TGA medium) and mixed with 500 µg/ml ampicillin. Finally, 180 µl of sample (aqueous dilutions of an IQ-stock solution in DMSO, final IQ-concentrations 5 µM, 1.25 µM and 0.31 µM) or negative control (3% DMSO in water) were added yielding a total volume of 270 µl. The $OD_{595}$ of the exposed mixture was measured after an incubation time of 2 h at 37° C. and 900 rpm in shaking conditions.

The activity of the reporter enzyme β-galactosidase in the induced bacteria was measured by making use of the substrate para-Aminophenyl β-D-galactopyranoside (pAPG, 0.5 mM final concentration, Sigma). Shortly after the addition of pAPG, aliquots of 3 µl were introduced into the electrochemical microchambers and a constant potential of 300 mV vs. Ag/AgCl was applied on the electrochemical chamber in order to quantify the enzymatically generated product pAP. The setup was connected in such a way that the output current was monitored (i.e. amperometry measurement).

pBRphoA Plasmid Construction

Plasmid pBRphoA includes the phoA gene, two repeats of a transcription terminator site (2TTS), multiple cloning site (MCS), ampicillin resistance and origin of replication from pMB1. The phoA gene was amplified by PCR reaction from WT *E. coli* strain MG1655 (NC_000913) (Blattner et al., 1997) using the primer 1R, a 5' primer introduced with a BstBI restriction site with the 3' primers 1F/2F/3F, introduced with an SacI site (Table 1). All combinations were designed to amplify a 1452 bp BstBI-SacI fragment containing the Shine-Dalgarno sequence and an additional stop codon. In order to find the best active PhoA enzyme three versions were constructed:

WT sequence (primer 1F).
Conversion of GTG to ATG (primer 2F).
Conversion of GTG to ATG and the Shine-Dalgarno sequence adjusted to consensus sequence (AGGAGG) (primer 3F).

The three PCR products and the vector (plasmid pBR2TTS) were digested with the restriction enzymes BstBI and SacI and ligated to produce a 5542 bp plasmid. Colonies harboring the new plasmid were selected by colony PCR. The purified plasmid was restricted by EcoRI. Plasmids with the right restriction pattern were selected and the phoA insert and junction sites were verified by sequencing with primers APL1, APL2 and APL3 (Table 1). AP activity of two positive colonies of each construct was tested by induction with Nalidixic Acid (NA) according to the method developed by Manoil (1991) Positive colonies that expressed alkaline phosphatase activity were selected.

Gene Promoter Fusion

A 320 by segment upstream of the sulA gene (NC_000913.2) was amplified from WT *E. coli* strain MG1655 by PCR with the primers sulF and sulR (Table 2) containing the KpnI and SacI recognition sequences, respectively. Following digestion of the PCR product with SacI and KpnI, it was directionally ligated to SacI- and KpnI-digested pBRphoA (the promoter-less phoA plasmid), to create a 5856 bp plasmid. The recA::phoA fusion was constructed by replacing a 6542 by BstBI-SacI fragment containing the luxCDABE operon in plasmids pBR2TTSrecA::lux with the 1452 bases of the phoA gene and its modifications.

TABLE 1

| Primers used in this study | | |
|---|---|---|
| Primer | Sequence 5' → 3'/SEQ ID NO: | note |
| Plasmid construction | | |
| 1F | GTATGAGCTCATGGAGAAAATAAAGTGAAC/2 | SacI |
| 2F | GTATGAGCTCATGGAGAAAATAAAATGAAC/3 | SacI ATG |
| 3F | GTATGAGCTCAAGGAGAAAATAAAATGAAC/4 | SacI Shine-Dalgarno ATG |
| 1R | CCGTTCGAATTATTATTTCAGCCCCAG/5 | BstBI ATT |
| APL1 | CCATAAACTGCCAGGAATTGG/6 | For sequencing |
| APL2 | GCTTACCGGGCAATACACTC/7 | For sequencing |
| APL3 | GGTGAATGGCAGGGAAAAAC/8 | For sequencing |

TABLE 1-continued

Primers used in this study

| Primer | Sequence 5' → 3'/SEQ ID NO: | note |
|---|---|---|
| sulA-F | CGTCAACGGTACCGCTGTAACTG/9 | KpnI |
| sulA-R | GCCTGAAGTGAGCTCAATCAATCC/10 | SacI |
| Linear Transformation | | |
| UrfaE | GCAAAATTGCCTCTGGGAAAGC/11 | |
| DrfaE | CCATGTGTCGGAGGATTGC/12 | |
| Mutants Verification | | |
| K1 | CAGTCATAGCCGAATAGCCT/13 | (Datsenko and Wanner, 2000) |
| K2 | CGGTGCCCTGAATGAACTGC/14 | (Datsenko and Wanner, 2000) |
| UphoA | GATTATCGTCACTGCAATGCTTCGC/15 | |
| DphoA | GCTGATTACAGGAGGTCATACG/16 | |
| UumuD | GCCTGAATCAGTATTGATCTGC/17 | |
| DumuD | CGCGTTTACATCACAGAGG/18 | |
| UuvrA | GCTGGTGCAACTCTGAAAG/19 | |
| DuvrA | CCTTGTTTACGCCTCTGCTGG/20 | |

Mutant Reporter Strains Construction

To increase the capabilities of the reporter cells as genotoxicity bioreporters, a series of knock-out mutations was introduced to the E. coli RFM443's genome. The genes that were selected to be deleted are genes affiliated with DNA repair mechanisms (Nucleotide Exicision Repair, uvrA; DNA Pol V, umuD) and a structural gene that can influence cell permeability (lipopolysaccharide, rfaE). The mutations were transferred to strain AB202 from the Keio collection, a set of precisely defined single-gene deletions of all nonessential genes in E. coli K-12 (Baba et al., 2006). The deletion mutations in uvrA and umuD were transferred by P1 transduction. The mutation in the rfaE gene was transferred by linear transformation (Datsenko and Wanner, 2000) due to the low phage titer using the P1 method. From each gene deletion experiment, eight $Km^R$ colonies were chosen and checked for the correct mutation structure by PCR using a combination of locus- and kanamycin-specific primers (Table 1). PCR fragments with the right size of both junctions were sent to sequencing. Sequences were indentified using BLAST program operating on the default options querying the NCBI nucleotide collection database. The construction of double or triple mutants was obtained by the elimination of the resistance using a helper plasmid expressing the FLP recombinase, which acts on the FRT (FLP recognition target) sites flanking the resistance gene. Using the methods described above, a set of mutated reporter strains was constructed as detailed in Table 2. Strains dedicated to harbor the phoA reporter gene were also engineered to contain a deletion in the chromosomal phoA gene to eliminate the possibility of native PhoA activity.

TABLE 2

| Strain | Host | Plasmid | Genotype |
|---|---|---|---|
| Genotoxicity reporter strains | | | |
| AB101 | AG1655 | pBR2TTSrecA::phoA(1F) | Bla |
| AB102 | AG1655 | pBR2TTSrecA::phoA(2F) | Bla |
| AB103 | AG1655 | pBR2TTSrecA::phoA(3F) | Bla |
| AB202 | RFM443 | pBR2TTSsulA::phoA(2F) | Bla strR galK2 lacD74 |
| Mutant reporter strains | | | |
| AB725 | RFM443 | pBR2TTSsulA::phoA | Bla strR galK2 lacD74 ΔphoA |
| AB726 | RFM443 | pBR2TTSrecA::phoA | Bla strR galK2 lacD74 ΔphoA |
| AB728 | RFM443 | pBR2TTSsulA::phoA | Bla strR galK2 lacD74 ΔphoA ΔumuD |
| AB729 | RFM443 | pBR2TTSrecA::phoA | Bla strR galK2 lacD74 ΔphoA ΔumuD |
| AB731 | RFM443 | pBR2TTSsulA::phoA | Bla strR galK2 lacD74 ΔphoA ΔumuD ΔrfaE |
| AB732 | RFM443 | pBR2TTSrecA::phoA | Bla strR galK2 lacD74 ΔphoA ΔumuD ΔrfaE |
| AB734 | RFM443 | pBR2TTSsulA::phoA | Bla strR galK2 lacD74 ΔphoA ΔrfaE |
| AB735 | RFM443 | pBR2TTSrecA::phoA | Bla strR galK2 lacD74 ΔphoA ΔrfaE |
| AB737 | RFM443 | pBR2TTSsulA::phoA | Bla strR galK2 lacD74 ΔphoA ΔuvrA ΔrfaE |
| AB738 | RFM443 | pBR2TTSrecA::phoA | Bla strR galK2 lacD74 ΔphoA ΔuvrA ΔrfaE |
| AB740 | RFM443 | pBR2TTSsulA::phoA | Bla strR galK2 lacD74 ΔphoA ΔuvrA |
| AB741 | RFM443 | pBR2TTSrecA::phoA | Bla strR galK2 lacD74 ΔphoA ΔuvrA |

Results

The microfluidic whole cell prototype biosensor of the present embodiments included 4 biochips with 4 microchambers each. The prototype biosensor successfully detected model toxicant NA and genotoxic material (IQ). The performance of the prototype elucidated the dependence of the bio-signal as a function of the induction time of the bacterial biosensor with the toxic material. The results of the measurements of the microfluidic whole cell electrochemical biochip are presented below. The calibration and the testing schemes are presented first. The biochip response to the two toxicants: NA and IQ are presented thereafter.

Electrochemical Characterization of the Micro-Chip

The electrochemical activity of the manufactured micro-chip was validated by a cyclic voltammetry assay with a $Fe^{2+}/Fe^{3+}$ electro-active solution. The cyclic voltammograms that resulted from the differently sized electrochemical microchambers are shown in FIG. 7A. The voltammograms using the electrochemical micro-chip show clearly the cathodic reduction of the $Fe^{3+}$ and the anodic oxidation of the $Fe^{2+}$. The measured open circuit potential of the reaction (e.g., 0.188 V vs. Ag/AgCl reference electrode) approximately corresponded to the predictable half cell potential (e.g. 0.124 V vs. Ag/AgCl reference electrode) of the Ferrocyanide—Ferricyanide reaction according to Nernst equation. The deviation of the experimented open circuit potential is due to the fact that an open Ag/AgCl reference electrode was used when its half cell potential was slightly influenced by the chemical reaction in the cell. The peak current of the anodic current and the associated applied potential (vs. the open Ag/AgCl electrode) were extracted and plotted versus the area and the 1/area of the working electrode respectively (FIG. 7B and FIG. 7C). The anodic current peak plot (FIG. 7B) yields a positive linear relation with a slope of 23.2±1.7 $\mu A/mm^2$. This relation meets the expected relation (e.g. 15.1 $\mu A/mm^2$ at 25° C.) calculated from Bard et al. [Bard et al., ELECTROCHEMICAL METHODS: Fundamentals and Applications, 2nd ed., John Wiley & Sons, New York, 2001]. Furthermore, the applied potential at the anodic peak as a function of 1/area of the working electrode demonstrated a positive linear relation (FIG. 7C). This dependence may be attributed to the fact that Nernst equation is slightly modified on very small electrodes, when a current flow may cause an increase with the ohmic drop (uncompensated resistance and solution resistance) near the electrode.

The electro-active species pAP is the product molecule produced by the biochemical reaction of the enzyme alkaline phosphatase using pAPP as a substrate [C. G. Bauer et al., Anal. Chem. 68 (1996) 2453] or the enzyme β-galactosidase using pAPG as a substrate [R. Popovtzer et al., Nano Lett. 5 (2005) 1023]. The induction level of the enzyme by the genetically engineered bacteria of the present embodiments is proportional to the toxicant concentration in the sample. Cyclic voltammetry assays of different scan rates were applied on duplicate electrochemical microchambers with aliquots of 0.4 mg/ml pAP solution. The anodic current peak was measured and is plotted as a function of the square root of the scan rate (FIG. 8). The result is a linear dependence which fits conventional cyclic voltammetry modeling [Bard et al., supra]. Furthermore, a correlation coefficient of 0.98 was calculated between the two similar electrochemical microchambers indicated linear dependence. Therefore, these results demonstrate the reproducibility of the electrochemical signal in the system of the present embodiments.

The reactivity of the electro-active species pAP was tested by the fabricated system. Chrono-amperometry results for the response to different concentrations of pAP are shown in FIG. 9. The results demonstrated the dependence of the generated electrochemical current as a function of the electro-active species concentrations. It is important to point at the signal dependence on the electro-active species dose. This dependence is important since the pAP species is the end product of the biochemical reactions in the bacterial biosensor of the present embodiments, hence its production rate depends on the toxicant concentration in the analyzed sample.

Electrochemical Bio-Detection of Toxic Materials

The presence of toxicants induces a cascade of biological reactions in the genetically engineered bacteria of the present embodiments producing an increased concentration of the enzymatic bio-reporter alkaline phosphatase. This enzyme catalyzes the reaction converting the substrate pAPP to the electro-active species pAP. Therefore, by using an appropriate electrochemical transducing system, the generated electrochemical bio-signal can be detected. FIG. 10A presents chrono-amperometric results of the response of *E. coli* bacteria in the presence and the absence of the model toxicant NA. The response of the bacteria in the presence of NA showed an increasing electrochemical current after pAPP was added. This is compared to the response of induced bacteria without the addition of pAPP which demonstrated a decreasing current characteristics. Furthermore, the induced bacteria exhibited a more rapidly increasing electrochemical current than non-induced bacteria when pAPP was added to both samples.

Note that the "non-induced" (not exposed to the toxicant) bacteria demonstrated a unique current rise when pAPP was added to the bacterial suspension. That result was reproducible and is characteristics to that specific bacterial system and toxicant.

Chrono-amperometric results of bacterial cells following different induction periods with NA are shown in FIG. 10B. The results demonstrated the dependence of the generated electrochemical current with the total induction time of the bacteria by the toxicant. For longer induction times the current increased more rapidly (FIG. 10C), indicating the ongoing enzyme production in the bacterial cells during the induction and hence an increasing enzyme concentration with time. Therefore, increasing induction time yields higher alkaline phosphatase concentration yielding higher generation rate of pAP. Since the current is proportional to the pAP concentration, an increasing pAP generation rate yields an increasing electrochemical current. This result was verified and modelled for a different system [R. Popovtzer et al., J. Electroanal. Chem. 602 (2007) 17] where the enzyme was β-galactosidase and the substrate was also pAPG similar to the work that is presented here.

The effect of the genotoxic material IQ on the electrochemical bio-signal was tested and analyzed with the microchip of the present embodiments (FIGS. 11A-B). The dependence of the differential slope (the difference between the slope detected by induced bacteria and the slope detected by non-induced bacteria) on the IQ concentration is shown in FIG. 11A. Higher IQ concentrations demonstrated more rapidly increasing electrochemical current characteristics. The influence of the WE radius on the slope of the detected electrochemical current is shown in FIG. 11B. The current increased with the dimension of the microchambers. Also observed was larger current from non-induced bacterial cells for larger microchambers (negative control). A figure of merit describing the bio-detection efficiency was devised in order to quantify the system signal (response to induced bacterial cells) to noise (response of non-induced bacterial cells) performance.

The bio-detection efficiency of the micro-chip of the present embodiments was modeled by defining induction factor (IF) values, as shown in FIG. 12. The induction factor was defined as the ratio between the bio-signal detected from bacterial cells in the presence of a toxicant and the bio-signal detected from bacterial cells in the absence of a toxicant (negative control). Induction factor values for two different size electrochemical microchambers are shown in FIG. 12. Both cells show similar (within experimental error) induction factor. These results demonstrate that scaling down of the micro-chip does not deteriorate the induction factor.

Electrochemical Genotoxicity Detection of the Generated Strains

The reporter was responsive to the three model genotoxicants nalidixic acid (NA), mitomycin C (MMC) and hydrogen peroxide ($H_2O_2$), proving its ability to respond to three different types of DNA damage: DNA breaks caused by a DNA synthesis halt (NA), multiple-target attacks on the DNA caused by ROS ($H_2O_2$), and cross links in the DNA caused by bi-alkylating agents (MMC) (FIG. 14). The ΔrfaE reporter strains were found to respond to lower concentrations of MMC and NA, which are high molecular weight substances. The reporter strain that did have an elevated response to hydrogen peroxide was the uvrA mutant. The reporter strain mutated in uvrA and rfaE genes responded to the pre-genotoxic compound 2-Amino-3-methylimidazo[4,5-f]quinoline (IQ) following metabolic activation with lyophilized liver S9 fraction. The response was similar to the response of the umu-test reporter strain under the same conditions. Demonstrating the ability of our reporter strain to detect pre-genotoxic compound following metabolic activation was an important step in our development of a genotoxicity assay. It has underlined the potential of our system to detect a group of environmental pollutants that are not genotoxic per-se but rather bio-activated in the xenobiotic metabolism in vivo.

Example 2

A second prototype portable solid-state system for whole cell electrochemical analysis was fabricated and tested according to some embodiments of the present invention. The system was made using conventional micro-fabrication and integration processes, and included an electrochemical microchip mounted with a microfluidic chip on to an electrochemical platform.

The system was similar to the system described in Example 1, above. The electrodes were fabricated as described above, except that the Ag electroplating was at a rate of 0.8 μm/min.

First Experimental Platform

The experimental platform in this experiment was based on the electrochemical and microfluidic chips. The microfluidic chip (30×20.5×12 mm) was made from PDMS and it included the channels (2.2 mm with width and height) feeding the water to the electrochemical Si based micro-chip.

Three different configurations of the microfluidic chip were manufactured using conventional molding of PDMS into a machined Brass matrix. Following is detailed description and characterization of the microfluidic chip. The Brass mold configurations are shown in FIGS. 16A-D.

The PDMS molding process was as follows:
1) 5 g of curing agent (SYLGARD 184 Silicone Elastomer Curing Agent) were taken with a plastic spoon into a chemical glass.
2) 50 g of elastomer base (SYLGARD 184 Silicone Elastomer Base) was added into the chemical glass (ratio of 1:10 with the curing agent).
3) The blend was continuously mixed for 5 min.
4) The mixture was left in a vacuum chamber for 30 min until it reached full degassing of air bubbles.
5) The degassed mixture was poured slowly into the Brass mold filling it completely.
6) The mixture in the Brass mold was left on a hotplate for 1 hour at 100° C.
7) The PDMS molding was cooled down and extracted from the Brass mold.

Flow analysis of the flow in the microfluidic chip was modeled and simulated with COMSOL Multiphysics software (3.4, COMSOL). Simulation results of a single microchannel are presented in FIG. 17A-B. The results demonstrated a laminar flow due to low Reynolds number in the channel.

A PMMA seal was manufactured in order to fasten the micro-fluidic and the electrochemical chips together to prevent fluid leakage. The seal was composed of 2 parts (FIG. 18A) when 3 different configuration of the seal were manufactured (FIG. 18B) which corresponded to the micro-fluidic chip configurations and allowed a directed integration of the inlet needle for the infusion of solutions (FIG. 18C). Schematic layout of the PDMS microfluidic chip integrated with the seal is shown in FIG. 18D.

The microfluidic chip was mounted on the Si based electrochemical microchip as shown in FIG. 19, and into the electrochemical platform.

The electrochemical platform was made of polyoxymethylene (POM) and a PMMA seal. Three different configurations of the PMMA seal were fabricated which corresponded to the configurations of the micro-fluid chips.

The Brass matrix, the PMMA seal and the POM platform were produced by Computer Numerical Control (CNC) machining (FIG. 20A-D) with a minimum resolution of about 50 microns. The electrochemical micro-chambers and the chip mounted on the measurement platform were connected to a portable potentiostat (EmStat, made by PalmSens Inc.) using a 16 channel multiplexer allowing a sequential reading and monitoring of 4 electrochemical micro-chips (each with 4 micro-chambers) at the same assay. Solutions were streamed through the system with needles puncturing through the holes in the PMMA seal and into the PDMS molding.

Second Experimental Platform

The second experimental platform was based on a "dip and measure" concept where the portable system infuse the sample into the electrochemical chip, the bio-detection reaction occurs and the output signal is analyzed. The system included the electrochemical unit, the microfluidic unit with sampling capabilities, and an electrochemical platform (FIG. 21A-B). A needle was used to puncture the PDMS sampling chamber from a designated hole on the side of the PMMA seal in order to pipette solutions into the analysis chamber.

Following is detailed description and characterization of the microfluidic chip. The microfluidic chip was composed of 3 parts: a sampling part, an analysis part, and a pipetting part (FIGS. 22A-D). The system was made of PDMS molding in polymeric molds. Four different molds were manufactured: a sampling mold, a single chamber analysis mold, a four-chamber analysis mold, and a pipetting mold. The molds are shown in FIG. 23.

The PDMS molding process was as follows:
1) 5 g of curing agent (SYLGARD 184 Silicone Elastomer Curing Agent) were taken with a plastic spoon into a chemical glass.
2) 50 g of elastomer base (SYLGARD 184 Silicone Elastomer Base) was added into the chemical glass (ratio of 1:10 with the curing agent).
3) The blend was continuously mixed for 5 minutes.

4) The mixture was left in a vacuum chamber for 30 minutes until it reached full degassing of air bubbles.
5) The degassed mixture was poured slowly into the polymeric mold filling it completely (the mold was treated with oil spray prior to PDMS introduction).
6) The mixture in the mold was left for 24 hours in room temperature.
7) The PDMS molding was extracted from the mold with scalpel.

Flow analysis of the flow in the microfluidic chip was modeled and simulated with COMSOL Multiphysics software (3.4, COMSOL). Simulation results of a single microchannel are presented in FIG. 24A-C. The results demonstrated a laminar flow due to low Reynolds number in the channel.

A PMMA seal was manufactured in order to fasten the microfluidic unit and the electrochemical unit together to prevent fluid leakage. The PMMA seal included a niche to a pipetting double sided button made of PMMA. The button has mixing and sampling sides which are varied with the length of the knobs. The knobs pressed the PDMS pipetting molding which allowed infusing and mixing of the sample in the sampling chamber. At first, the sampling side was used to infuse the solution through the sampling chamber and into the analysis chamber. Afterwards, the button changed into the mixing side which allowed mixing the sample with the bacterial assay and the cofactors on the reaction chambers. Schematic layouts of the PMMA seal, the pipetting button, and a side view of the pipetting button describing the mixing and the sampling sides are provided in FIGS. 25A-C, respectively.

The electrochemical platform was based on an experimental base with electrical interface to electrochemical analysis system and niches to the electrochemical micro-chip, the micro-fluidic system and the PMMA seal.

Example 3

A third prototype portable solid-state system for whole cell electrochemical analysis was fabricated and tested according to some embodiments of the present invention. The system included an electrochemical microchip and a microfluidic chip. The electrochemical microchip included a 3D copper-based pillar as the working electrode coated with thin layer of gold (FIGS. 26A-D).

Each micro-chip included 4 electrochemical microchambers (2 chambers with gold planar working electrodes and 2 chambers with Cu/Au pillar working electrodes). Following is a detailed description of the fabrication process employed in the present example.

The fabrication process outline is presented in FIG. 27.
Metal Definition
AZ-5214 negative photoresist lithography procedure ($1^{st}$ mask)
1) Wafer preparation
a) Wafer cleaning
i) Simple clean—removal of organic contaminants
Process:
(a) Cover the surface of the wafer with acetone.
(b) Thoroughly scrub the surface of the wafer with a swab.
(c) Rinse the wafer with isopropanol (IPA).
(d) Blow dry the wafer with $N_2$ gun.
ii) Photoresist stripper (Nanostrip, piranha)
iii) RCA clean—removal of organic, oxide, and metallic contaminants
Process:
(a) Organic clean: removal of insoluble organic contaminants with a 5:1:1 $H_2O:H_2O_2:NH_4OH$ solution.
(b) Oxide strip: removal of a thin silicon dioxide layer where metallic contaminants may accumulated using a diluted 20:1 $H_2O:HF$ solution.
(c) Ionic clean: removal of ionic and heavy metal atomic contaminants using a solution of 6:1:1 $H_2O:H_2O_2:HCl$.
iv) Piranha clean—removal of organic materials (photoresist, oil, etc.)
Process:
(a) Mix 98% $H_2SO_4$ (sulfuric acid) and 30% $H_2O_2$ (hydrogen peroxide) in volume ratios of 2-4:1
(b) Heat to 100° C.
(c) Insert wafers to the solution and wait for 10 min.
(d) Take the wafers out of the solution and rinse in deionized water (DI) for 5 min.
(e) Dry with $N_2$ gun.
b) Dehydration bake
i) Set the hotplate to 120° C.
ii) Transfer wafers to a metal wafer carrier.
iii) Bake the wafers for 10 min on the hotplate.
iv) Remove the wafer carrier from the hotplate using tweezers.
c) Mask cleaning
i) Place the mask in the mask cleaning holder.
ii) Apply acetone to the chrome surface. Do not allow the mask to dry with acetone on it.
iii) Scrub the chrome surface with a swab.
iv) Rinse the mask with IPA.
v) Dry with $N_2$ gun.
2) Apply photoresist
a) Photoresist coating
i) Mount the wafer on the RC-8 Spinner.
ii) Apply a quarter size puddle of HMDS (adhesion promoter) to wafer.
iii) Set the spinner to spin at 500 rpm with acceleration equal to 1000 rpm/s for 5 s, with open cover. Next, set the spinner to spin at 1300 rpm with acceleration of 3000 rpm/s for 30 s.
iv) Start spinning.
v) Apply a quarter sized puddle of AZ-5214 (negative resist) to wafer.
vi) Use same spin program, this results in 1.6 micron thickness of resist.
vii) Clean the spinner when done.
3) Softbake
a) Heat the hotplate next to the RC-8 Spinner to 112° C.
b) Set timer for 60 s.
c) Place the wafer on the hotplate, start timing.
d) When the time is up, remove the wafer.
4) Expose
a) Calculate the exposure time (Exposure dose/Measured intensity)
b) Set Karl Suss MA-6 mask aligner to: Soft contact, exposure time 0.8 s.
c) Expose the wafer.
d) If soft or hard contact was used, clean the mask.
e) Create an entry in the Karl Suss aligner log book when done.
5) Post exposure bake
a) Set a hotplate to 120° C.
b) Set timer for 2 min.
c) Place the wafer on the hotplate, start timing.
d) When the time is up, remove the wafer.

6) Flood exposure
a) Without mask, expose wafer for 40 s.
7) Develop
a) Pour AZ-726 developer to a Petri dish to cover the wafer.
b) Set timer to 35 s.
c) Start the timer. Place the wafer in the developer bath.
d) Quickly remove the wafer from the developer bath and rinse it in the water bath for 30 s (using the wafer holder).
e) Place the wafer on a clean room wipe. Blow dry with $N_2$ gun.
f) Dry the wafer holder.
8) Clean the workstation.

Metal Deposition

Gold (Au)/Chromium (Cr) evaporation using Edwards 306 evaporator

1) Plasma clean—insert wafers to microwave plasma cleaning oven for 1 min.
2) Clean and dry wafers.
3) Vent chamber
a) Open nitrogen gas cylinder (set the regulator to 0.5 bar).
b) Press seal, wait for 10 s and press vent. The chamber takes about 2 min to vent. Wait until the hissing stops and the pressure is 1000 mbar.
c) Attempt to open the chamber by gently lifting the bell jar. If the bell jar is hard to lift, it has not finished venting.
d) Once you have removed the bell jar, place it inverted on the cork ring, stop the venting process. Press seal and close the nitrogen cylinder.
4) Mount the wafers
a) Securely attach wafers onto sample holder using the bolts and washers (this will be mounted upside down).
b) Bolt the holder onto the bottom of the driven bearing using the bolt provided.
c) Turn the knob fully clockwise on the rotary stage controller and switch it on (using the switch the neon should light).
5) Pump
a) Replace the bell jar and implosion guard.
b) Press cycle on the pumping system controller. The chamber must pump down to below $1\times10^{-4}$ mbar before the plasma processing can be started (Ideally you should wait until it reaches below $5\times10^{-7}$ mbar for the best results).
6) Evaporation of chromium
a) Check the thickness monitor controller (FTM5) is correctly configured (by cycling through the parameters using the data button): Layer=1, Density=7.2 and z-value=28.9 if these values are not correct change them using the inc/dec buttons.
b) Ensure the pressure is below $5\times10^{-7}$ mbar, if it is not wait ideally until it is at $2\times10^{-7}$ mbar.
c) Open the shutter on the thickness monitor controller (FTM5), select A on the LT selector switch and select LT on the right-hand selector switch.
d) Slowly increase the current (using the graduated current control knob)
e) While watching the reflection of the chromium rod in the minor, it should start to glow initially at the ends, keep the current constant until the glow extends along its length.
f) Limit the current so that the pressure never exceeds $5\times10^{-6}$ mbar (and ideally stays below $1\times10^{-6}$ mbar).
g) Continue to gradually increase the current (so that the rod is glowing evenly) until the thickness monitor displays a rate of 0.1 or 0.2 nm s$^{-1}$ then wait until the layer is almost (<0.3 nm away) the desired thickness of 15 nm and turn the current down to zero.
h) Switch the right-hand selector switch back to 0 and close the shutter on the thickness monitor controller (FTM5).

i) Wait for about 5 min for the system to cool down and the pressure to return to $2\times10^{-7}$ mbar.
7) Evaporation of gold
a) Check the thickness monitor controller (FTM5) is correctly configured (by cycling through the parameters using the data button): Layer=2, Density=19.3 and z-value=23.2 if these values are not correct change them using the inc/dec buttons.
b) Ensure the pressure is below $5\times10^{-7}$ mbar, if it is not wait ideally until it is at $2\times10^{-7}$ mbar.
c) Open the shutter on the thickness monitor controller (FTM5), select B on the LT selector switch and select LT on the right-hand selector switch.
d) Then slowly increase the current (using the graduated current control knob) while watching the reflection of the boat containing the gold in the mirror, it should start to glow initially at the ends, keep the current constant until the boat is glowing evenly.
e) Continue to gradually increase the current (so that the boat is glowing evenly) eventually the gold will melt, at this point the pressure will rise especially if this is the first time a gold slug is melted.
f) Limit the current so that the pressure never exceeds $5\times10^{-6}$ mbar (and ideally stays below $1\times10^{-6}$ mbar).
g) Once the gold has melted increase the current until the thickness monitor displays a rate of 0.5 to 1 nm s$^{-1}$ then wait until the layer is almost (<2 nm away) the desired thickness of 300 nm and turn the current down to zero.
i) Do not let wafer heat to 80-90° C., when wafer heats close current and let it cool down to 50° C.
h) Switch the right-hand selector switch back to 0 and close the shutter on the thickness monitor controller (FTM5).
i) Wait for about 5 min for the system to cool down and the pressure to return to $2\times10^{-7}$ mbar.
8) Retrieve wafers
a) Switch the switch on the rotary stage controller to stop the sample stage rotating.
b) Open the nitrogen gas cylinder (set the regulator to 0.5 bars) and line to the evaporator.
c) Press seal wait 10 s and then press vent on the pumping system controller. The display will show chamber vent. The chamber will take about two minutes to vent.
d) Wait until the hissing stops and the pressure is reading $1\times10^3$ mbar.
e) Attempt to open the chamber by gently lifting the bell jar. If the bell jar is hard to lift, it has not finished venting.
f) Remove the bell jar and place it inverted on the cork ring.
g) Stop the venting process by pressing seal on the pumping system controller.
h) Close the nitrogen cylinder.
i) Unbolt the substrate holder from the bottom of the driven bearing and withdraw the holder.
j) Replace the bell jar and implosion guard and then press cycle on the pumping system controller to pump the system down to keep the inside of the system as clean as possible.
k) Remove the samples from the sample holder, rap the sample holder in tin foil and leave it on the evaporator for the next user.

Cleaning

AZ-5214 photoresist removal
1) Insert wafers to NMP bath.
2) Heat NMP bath to 80° C.
3) Heat ultrasound bath to 80° C.
4) Place NMP bath with wafers in ultrasound bath.
5) Start ultrasound, wait until resist lifts-off, 40-60 min.

Metal Definition

SU-8 negative photoresist lithography procedure (2$^{nd}$ mask)

1) Wafer preparation
 a) Wafer cleaning
  i) Simple clean—removal of organic contaminants
  Process:
   (a) Cover the surface of the wafer with acetone.
   (b) Thoroughly scrub the surface of the wafer with a swab.
   (c) Rinse the wafer with IPA.
   (d) Blow dry the wafer with $N_2$ gun.
 b) Dehydration bake
  i) Set the hotplate to 120° C.
  ii) Bake the wafers for 15 min on the hotplate.
  iii) Remove the wafer carrier from the oven using tweezers.
 c) Clean mask
  i) Place the mask in the mask cleaning holder.
  ii) Apply acetone to the chrome surface. Do not allow the mask to dry with acetone on it.
  iii) Scrub the chrome surface with a swab.
  iv) Rinse the mask with IPA.
  v) Dry with $N_2$ gun.
2) Apply photoresist
 a) Photoresist coating
  i) Mount the wafer on the Headway spinner.
  ii) Apply a quarter sized puddle of SU-8 2010 to wafer.
  iii) Set spread cycle to 500 rpm with acceleration equal to 100 rpm/s for 5 s.
  iv) Set the spinner to spin at 3000 rpm with acceleration equal to 300 rpm/s for 30 s.
  v) Start spinning.
  vi) This results in 10 μm thickness of resist.
  vii) Clean the spinner when done.
3) Softbake
 a) Heat the hotplate next to the Headway spinner to 100° C.
 b) Set timer for 3 min.
 c) Place the wafer on the hotplate, start timing.
 d) When the time is up, remove the wafer.
4) Expose
 a) Calculate the exposure time (Exposure dose/Measured intensity)
 b) Set Karl Suss MA-6 mask aligner to: Soft contact, exposure time 7 s.
 c) Expose the wafer.
 d) If soft or hard contact was used, clean the mask.
 e) Create an entry in the Karl Suss aligner log book when done.
5) Post exposure bake
 a) Set a hotplate to 100° C.
 b) Set timer for 4 min.
 c) Place the wafer on the hotplate, start timing.
 d) When the time is up, remove the wafer.
6) Develop
 a) Pour PM-Acetate developer to a Petri dish to cover the wafer.
 b) Set timer to 3 min.
 c) Start the timer. Place the wafer in the developer bath.
 d) Quickly remove the wafer from the developer bath and rinse with DI for 30 s (using the wafer holder).
 e) Place the wafer on a clean room wipe. Blow dry with $N_2$ gun.
 f) Dry the wafer holder.

Metal Electroplating

Working electrode Cu electroplating
1) Electrodeposition of Cu on the working Au electrode.
 a) Cu counter electrode placed at the cathode.
2) Cathode current density to be used is $j=10$ mA/cm$^2$ for growth rate of 0.5 μm/min.
3) Compute from CAD software file the area to be deposited (in cm$^2$) where the total current is:
 a) $I=j*area$ (mA) (according to Table 3).
4) Determine final deposition height by setting deposition time in minutes (height=0.5*time (μm)).
 a) For a 10 μm layer the deposition time of 20 min.
5) Connect the anode (+) of the potentiostat to a stand with a crocodile clip holding the Cu counter electrode, insert the electrode to the solution.
6) Connect the cathode (−) of the potentiostat to a device holding the wafer and connects to the collector connector on the wafer.
7) Set timer for 20 min.
8) Insert the wafer to the solution, the electrochemical cells should be entirely in the solution.
9) Start timer.
10) Take the wafer out of the solution and wash in DI for several seconds.

Cleaning

SU-8 photoresist removal
1) Insert wafers to NMP bath.
2) Heat NMP bath to 80° C.
3) Remove NMP bath from the hot plate.
4) Place NMP bath with wafers in the fume hood for the night.

Passivation

SU-8 negative photoresist lithography procedure (3$^{rd}$ mask)

1) Wafer preparation
 a) Wafer cleaning
  i) Simple clean—removal of organic contaminants
  Process:
   (a) Cover the surface of the wafer with acetone.
   (b) Thoroughly scrub the surface of the wafer with a swab.
   (c) Rinse the wafer with IPA.
   (d) Blow dry the wafer with $N_2$ gun.
 b) Dehydration bake
  i) Set the hotplate to 120° C.
  ii) Transfer wafers to a metal wafer carrier.
  iii) Bake the wafers for 15 min in the oven.
  iv) Remove the wafer carrier from the oven using tweezers.
 c) Mask cleaning
  i) Place the mask in the mask cleaning holder.
  ii) Apply acetone to the chrome surface. Do not allow the mask to dry with acetone on it.
  iii) Scrub the chrome surface with a swab.
  iv) Rinse the mask with IPA.
  v) Dry with $N_2$ gun.
2) Apply photoresist
 a) Photoresist coating
  i) Mount the wafer on the Headway spinner.
  ii) Apply a quarter sized puddle of SU-8 3050 to wafer.
  iii) Set spread cycle to 500 rpm with acceleration equal to 100 rpm/s for 10 s.
  iv) Set the spinner to spin at 3000 rpm with acceleration equal to 300 rpm/s for 30 s.
  v) Start spinning.
  vi) This gives 50 micron thickness of resist.
  vii) Clean the spinner when done.
3) Softbake
 a) Heat the hotplate next to the Headway spinner to 95° C.
 b) Set timer for 30 min.
 c) Place the wafer on the hotplate, start timing.
 d) When the time is up, remove the wafer.

4) Expose a) Calculate the exposure time (Exposure dose/Measured intensity)

b) Set Karl Suss MA-6 mask aligner to: Soft contact, exposure time 30 s.

c) Expose the wafer.

d) If soft or hard contact was used, clean the mask.

e) Create an entry in the Karl Suss aligner log book when done.

5) Post exposure bake a) Set a hotplate to 95° C.

b) Set timer for 10 min.

c) Place the wafer on the hotplate, start timing.

d) When the time is up, remove the wafer.

6) Develop a) Pour PM-Acetate developer to a Petri dish to cover the wafer.

b) Set timer to 8 min.

c) Start the timer. Place the wafer in the developer bath.

d) Quickly remove the wafer from the developer bath and rinse with IPA for 30 s (using the wafer holder).

e) Place the wafer on a clean room wipe. Blow dry with $N_2$ gun.

f) Dry the wafer holder.

7) Hard bake a) Set hotplate temperature to 95° C.

b) Place wafer on hotplate.

c) Rise temperature from 95° C. to 190° C. in 15 min.

d) Bake for 15 min at 190° C.

Metal Electroplating

Au plating on Cu working electrode

1) Electrodeposition of Au on the Cu working electrode.

a) Au counter electrode placed at the cathode.

2) Cathode current density to be used is max $j=3$ mA/cm$^2$ for growth rate of 0.1 μm/min.

3) Compute from CAD software file the area to be deposited (in cm$^2$) where the total current is I=j*area (mA) (according to Table 3).

4) Determine final deposition height by setting the deposition time in minutes (height=0.1*time (μm)).

a) For a 2 μm the deposition time of 20 minutes.

5) Connect the anode (+) of the potentiostat to a stand with a crocodile clip holding the Pt wire counter electrode, insert the electrode to the solution.

6) Connect the cathode (−) of the voltage supplier to a stand with two crocodile clips on it.

a) Big crocodile is holding the wafer; small crocodile is connected to the electrodeposited electrode.

b) To prevent damage to the wafer or to elements on it a piece of paper should be used to cover the area of the crocodile clip.

c) The big crocodile clip is not for current conduction since it is too big most of the time.

7) Set timer for 20 min.

8) Insert the wafer to the solution, the electrochemical cells should be entirely in the solution.

9) Start timer.

10) Take the wafer out of the solution and wash in DI for several seconds.

a) It is recommended to replace the piece of paper that protecting the wafer if it got wet.

Reference Electrode

Reference electrode Ag/AgCl electroplating

1) Electrodeposition of Ag on the reference Au electrode template by an aqueous plating solution of:

a) Electrolyte-DCAC: KAg(CN)$_2$-50 g/L, KCSN-200 g/L, K$_2$CO$_3$-25 g/L i) Pour 75 ml to a glass cup.

b) Ag counter plate electrode placed at the cathode.

i) Activation: wash in DI: HNO$_3$ for 20 s until the silver is white, then wash in DI water.

2) Cathode current density to be used is $j=15$ mA/cm$^2$ for growth rate of 0.8 μm/min.

3) Compute from Computer Aided Design (CAD) software file the area to be deposited (in cm$^2$), where the total current is:

a) I=j*area (mA) (according to Table 3).

4) Determine final deposition height by setting the deposition time in minutes (height=0.8*time (μm)).

a) For a 4 μm layer the deposition time was 5 minutes. 5) From total current determine resistor to be used: R=V/I while V is voltage from a voltage supply, can be set by user.

a) For example: current of 8.46 μA with 1 MΩ resistor uses V=8.46 volts.

b) Note: voltage should be higher than 5 V for a steady current.

6) Connect the resistor to the cathode (+) of the voltage supplier, than, through an ampere-meter to a stand with a crocodile clip holding the Ag counter electrode, insert the electrode to the solution.

7) Connect the anode (−) of the voltage supplier to a stand with two crocodile clips on it.

a) Big crocodile is holding the wafer; small crocodile is connected to the reference electrode.

b) To prevent damage to the wafer or to elements on it a piece of paper should be used to cover the area of the crocodile clip.

c) The big crocodile clip is not for current conduction since it was too big most of the time.

8) Set timer to 5 min.

9) Insert the wafer to the solution, the electrochemical cells should be entirely in the solution.

10) Start timer.

11) Take the wafer out of the solution and wash in DI for several seconds.

a) It is recommended to replace the piece of paper that protecting the wafer if it got wet.

12) Only if the wafer is already cut: repeat 8-10 for all reference electrodes of the same area.

13) Electroplating AgCl on Ag electrode:

a) Electrolyte-0.1M HCL for AgCl electrodes.

b) Pt counter electrode.

14) Anodic current density to be used is $j=5$ mA/cm$^2$ for growth rate of 0.28 μm/min.

15) Compute from CAD file the area to be deposited (in cm$^2$) where the total current is:

a) I=j*area (mA) (according to Table 3).

16) Determine final deposition height by setting the deposition time in minutes (height=0.28*time (μm)).

a) For a 0.84 μm layer, deposition time is 3 minutes.

17) From total current determine resistor to be used: R=V/I while V is voltage from a voltage supply, can be set by user.

a) For example: current of 8.46 μA with 1 MΩ resistor uses V=8.46 volts.

b) Note: voltage should be higher than 5 V for a steady current.

18) Connect the resistor to the anode (−) of the voltage supplier, than, through an ampere-meter to a stand with a crocodile clip holding the Pt counter electrode, insert the electrode to the solution.

19) Connect the cathode (+) of the voltage supplier to a stand with two crocodile clips on it.

a) Big crocodile is holding the wafer; small crocodile is connected to the reference electrode.

b) To prevent damage to the wafer or to elements on it a piece of paper should be used to cover the area of the crocodile clip.

c) The big crocodile clip is not for current conduction since it is too big most of the time.

20) Set timer to 3 min.

21) Insert the wafer to the solution, the electrochemical cells should be entirely in the solution.

22) Start timer.

23) Take the wafer out of the solution and wash in DI for several seconds.

a) It is recommended to replace the piece of paper that protecting the wafer if it got wet.

24) Only if wafers already cut: Repeat 20-23 for all other electrodes of the same area.

TABLE 3

Electrode dimensions and the corresponding electrical currents

| Chamber diameter (mm) | Reference electrode area ($cm^2$) | Current for Ag deposition ($\mu A$) | Current for AgCl deposition ($\mu A$) |
|---|---|---|---|
| 2 | 0.002234 | 33.51 | 11.17 |
| 1 | 0.000564 | 8.46 | 2.86 |
| 0.75 | 0.00032 | 4.8 | 1.6 |
| 0.5 | 0.000145 | 2.175 | 0.725 |
| 0.3 | 0.000035 | 0.525 | 0.175 |
| All RE in the 3D Cu/Au or PPy-coated micro-chips | 0.007704 | 116 | 38.67 |

The microchip of this example was fabricated by a photolithography process with three physical masks, as follows.

The metal conductors mask, shown in FIG. 28, specified the pattern of the gold connectors and electrodes. The mask included 5 various microchips. Each microchip contained 4 micro-chambers, marked as "1" in FIG. 28.

A layout of a single microchip and a magnified view of a single microchamber is shown in FIGS. 29A and 29B, respectively. In FIG. 29A, the metal lines from the connectors to the electrodes are shown. The diameters of the respective microchamber are indicated. The reference electrode was connected to a metal line which allowed a simultaneous electrodeposition of Ag and AgCl in all reference electrodes on the micro-chips.

The process validation marks are marked as "2" in FIG. 28, and are shown in greater detail in FIG. 30. These marks were used for a quality check for every photolithography operation. The marks width varied from 2.5 to 50 μm. Alignment marks are indicated as "3" in FIG. 28, and are shown in greater detail in FIG. 31. The marks are based on two squares enumerated "I" and "II", which identify the respective mask. Each alignment mark contains two different crosses that correspond to its matching frame on other masks. Marks for the dicing saw are indicated as "4" in FIG. 28, and are shown in greater detail in FIG. 32. A diamond dicing disc sawed the wafer according to the cross-shaped marks into 5 separate micro-chips.

The working electrode electroplating mask, shown in FIG. 33, was made for protecting the entire wafer, except of the working electrodes and the collector connectors that allowed the copper electroplating process.

The microchambers mask, shown in FIG. 34, masked the entire microchip area, except from exposed areas for the microchambers and the connectors to the experimental platform.

Example 4

A third prototype portable solid-state system for whole cell electrochemical analysis was fabricated and tested according to some embodiments of the present invention. The system included an electrochemical microchip and a microfluidic chip.

The electrochemical microchip included a PPy-coated working electrode.

Each micro-chip included 4 electrochemical micro-chambers (2 chambers with gold planar working electrodes and 2 chambers with the modified PPy-coated working electrodes). An elastic conductive polymer, polypyrrole, was electrochemically polymerized by a cyclic voltammetry technique using an EG&G Princeton Applied Research Model 273A potentiostat/galvanostat. The electrochemical polymerization bath contained 0.05 M pyrrole $C_4H_5N$ (Aldrich) and 0.1 M $LiClO_4$ (Aldrich) in acetonitrile $CH_3CN$ (Sigma-Aldrich). A Pt plate was used as a counter electrode and Calomel (KCl saturated) was employed as a reference electrode. Pre-selected potential ranges were scanned between 0.0 and 1.2 V vs. SCE reference electrode. The polypyrrole growth is controlled by the number of cycles. The scan rate was 20 mV/s. The polymerization process started at a potential of 0.6-0.7 V. Following is a detailed description of the fabrication process employed in the present example.

Metal Definition

AZ-5214 negative photoresist lithography procedure (1$^{st}$ mask)

1) Wafer preparation a) Wafer cleaning i) Simple clean—removal of organic contaminants Process:

(a) Cover the surface of the wafer with acetone.

(b) Thoroughly scrub the surface of the wafer with a swab.

(c) Rinse the wafer with isopropanol (IPA).

(d) Blow dry the wafer with $N_2$ gun.

ii) Photoresist stripper (Nanostrip, piranha)

iii) RCA clean—removal of organic, oxide, and metallic contaminants

Process:

(a) Organic clean: removal of insoluble organic contaminants with a 5:1:1 $H_2O:H_2O_2:NH_4OH$ solution.

(b) Oxide strip: removal of a thin silicon dioxide layer where metallic contaminants may accumulated using a diluted 20:1 $H_2O:HF$ solution.

(c) Ionic clean: removal of ionic and heavy metal atomic contaminants using a solution of 6:1:1 $H_2O:H_2O_2:HCl$.

iv) Piranha clean—removal of organic materials (photoresist, oil, etc.)

Process:

(a) Mix 98% $H_2SO_4$ (sulfuric acid) and 30% $H_2O_2$ (hydrogen peroxide) in volume ratios of 2-4:1

(b) Heat to 100° C.

(c) Insert wafers to the solution and wait for 10 min.

(d) Take the wafers out of the solution and rinse in deionized water (DI) for 5 min.

(e) Dry with $N_2$ gun.

b) Dehydration bake
  i) Set the hotplate to 120° C.
  ii) Transfer wafers to a metal wafer carrier.
  iii) Bake the wafers for 10 min on the hotplate.
  iv) Remove the wafer carrier from the hotplate using tweezers.
c) Mask cleaning
  i) Place the mask in the mask cleaning holder.
  ii) Apply acetone to the chrome surface. Do not allow the mask to dry with acetone on it.
  iii) Scrub the chrome surface with a swab.
  iv) Rinse the mask with IPA.
  v) Dry with $N_2$ gun.
2) Apply photoresist
  a) Photoresist coating
    i) Mount the wafer on the RC-8 Spinner.
    ii) Apply a quarter size puddle of HMDS (adhesion promoter) to wafer.
    iii) Set the spinner to spin at 500 rpm with acceleration equal to 1000 rpm/s for 5 s, with open cover. Next, set the spinner to spin at 1300 rpm with acceleration of 3000 rpm/s for 30 s.
    iv) Start spinning.
    v) Apply a quarter sized puddle of AZ-5214 (negative resist) to wafer.
    vi) Use same spin program, this results in 1.6 micron thickness of resist.
    vii) Clean the spinner when done.
3) Softbake
  a) Heat the hotplate next to the RC-8 Spinner to 112° C.
  b) Set timer for 60 s.
  c) Place the wafer on the hotplate, start timing.
  d) When the time is up, remove the wafer.
4) Expose
  a) Calculate the exposure time (Exposure dose/Measured intensity)
  b) Set Karl Suss MA-6 mask aligner to: Soft contact, exposure time 0.8 s.
  c) Expose the wafer.
  d) If soft or hard contact was used, clean the mask.
  e) Create an entry in the Karl Suss aligner log book when done.
5) Post exposure bake
  a) Set a hotplate to 120° C.
  b) Set timer for 2 min.
  c) Place the wafer on the hotplate, start timing.
  d) When the time is up, remove the wafer.
6) Flood exposure
  a) Without mask, expose wafer for 40 s.
7) Develop
  a) Pour AZ-726 developer to a Petri dish to cover the wafer.
  b) Set timer to 35 s.
  c) Start the timer. Place the wafer in the developer bath.
  d) Quickly remove the wafer from the developer bath and rinse it in the water bath for 30 s (using the wafer holder).
  e) Place the wafer on a clean room wipe. Blow dry with $N_2$ gun.
  f) Dry the wafer holder.
8) Clean the workstation.
Metal Deposition
  Gold (Au)/Chromium (Cr) evaporation using Edwards 306 evaporator
9) Plasma clean—insert wafers to microwave plasma cleaning oven for 1 min.
10) Clean and dry wafers.
11) Vent chamber
  a) Open nitrogen gas cylinder (set the regulator to 0.5 bar).
  b) Press seal, wait for 10 s and press vent. The chamber takes about 2 min to vent. Wait until the hissing stops and the pressure is 1000 mbar.
  c) Attempt to open the chamber by gently lifting the bell jar. If the bell jar is hard to lift, it has not finished venting.
  d) Once you have removed the bell jar, place it inverted on the cork ring, stop the venting process. Press seal and close the nitrogen cylinder.
12) Mount the wafers
  a) Securely attach wafers onto sample holder using the bolts and washers (this will be mounted upside down).
  b) Bolt the holder onto the bottom of the driven bearing using the bolt provided.
  c) Turn the knob fully clockwise on the rotary stage controller and switch it on (using the switch the neon should light).
13) Pump
  a) Replace the bell jar and implosion guard.
  b) Press cycle on the pumping system controller. The chamber must pump down to below $1\times10^{-4}$ mbar before the plasma processing can be started (Ideally you should wait until it reaches below $5\times10^{-7}$ mbar for the best results).
14) Evaporation of chromium
  a) Check the thickness monitor controller (FTM5) is correctly configured (by cycling through the parameters using the data button): Layer=1, Density=7.2 and z-value=28.9 if these values are not correct change them using the inc/dec buttons.
  b) Ensure the pressure is below $5\times10^{-7}$ mbar, if it is not wait ideally until it is at $2\times10^{-7}$ mbar.
  c) Open the shutter on the thickness monitor controller (FTM5), select A on the LT selector switch and select LT on the right-hand selector switch.
  d) Slowly increase the current (using the graduated current control knob) while watching the reflection of the chromium rod in the minor, it should start to glow initially at the ends, keep the current constant until the glow extends along its length.
  e) Limit the current so that the pressure never exceeds $5\times10^{-6}$ mbar (and ideally stays below $1\times10^{-6}$ mbar).
  f) Continue to gradually increase the current (so that the rod is glowing evenly) until the thickness monitor displays a rate of 0.1 or 0.2 nm s$^{-1}$ then wait until the layer is almost (<0.3 nm away) the desired thickness of 15 nm and turn the current down to zero.
  g) Switch the right-hand selector switch back to 0 and close the shutter on the thickness monitor controller (FTM5).
  h) Wait for about 5 min for the system to cool down and the pressure to return to $2\times10^{-7}$ mbar.
15) Evaporation of gold
  a) Check the thickness monitor controller (FTM5) is correctly configured (by cycling through the parameters using the data button): Layer=2, Density=19.3 and z-value=23.2 if these values are not correct change them using the inc/dec buttons.
  b) Ensure the pressure is below $5\times10^{-7}$ mbar, if it is not wait ideally until it is at $2\times10^{-7}$ mbar.
  c) Open the shutter on the thickness monitor controller (FTM5), select B on the LT selector switch and select LT on the right-hand selector switch.
  d) Then slowly increase the current (using the graduated current control knob) while watching the reflection of the boat containing the gold in the mirror, it should start to glow initially at the ends, keep the current constant until the boat is glowing evenly.

e) Continue to gradually increase the current (so that the boat is glowing evenly) eventually the gold will melt, at this point the pressure will rise especially if this is the first time a gold slug is melted.

f) Limit the current so that the pressure never exceeds $5\times10^{-6}$ mbar (and ideally stays below $1\times10^{-6}$ mbar).

g) Once the gold has melted increase the current until the thickness monitor displays a rate of 0.5 to 1 nm s$^{-1}$ then wait until the layer is almost (<2 nm away) the desired thickness of 300 nm and turn the current down to zero.

i) Do not let wafer heat to 80-90° C., when wafer heats close current and let it cool down to 50° C.

h) Switch the right-hand selector switch back to 0 and close the shutter on the thickness monitor controller (FTM5).

i) Wait for about 5 min for the system to cool down and the pressure to return to $2\times10^{-7}$ mbar.

16) Retrieve wafers a) Switch the switch on the rotary stage controller to stop the sample stage rotating.

b) Open the nitrogen gas cylinder (set the regulator to 0.5 bars) and line to the evaporator.

c) Press seal wait 10 s and then press vent on the pumping system controller. The display will show chamber vent. The chamber will take about two minutes to vent.

d) Wait until the hissing stops and the pressure is reading $1\times10^3$ mbar.

e) Attempt to open the chamber by gently lifting the bell jar. If the bell jar is hard to lift, it has not finished venting.

f) Remove the bell jar and place it inverted on the cork ring.

g) Stop the venting process by pressing seal on the pumping system controller.

h) Close the nitrogen cylinder.

i) Unbolt the substrate holder from the bottom of the driven bearing and withdraw the holder.

j) Replace the bell jar and implosion guard and then press cycle on the pumping system controller to pump the system down to keep the inside of the system as clean as possible.

k) Remove the samples from the sample holder, rap the sample holder in tin foil and leave it on the evaporator for the next user.

Cleaning

AZ-5214 photoresist removal

6) Insert wafers to NMP bath.

7) Heat NMP bath to 80° C.

8) Heat ultrasound bath to 80° C.

9) Place NMP bath with wafers in ultrasound bath.

10) Start ultrasound, wait until resist lifts-off, 40-60 min.

Passivation

SU-8 negative photoresist lithography procedure (3$^{rd}$ mask)

8) Wafer preparation a) Wafer cleaning i) Simple clean—removal of organic contaminants Process:

(a) Cover the surface of the wafer with acetone.

(b) Thoroughly scrub the surface of the wafer with a swab.

(c) Rinse the wafer with IPA.

(d) Blow dry the wafer with N$_2$ gun.

b) Dehydration bake i) Set the hotplate to 120° C.

ii) Transfer wafers to a metal wafer carrier.

iii) Bake the wafers for 15 min in the oven.

iv) Remove the wafer carrier from the oven using tweezers.

c) Mask cleaning i) Place the mask in the mask cleaning holder.

ii) Apply acetone to the chrome surface. Do not allow the mask to dry with acetone on it.

iii) Scrub the chrome surface with a swab.

iv) Rinse the mask with IPA.

v) Dry with N$_2$ gun.

9) Apply photoresist a) Photoresist coating i) Mount the wafer on the Headway spinner.

ii) Apply a quarter sized puddle of SU-8 3050 to wafer.

iii) Set spread cycle to 500 rpm with acceleration equal to 100 rpm/s for 10 s.

iv) Set the spinner to spin at 3000 rpm with acceleration equal to 300 rpm/s for 30 s.

v) Start spinning.

vi) This gives 50 micron thickness of resist.

vii) Clean the spinner when done.

10) Softbake a) Heat the hotplate next to the Headway spinner to 95° C.

b) Set timer for 30 min.

c) Place the wafer on the hotplate, start timing.

d) When the time is up, remove the wafer.

11) Expose a) Calculate the exposure time (Exposure dose/Measured intensity)

b) Set Karl Suss MA-6 mask aligner to: Soft contact, exposure time 30 s.

c) Expose the wafer.

d) If soft or hard contact was used, clean the mask.

e) Create an entry in the Karl Suss aligner log book when done.

12) Post exposure bake a) Set a hotplate to 95° C.

b) Set timer for 10 min.

c) Place the wafer on the hotplate, start timing.

d) When the time is up, remove the wafer.

13) Develop a) Pour PM-Acetate developer to a Petri dish to cover the wafer.

b) Set timer to 8 min.

c) Start the timer. Place the wafer in the developer bath.

d) Quickly remove the wafer from the developer bath and rinse with IPA for 30 s (using the wafer holder).

e) Place the wafer on a clean room wipe. Blow dry with N$_2$ gun.

f) Dry the wafer holder.

14) Hard bake a) Set hotplate temperature to 95° C.

b) Place wafer on hotplate.

c) Rise temperature from 95° C. to 190° C. in 15 min.

d) Bake for 15 min at 190° C.

Reference Electrode

Reference electrode Ag/AgCl electroplating

25) Electrodeposition of Ag on the reference Au electrode template by an aqueous plating solution of:

a) Electrolyte-DCAC: KAg(CN)$_2$-50 g/L, KCSN-200 g/L, K$_2$CO$_3$-25 g/L i) Pour 75 ml to a glass cup.

b) Ag counter plate electrode placed at the cathode.

i) Activation: wash in DI: HNO$_3$ for 20 s until the silver is white, then wash in DI water.

26) Cathode current density to be used is j=15 mA/cm$^2$ for growth rate of 0.8 μm/min.

27) Compute from Computer Aided Design (CAD) software file the area to be deposited (in cm$^2$), where the total current is:

a) I=j*area (mA) (according to Table 3).

28) Determine final deposition height by setting the deposition time in minutes (height=0.8*time (μm)).

a) For have a 4 μm layer the deposition time was 5 minutes.

29) From total current determine resistor to be used: R=V/I while V is voltage from a voltage supply, can be set by user.
 a) For example: current of 8.46 µA with 1 MΩ resistor uses V=8.46 volts.
 b) Note: voltage should be higher than 5 V for a steady current.
30) Connect the resistor to the cathode (+) of the voltage supplier, than, through an ampere-meter to a stand with a crocodile clip holding the Ag counter electrode, insert the electrode to the solution.
31) Connect the anode (−) of the voltage supplier to a stand with two crocodile clips on it.
 a) Big crocodile is holding the wafer; small crocodile is connected to the reference electrode.
 b) To prevent damage to the wafer or to elements on it a piece of paper should be used to cover the area of the crocodile clip.
 c) The big crocodile clip is not for current conduction since it was too big most of the time.
32) Set timer to 5 min.
33) Insert the wafer to the solution, the electrochemical cells should be entirely in the solution.
34) Start timer.
35) Take the wafer out of the solution and wash in DI for several seconds.
 a) It is recommended to replace the piece of paper that protecting the wafer if it got wet.
36) Only if the wafer is already cut: repeat steps 8-10 for all reference electrodes of the same area.
37) Electroplating AgCl on Ag electrode:
 a) Electrolyte—0.1M HCL for AgCl electrodes.
 b) Pt counter electrode.
38) Anodic current density to be used is j=5 mA/cm$^2$ for growth rate of 0.28 µm/min.
39) Compute from CAD file the area to be deposited (in cm$^2$) where the total current is:
 a) I=j*area (mA) (according to Table 3).
40) Determine final deposition height by setting the deposition time in minutes (height=0.28*time (µm)).
 a) For have a 0.84 µm layer the deposition time is 3 minutes.
41) From total current determine resistor to be used: R=V/I while V is voltage from a voltage supply, can be set by user.
 a) For example: current of 8.46 µA with 1 MΩ resistor uses V=8.46 volts.
 b) Note: voltage should be higher than 5 V for a steady current.
42) Connect the resistor to the anode (−) of the voltage supplier, than, through an ampere-meter to a stand with a crocodile clip holding the Pt counter electrode, insert the electrode to the solution.
43) Connect the cathode (+) of the voltage supplier to a stand with two crocodile clips on it.
 a) Big crocodile is holding the wafer; small crocodile is connected to the reference electrode.
 b) To prevent damage to the wafer or to elements on it a piece of paper should be used to cover the area of the crocodile clip.
 c) The big crocodile clip is not for current conduction since it is too big most of the time.
44) Set timer to 3 min.
45) Insert the wafer to the solution, the electrochemical cells should be entirely in the solution.
46) Start timer.
47) Take the wafer out of the solution and wash in DI for several seconds.
 a) It is recommended to replace the piece of paper that protecting the wafer if it got wet.
48) Only if wafers already cut: Repeat steps 20-23 for all other electrodes of the same area.

Polymer Electropolymerization
Electropolymerization of Polypyrrole

An elastic conductive polymer, polypyrrole, was electrochemically polymerized by a cyclic voltammetry technique using an EG&G Princeton Applied Research Model 273A potentiostat/galvanostat. The electrochemical polymerization bath contained 0.05 M pyrrole $C_4H_5N$ (Aldrich) and 0.1 M $LiClO_4$ (Aldrich) in acetonitrile $CH_3CN$ (Sigma-Aldrich). A Pt plate was used as a counter electrode and Calomel (KCl saturated) was employed as a reference electrode (FIG. 35). Pre-selected potential ranges were scanned between 0.0 and 1.2 V vs. SCE reference electrode. The polypyrrole growth is controlled by the number of cycles. The scan rate was 20 mV/s. The polymerization process started at a potential of 0.6-0.7 V.

Masks number 1 and 3 from the Cu/Au modified electrode process (see Example 3) were used to pattern the gold electrode micro-chips.

Example 5

Systems fabricated as described in Examples 4 and 5 above were used in Toxicity bio-detection assays.

Bacterial Strain Culture Preparation

*Escherichia coli* strain RFM443ΔphoA/pBR2TTS cells harboring a sulA::phoA fusion were used for electrophoretic bio-deposition experiments. Nalidixic acid (NA) served as the model toxicant for bio-detection (see FIG. 13). The *E. coli* cells were grown overnight in Luria-Bertani (LB) growth medium containing 0.1 mg/ml ampicillin with shaking at 37° C. The overnight culture was diluted ×1/150, regrown to an optical density (600 nm) of 0.2.

Toxicity Bio-Detection Assays

Nalidixic acid (NA, FW 254.22, Sigma) was added to the refreshed bacterial suspension to a final concentration of 5 µg/ml. Following further incubation of 1 hour with shaking at 37° C., the enzymatic substrate para-Aminophenyl phosphate (pAPP, MW 211.09, diagnoSwiss) was added reaching a concentration of 0.8 mg/ml, and immediately aliquots of 3 µl were introduced into the electrochemical micro-chambers. Chrono-amperometric measurement was applied with a constant potential of 300 mV (PalmSens potentiostat with an eight channel multiplexer, PalmSens) vs. Ag/AgCl in the electrochemical chamber. Control samples were prepared with the addition of growth medium instead of NA to the incubation stage in order to verify the influence of NA on the induction of the bacteria.

Results and Discussion

The electrochemical activity of the systems was validated by a cyclic voltammetry assay with a redox couple of Ferrocyanide/Ferricyanide electro-active solution. The cyclic voltammograms that resulted from the electrochemical micro-chambers with the PPy-coated working electrode for different scan rates are shown in FIG. 36A. The voltammograms using the electrochemical micro-chip show clearly the cathodic reduction of the $Fe^{3+}$ and the anodic oxidation of the $Fe^{2+}$. The peak of the anodic and the cathodic currents and the associated applied potential (vs. the open Ag/AgCl reference electrode) were extracted and plotted versus the square root of the scan rate respectively (FIGS. 36B and 36C). The current peak plot of both PPy-coated and Au planar working electrodes yielded a positive linear relation for anodic currents and a negative linear relation for cathodic currents. The resulted linear relation values are shown in Table 4, below. The slope values calculated for the PPy-coated working electrode were about 10 times higher than the values measured for the Au planar electrode. This variation may be attributed to the surface area of the PPy-coated electrode is bigger than the surface area of the Au planar electrode. The applied potentials at the peaks of the anodic and the cathodic currents measured with the PPy-coated working electrode yielded a positive and a negative non-linear relation respectively, in oppose to the negligible change measured with the Au planar working electrode. The present inventor postulate that this dependence is due to the fact that Nernst equation is slightly modified when the electro-active species concentration is changed near the electrode due to the tenfold higher rate of the redox reaction on the PPy-coated electrode.

TABLE 4

Resulted linear relations of the anodic and the cathodic current peaks for both PPy-coated and Au planar working electrodes

| Working electrode | Type of current | Slope [$\mu A/V^{0.5} s^{-0.5}$] | Intercept [$\mu A$] |
|---|---|---|---|
| PPy-coated | Anodic | 80.5 ± 4.0 | −1.80 ± 1.20 |
|  | Cathodic | −71.0 ± 3.0 | −0.70 ± 0.80 |
| Au planar | Anodic | 8.4 ± 0.4 | 0.40 ± 0.12 |
|  | Cathodic | −6.8 ± 0.4 | −0.70 ± 0.12 |

The effective surface area of the PPy-coated electrode was evaluated. The peak current can be calculated from Bard et al. supra;

$$I_{peak} = 0.4463 \left(\frac{F^3}{RT}\right)^{1/2} n^{3/2} A D^{1/2} C^* v^{1/2} \quad (1)$$

where F [C mol$^{-1}$] is the Faraday constant, R [J mol$^{-1}$ K$^{-1}$] is the gas constant, T [K] is the temperature, n is the stoichiometric number of electrons involved in an electrode reaction, A [cm$^2$] is the surface area of the electrode, D [cm$^2$ s$^{-1}$] is the diffusion coefficient of the electro-active species, C* [mol cm$^{-3}$] is the bulk concentration of the electro-active species, v [V s$^{-1}$] is the linear potential scan rate, and $I_{peak}$ [amperes] is the peak current. The ratio of the surface areas of the PPy-coated electrode and the Au planar electrode was experimentally obtained from the ratio of the slope values resulted from the linear relation between the anodic peak currents of the two electrodes and the square root of the scan rate. The experimental ratio obtained was 9.58 and was approximately 8.8 times higher than the ratio of the calculated surface areas of the electrodes (1.09, for $A_{PPy\text{-}coated}$=9.83·10$^{-4}$ [cm$^2$] and $A_{Au\,planar}$=8.98·10$^{-4}$ [cm$^2$]). This variation can be attributed to fact that the PPy-coated electrode was modeled as a close cylinder with smooth surface area. PPy films are known to be very porous with high roughness values. Both high porosity and roughness values result in PPy-coated electrodes with large surface area. Incorporating the porosity and the roughness parameters into the calculations of the surface area of the PPy-coated electrode result in more accurate surface area calculations. On the other hand, The effective surface area of the PPy-coated electrode can be calculated from the anodic slope value in Table 4 and the linear relation described in Eq. (1). The resulted effective surface area of the PPy-coated working electrode was 1.08·10$^{-2}$±0.05·10$^{-2}$ [cm$^2$] and was calculated at 25° C. when n was 1, D for ferricyanide diffusion was 0.77·10$^{-5}$ [cm$^2$ s$^{-1}$], and C* for 10 mM Ferricyanide was 10$^{-5}$ [mol cm$^{-3}$]. This surface area value was 11-fold higher than the calculated value which described more clearly the high effect of the porosity and the roughness of the PPy film on the resulted electrode porosity and the generated electrochemical current.

The electrochemical activity of the 3D Cu/Au working electrode was characterized with a cyclic voltammetry assay with a redox couple of Ferrocyanide/Ferricyanide electroactive solution. The cyclic voltammograms that resulted from the electrochemical micro-chambers with the 3D Cu/Au working electrode for different scan rates are shown in FIG. 37A. The voltammograms using the electrochemical microchip show clearly the cathodic reduction of the Fe$^{3+}$ and the anodic oxidation of the Fe$^{2+}$. The peak of the anodic and the cathodic currents and the associated applied potential (vs. the open Ag/AgCl reference electrode) were extracted and plotted versus the square root of the scan rate respectively (FIGS. 37B and 37C). The current peak plot of the 3D Cu/Au working electrode yielded a positive linear relation for anodic currents and a negative linear relation for cathodic currents. The resulted linear relation values are shown in Table 5. Furthermore, the applied potentials at the peaks of the anodic and the cathodic currents measured with the 3D Cu/Au working electrode yielded a mild negative linear relation which can be attributed to the slight modification of Nernst equation due to the change with the electro-active species concentration near the electrode during the redox reaction.

TABLE 5

Resulted linear relations of the anodic and the cathodic current peaks for 3D Cu/Au working electrode.

| Working electrode | Type of current | Slope [$\mu A/V^{0.5} s^{-0.5}$] | Intercept [$\mu A$] |
|---|---|---|---|
| 3D Cu/Au | Anodic | 10.0 ± 2.0 | 1.00 ± 0.50 |
|  | Cathodic | −9.4 ± 1.2 | −1.20 ± 0.34 |

The effective surface area of the 3D Cu/Au electrode was evaluated. The peak current can be calculated from Eq. (1). The ratio of the surface areas of the 3D Cu/Au electrode and the Au planar electrode was experimentally obtained from the ratio of anodic peak currents of the two electrodes. The experimental ratio obtained was 5.32 and was calculated from the cyclic voltammogram of both electrodes at a scan rate of 150 mV/s. The ratio was approximately 4.7 times higher than the ratio of the calculated surface areas of the electrodes (1.14, for $A_{3D\,Cu/Au}$=1.026·10$^{-3}$ [cm$^2$] and $A_{Au\,planar}$=0.898·10$^{-3}$ [cm$^2$]). This variation can be attributed to the fact that the 3D Cu/Au electrode was assumed to be a cylinder with smooth surface area.

According to confocal scanning laser microscopy images the surface area of the 3D Cu/Au electrode is rough which may be attributed to the copper electrodeposition process. Considering the roughness factor during the surface area calculations provides a more accurate effective surface area of the electrode. Still, the effective surface area of the electrode can be calculated from the linear relation described in Eq. (1) and the resulted slope values in Table 5. The calculated effective surface area of the 3D Cu/Au working electrode was 1.35·10$^{-3}$±0.25·10$^{-3}$ [cm$^2$] and was calculated from the resulted anodic slope at 25° C. when n was 1, D for ferricyanide diffusion was 0.77·10$^{-5}$ [cm$^2$ s$^{-1}$], C* for 10 mM Ferricyanide was 10$^{-5}$ [mol cm$^{-3}$]. However, the updated calculated surface areas ratio was 1.5 which is still 3.6 times lower than the anodic current peaks ratio. The reason for this variation may be due to edge effects which increased the current densities at the edge of the electrode and resulted in increased diffusion rates of the electro-active species towards these edges.

Increasing the surface area of the working electrode can result in higher electrochemical currents which may increase the bio-detection efficiency in whole-cell bio-chips. The bio-detection of toxins with whole-cell biosensors was studied with two modified working electrodes; 3D Cu/Au electrode and PPy-coated electrode. Chrono-amperometric results of *E. coli* cells in the presence and the absence of NA detected with either a 3D Cu/Au or Au planar electrodes is shown in FIG. 37A. The results obtained demonstrated higher currents detected by the 3D Cu/Au working electrode compared to the Au planar working electrode. Chrono-amperometric results of *E. coli* cells in the presence and the absence of NA detected with either a PPy-coated or Au planar electrodes is shown in FIG. 38B. Higher electrochemical currents were generated when PPy-coated electrode was used compared to Au planar electrode.

The bio-detection efficiency was evaluated by calculating induction factor (IF) values (Eq. 2).

$$\text{Induction factor} = \frac{I @ 600s_{in\ the\ presence\ of\ toxicants}}{I @ 600s_{in\ the\ absence\ of\ toxicants}} \quad (2)$$

The resulted IF values for either PPy-coated electrode, 3D Cu/Au electrode, or Au planar electrode are shown in FIG. 39. This comparison demonstrates that using a 3D Cu/Au electrode as a working electrode in a whole-cell bio-chip resulted in bio-detection efficiency value higher by about 24% compared to the Au planar electrode. This improvement can be attributed to the high surface area and roughness of the 3D Cu/Au electrode combined with the high conductivity of the gold and copper and edge effects that increase the overall generated current density. Using a PPy-coated electrode as a working electrode reduced the bio-detection efficiency in 64% compared to the Au planar electrode. This reduction may be attributed to the relatively low conductivity properties of the PPy which decrease the electron transfer efficiency during the redox reaction upon the electrode, and/or a possible reaction between the PPy and the electro-active species in the bacterial growth medium.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of analyzing liquid, comprising;
submerging in the liquid a system which comprises:
an electrochemical unit having an electrochemical microchamber for receiving a sample of the liquid and electrochemically analyzing said sample, said microchamber comprising a working electrode, a reference electrode and a counter electrode on a base of said microchamber, wherein a height of said working electrode above said base is at least 10 times higher than a height of any of said reference and said counter electrodes; and
a microfluidic unit being attached to said electrochemical unit and having microchannels constituted for sampling said sample in situ and feeding said sample to said electrochemical microchamber; and
analyzing signals produced by said electrochemical unit.

2. A system for analyzing a liquid, comprising:
an electrochemical unit having an electrochemical microchamber for receiving a sample of the liquid and electrochemically analyzing said sample, and a biological sensor capable of producing electrochemical signal in said microchamber, wherein said biological sensor comprises a cell having a nucleic acid expression construct which comprises a promoter sequence which comprises a sulA:phoA fusion as set forth in SEQ ID NO: 1, and which is operatively linked to a reporter gene, wherein an activity/expression of said reporter gene is responsive to genotoxicants which induce DNA synthesis halt, multiple-target attacks on DNA and or, DNA cross linking; and
a microfluidic unit being attached to said electrochemical unit and having microchannels constituted for sampling said sample in situ and feeding said sample to said electrochemical microchamber.

3. A system for analyzing a liquid, comprising:
an electrochemical unit having an electrochemical microchamber for receiving a sample of the liquid and electrochemically analyzing said sample, said microchamber comprising a working electrode, a reference electrode and a counter electrode on a base of said microchamber, wherein a height of said working electrode above said base is at least 10 times higher than a height of any of said reference and said counter electrodes; and
a microfluidic unit being attached to said electrochemical unit and having microchannels constituted for sampling said sample in situ and feeding said sample to said electrochemical microchamber.

4. The system of claim 3, wherein said microfluidic unit is configured for said sampling while said electrochemical unit and said microfluidic unit are both submerged in the liquid.

5. The system of claim 3, further comprising a sealed encapsulation for sealing said electrochemical unit and said microfluidic unit except for an inlet port of said microfluidic unit.

6. The system of claim 3, wherein said microfluidic unit comprises an integrated pump for pumping said sample from an environment near the system to said microchannels.

7. The system of claim 3, wherein said electrochemical unit comprises at least one additional microchamber.

8. The system of claim 3, wherein said working electrode is a planar working electrode.

9. The system of claim 3, wherein said working electrode is coated by a conductive polymer.

10. The system of claim 3, wherein said working electrode is shaped as a pillar projecting upwardly from said base of said microchamber.

11. The system of claim 3, wherein said electrochemical unit comprises a biological sensor capable of producing electrochemical signal in said microchamber.

12. The system of claim 11, wherein said biological sensor comprises a cell having a nucleic acid expression construct which comprises a promoter sequence operatively linked to a reporter gene, wherein an activity/expression of said reporter gene is responsive to genotoxicants which induce DNA synthesis halt, multiple-target attacks on DNA and or DNA cross linking.

13. The system of claim 3, wherein the liquid is water and said electrochemical unit is configured for detecting water toxicity.

14. The system of claim 12, wherein said promoter sequence operatively linked to said reporter gene comprises a sulA:phoA fusion as set forth in SEQ ID NO: 1.

15. A method of manufacturing a system for analyzing a liquid, comprising:
forming a microchamber in a substrate and depositing a working electrode, a reference electrode and a counter electrode on a base thereof thereby providing an electrochemical unit, wherein a height of said working electrode above said base is at least 10 times higher than a height of any of said reference and said counter electrodes;
forming a microfluidic unit having microchannels; and
assembling said microfluidic unit and said electrochemical unit such as to establish fluid communication between said microchannels and said microchamber.

16. The method of claim 15, further comprising encapsulating the system with a sealed encapsulation in a manner such that an inlet port of said microfluidic unit remains exposed to an environment near the system.

* * * * *